US010598591B2

(12) United States Patent
Fujiyama et al.

(10) Patent No.: US 10,598,591 B2
(45) Date of Patent: *Mar. 24, 2020

(54) MOISTURE CONTENT OBSERVATION DEVICE, MOISTURE CONTENT OBSERVATION METHOD, CULTIVATION DEVICE AND SAMPLE

(71) Applicant: PANASONIC INTELLECTUAL PROPERTY MANAGEMENT CO., LTD., Osaka (JP)

(72) Inventors: Takeshi Fujiyama, Fukuoka (JP); Yuuji Terashima, Fukuoka (JP); Hisahiro Tanaka, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 3 days.

This patent is subject to a terminal disclaimer.

(21) Appl. No.: 16/074,285

(22) PCT Filed: May 11, 2017

(86) PCT No.: PCT/JP2017/017795
§ 371 (c)(1),
(2) Date: Jul. 31, 2018

(87) PCT Pub. No.: WO2017/208765
PCT Pub. Date: Dec. 7, 2017

(65) Prior Publication Data
US 2019/0265162 A1    Aug. 29, 2019

(30) Foreign Application Priority Data
May 31, 2016    (JP) .................................. 2016-109562

(51) Int. Cl.
*G01N 21/00* (2006.01)
*G01N 21/3554* (2014.01)
(Continued)

(52) U.S. Cl.
CPC .......... *G01N 21/3554* (2013.01); *A01G 7/00* (2013.01); *A01G 7/045* (2013.01); *A01G 27/00* (2013.01);
(Continued)

(58) Field of Classification Search
CPC ............. G01N 21/3554; G01N 21/359; G01N 2021/8466; A01G 7/045; A01G 27/00;
(Continued)

(56) References Cited

U.S. PATENT DOCUMENTS

2017/0115210 A1*  4/2017  Fujiyama ........... G01N 21/3554
2018/0284016 A1  10/2018  Fujiyama et al.
2018/0372624 A1* 12/2018  Fujiyama ................. A01G 7/00

FOREIGN PATENT DOCUMENTS

JP    4-160346 A    6/1992
JP    5-236831 A    9/1993
(Continued)

OTHER PUBLICATIONS

International Search Report issued in International Patent Application No. PCT/JP2017/017795, dated Aug. 15, 2017.
(Continued)

*Primary Examiner* — Abdullahi Nur
(74) *Attorney, Agent, or Firm* — Greenblum & Bernstein, P.L.C.

(57) ABSTRACT

A true leaf and a plurality of artificial leaves are attached on a white reference substrate. A first light source radiates a reference beam of 905 nm while sequentially scanning toward the white reference substrate. A second light source radiates a measuring beam of 1550 nm while sequentially
(Continued)

scanning toward the white reference substrate. A threshold level setter/water content index detector calculates a relative water content of a true leaf based on the intensity of each reflection light of the reference beam and the measuring beam which are respectively reflected by the true leaf and a plurality of artificial leaves.

11 Claims, 42 Drawing Sheets

(51) Int. Cl.
```
A01G 7/04      (2006.01)
G01N 21/27     (2006.01)
G01N 21/359    (2014.01)
G06T 7/00      (2017.01)
A01G 27/00     (2006.01)
A01G 7/00      (2006.01)
G01N 21/3563   (2014.01)
G01N 21/84     (2006.01)
```
(52) U.S. Cl.
CPC ......... *G01N 21/274* (2013.01); *G01N 21/359* (2013.01); *G01N 21/3563* (2013.01); *G06T 7/001* (2013.01); *G01N 2021/8466* (2013.01); *G06T 2207/10048* (2013.01); *G06T 2207/30188* (2013.01)

(58) Field of Classification Search
CPC . A01G 7/00; G06T 7/001; G06T 2207/10048; G06T 2207/30188
See application file for complete search history.

(56) References Cited

FOREIGN PATENT DOCUMENTS

| | | |
|---|---|---|
| JP | 9-318766 A | 12/1997 |
| JP | 2001-141650 | 5/2001 |
| JP | 2001-272373 | 10/2001 |
| JP | 2004-285265 A | 10/2004 |
| JP | 2005-308733 | 11/2005 |
| JP | 2007-306846 | 11/2007 |
| JP | 2009-197104 A | 9/2009 |
| JP | 5258044 | 5/2013 |
| WO | 2015/098063 | 7/2015 |

OTHER PUBLICATIONS

U.S. Appl. No. 16/155,357 to Takeshi Fujiyama et al., filed Oct. 9, 2018.
U.S. Appl. No. 15/779,759 to Takeshi Fujiyama et al., filed May 29, 2018.
U.S. Appl. No. 16/066,216 to Takeshi Fujiyama et al., filed Jun. 26, 2018.
U.S. Appl. No. 16/065,892 to Takeshi Fujiyama et al., filed Jun. 25, 2018.
The Extended European Search Report dated Apr. 25, 2019 for the related European Patent Application No. 17806323.6.
E.Raymond Hunt et al: "Detection of Changes in Leaf Water Content Using Near- and Middle-Infrared Reflectances", Remote Sensing of Environment., vol. 30, No. 1, 1989, pp. 43-54, XP055516278.

* cited by examiner

FIG. 9
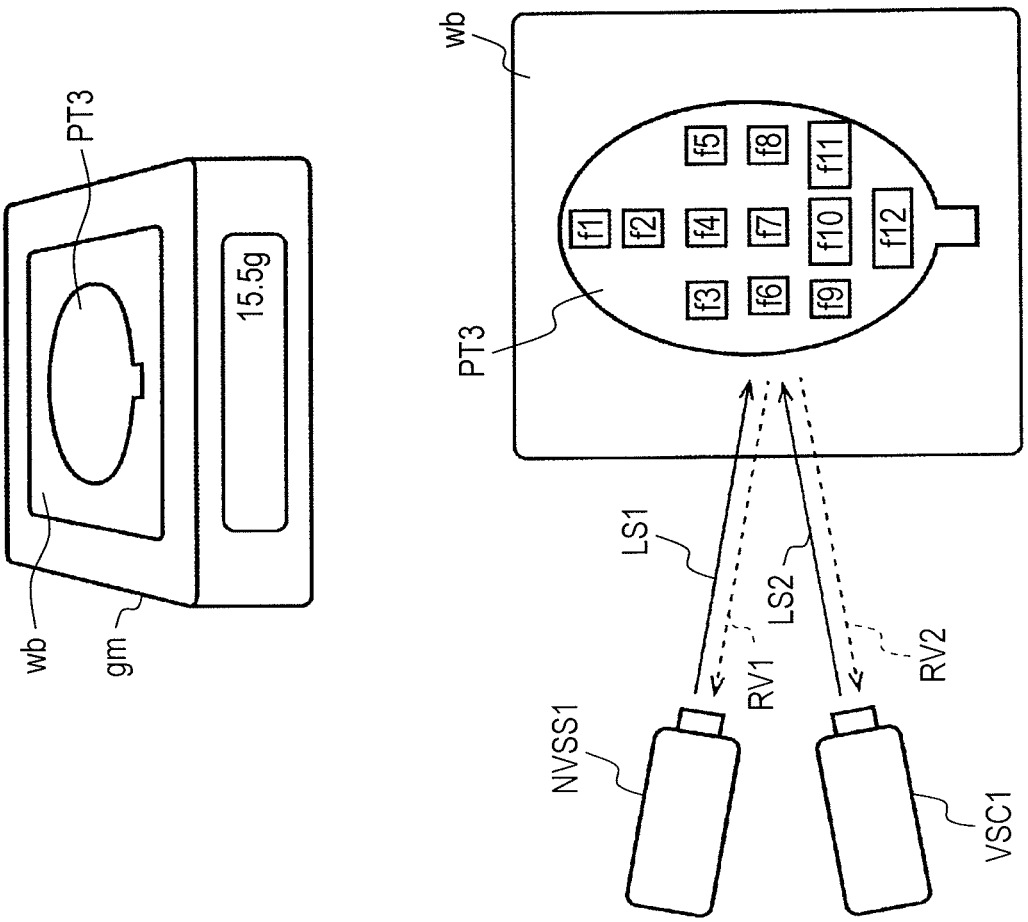
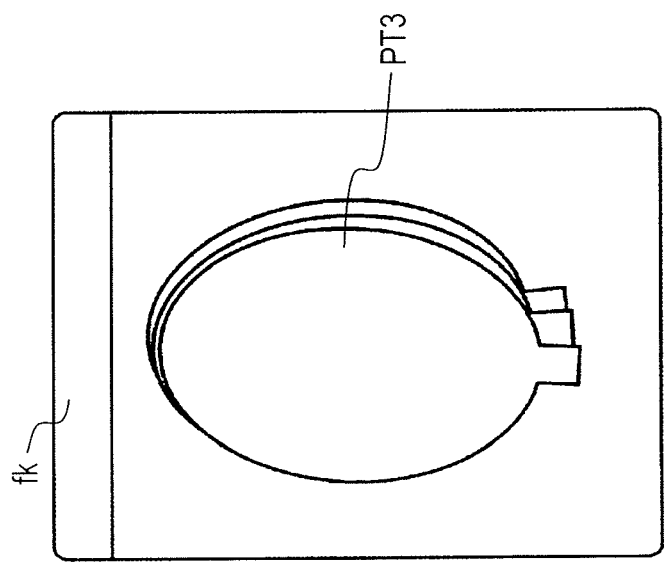

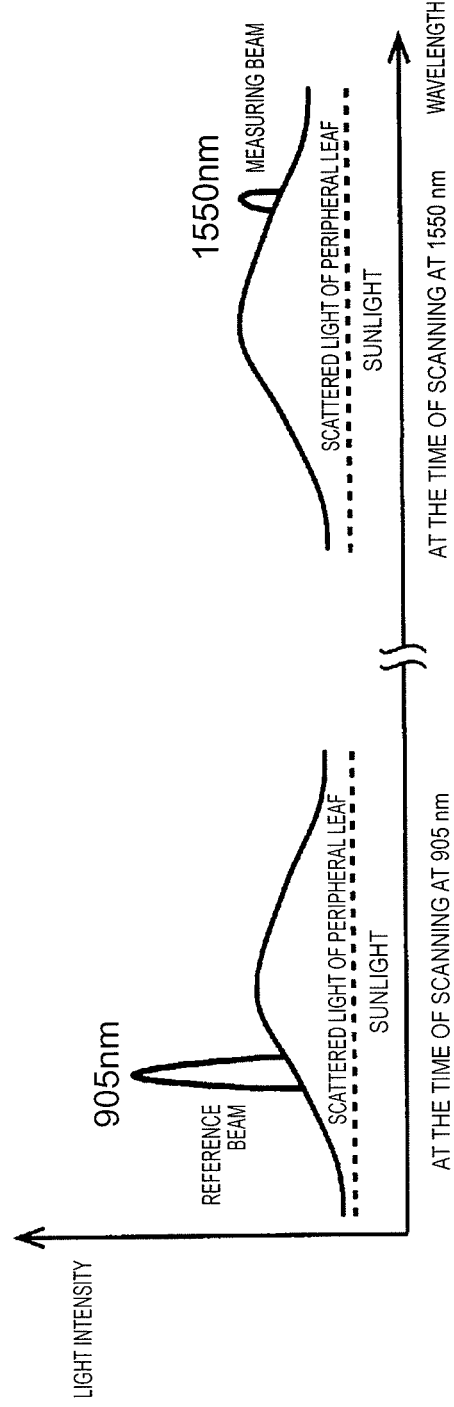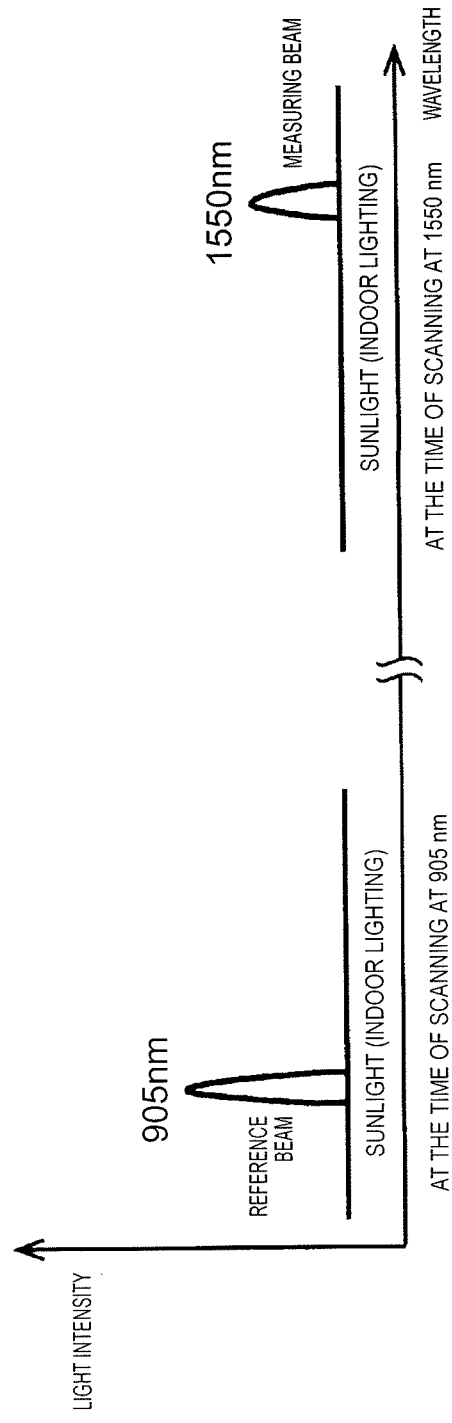

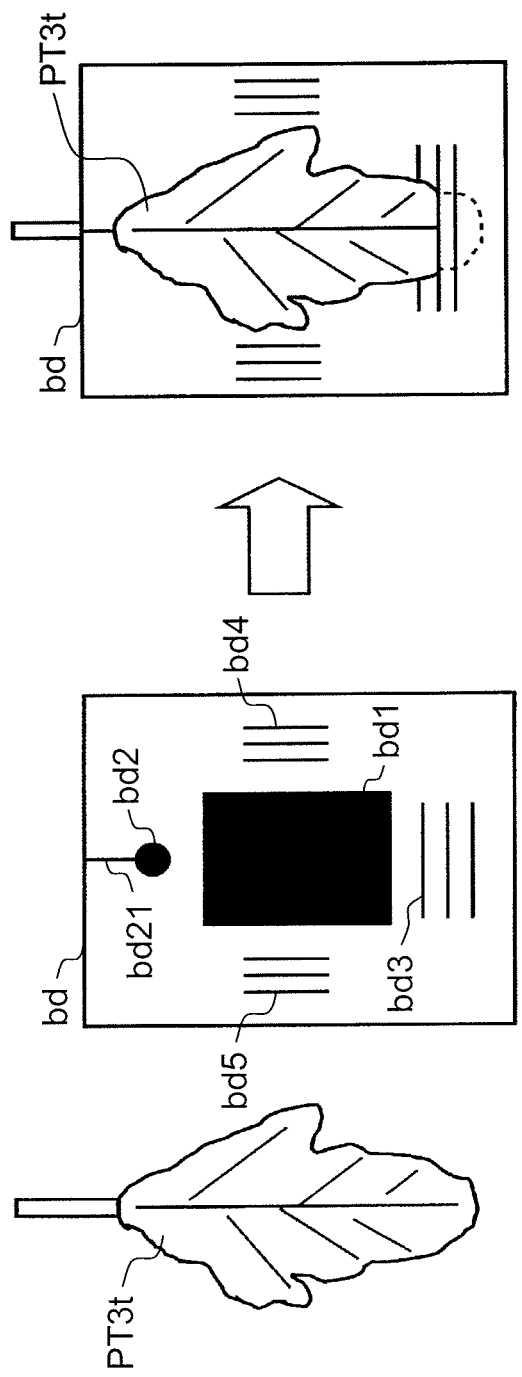

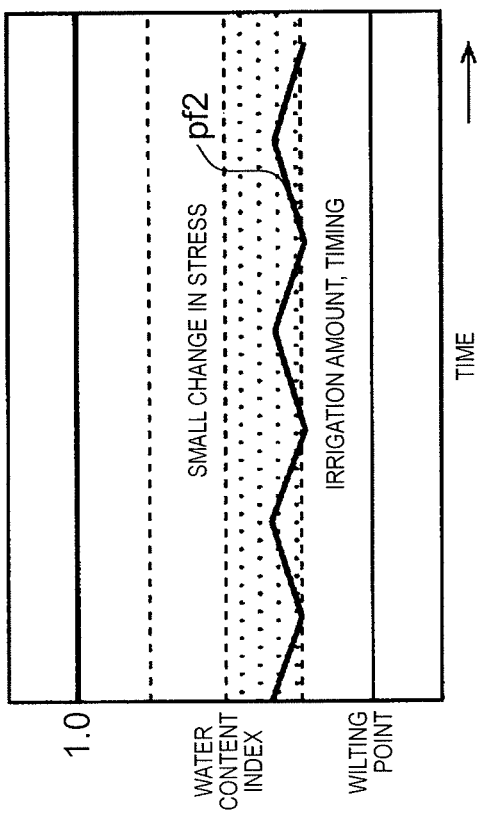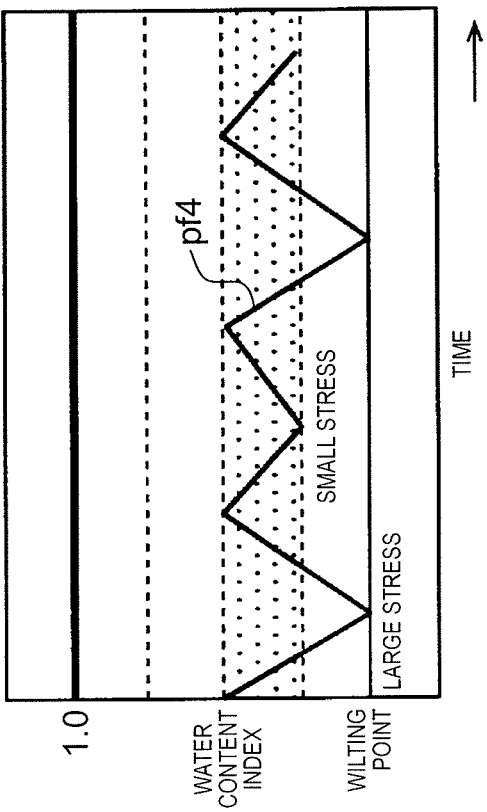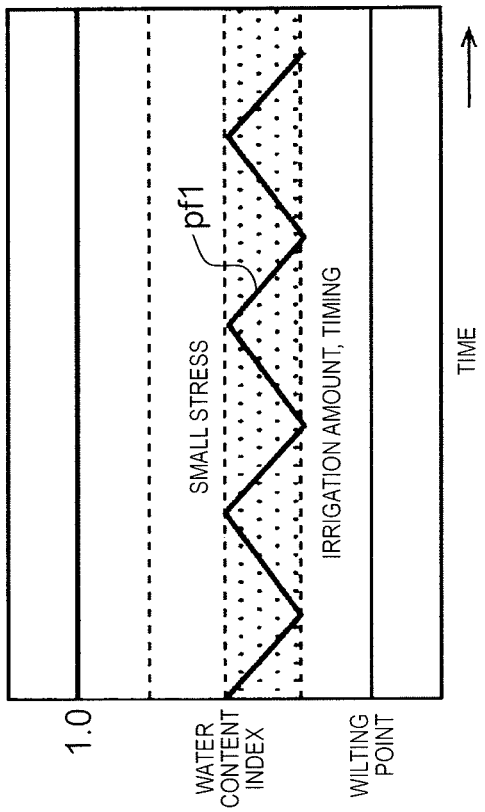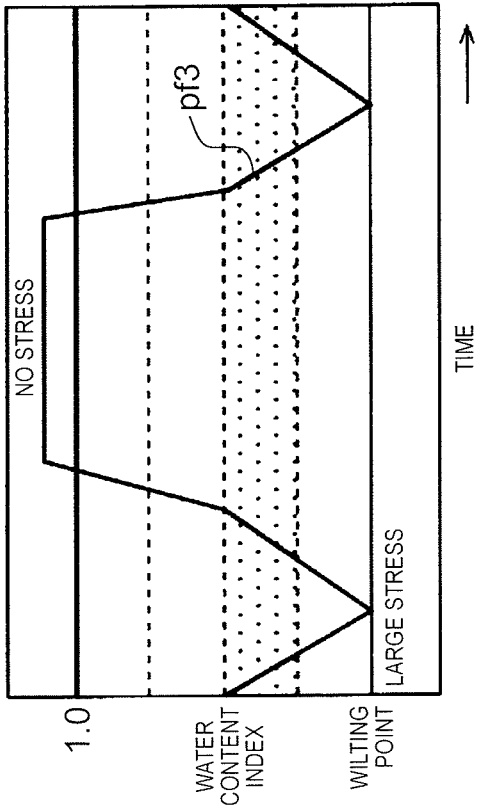

BEFORE POSITIONAL DEVIATION

AFTER POSITIONAL DEVIATION

FIG. 23

| TIME | ELAPSED TIME (MINUTE) | STANDARDIZED PIXEL AVERAGE WATER CONTENT INDEX | |
| --- | --- | --- | --- |
| | | BEFORE CORRECTION | AFTER CORRECTION |
| ⋮ | 15950 | 0.6879 | 0.6879 |
| | 15980 | 0.6586 | 0.6586 |
| | 16010 | 0.6639 | 0.6639 |
| | 16040 | 0.6674 | 0.6674 |
| | 16070 | 0.6650 | 0.6650 |
| | 16100 | 0.6593 | 0.6593 |
| | 16130 | 0.6425 | 0.6425 |
| | 16160 | 0.6503 | 0.6503 |
| | 16190 | 0.6530 | 0.6530 |
| | 16220 | 0.6416 | 0.6416 |
| 17:10 | 16250 | CORRECTION OF DEVIATION ↓ | |
| | 16280 | | |
| 18:40 | 16310 | 0.8785 | 0.6416 |
| | 16340 | 0.8694 | 0.6350 |
| | 16370 | 0.8444 | 0.6167 |
| | 16400 | 0.8515 | 0.6218 |
| ⋮ | 16430 | 0.8524 | 0.6225 |
| | 16460 | 0.8584 | 0.6269 |
| | 16490 | 0.8647 | 0.6315 |
| | 16520 | 0.8601 | 0.6281 |
| | 16550 | 0.8400 | 0.6135 |

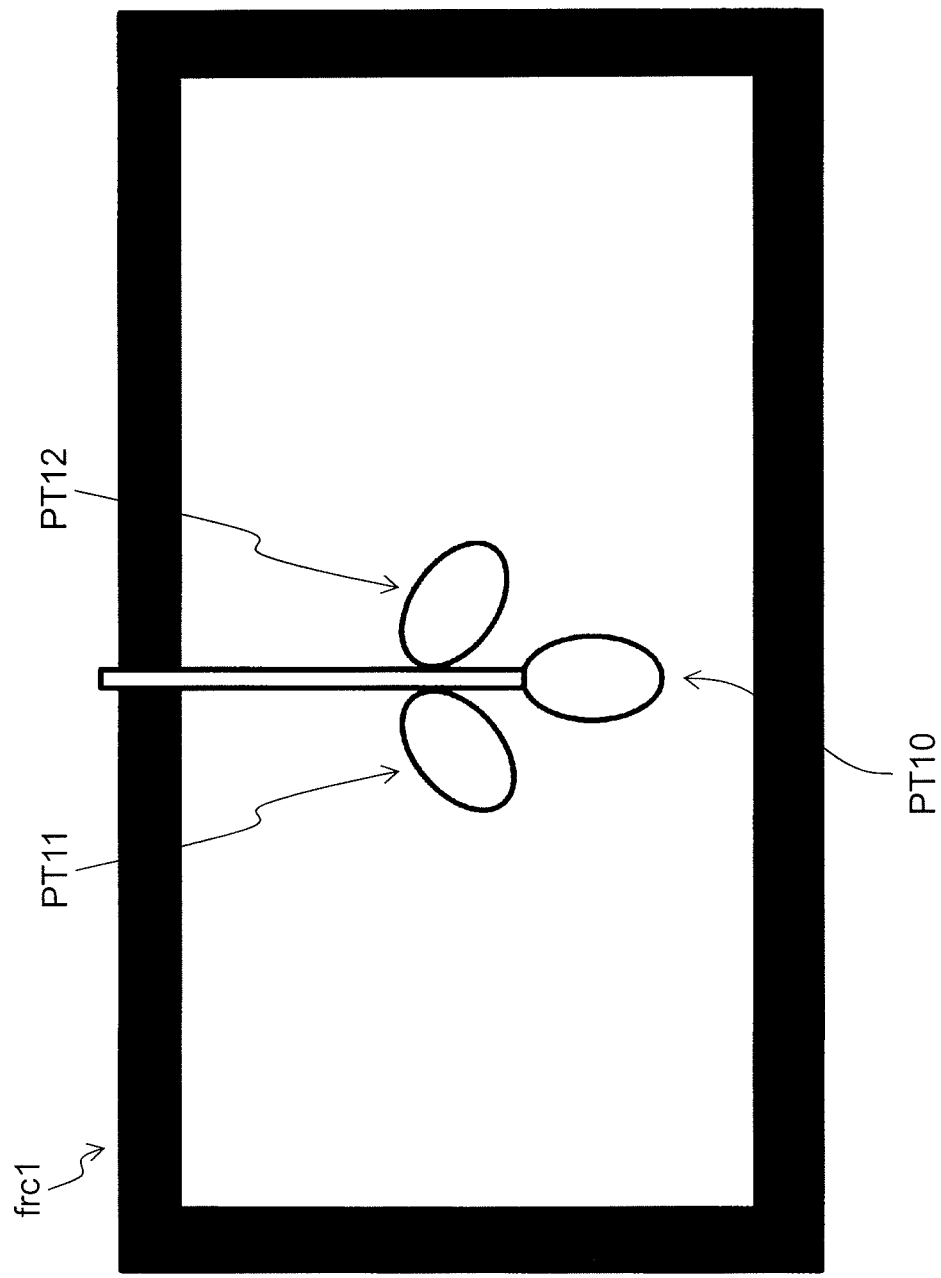

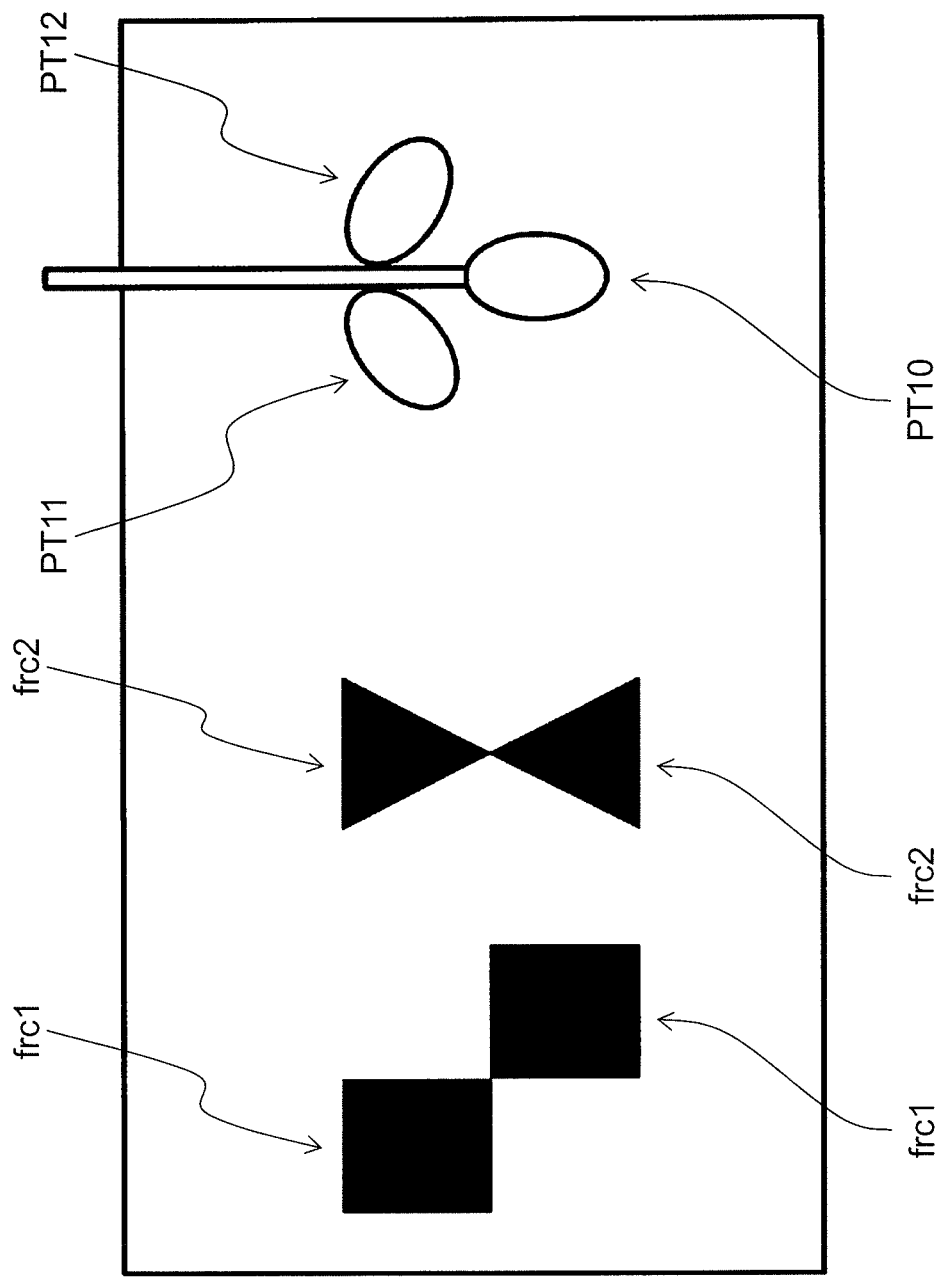
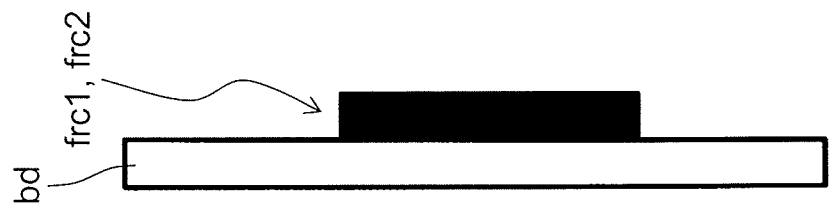

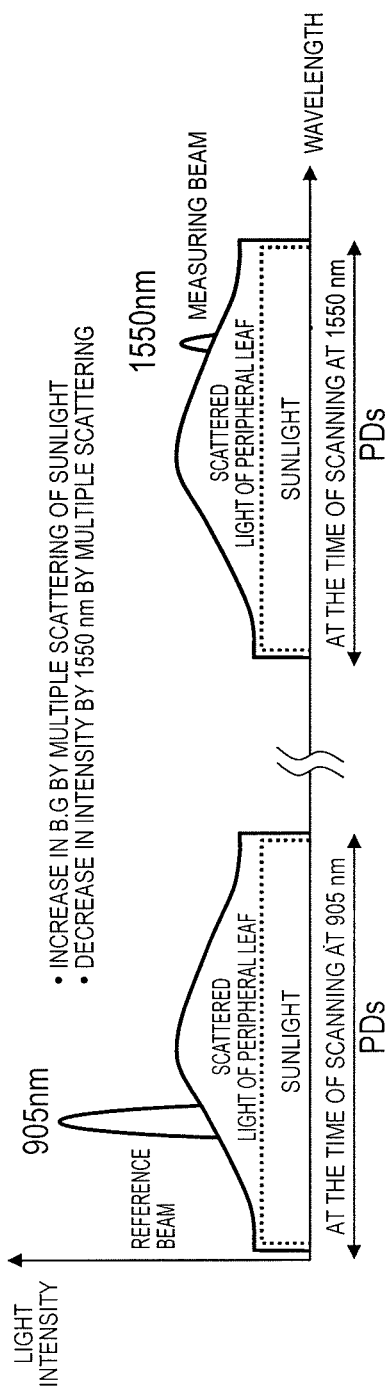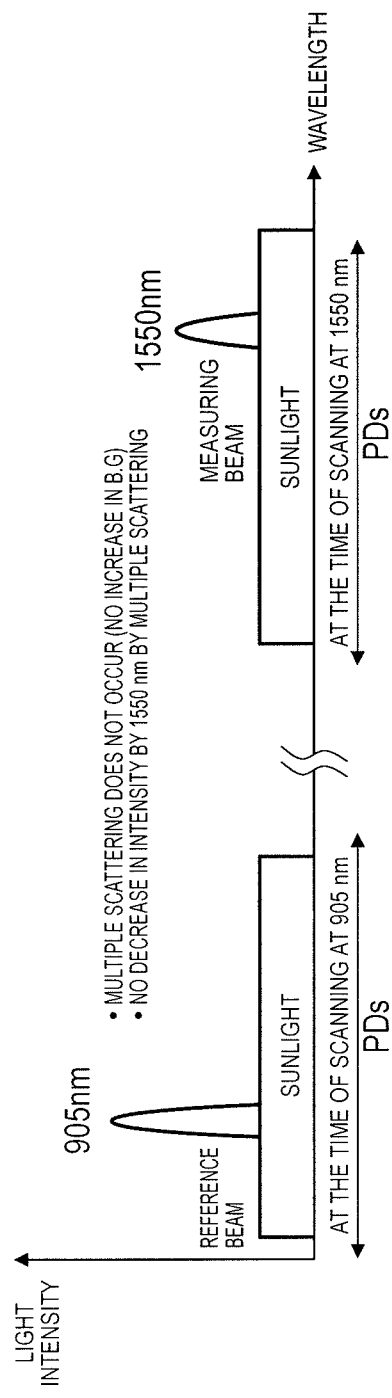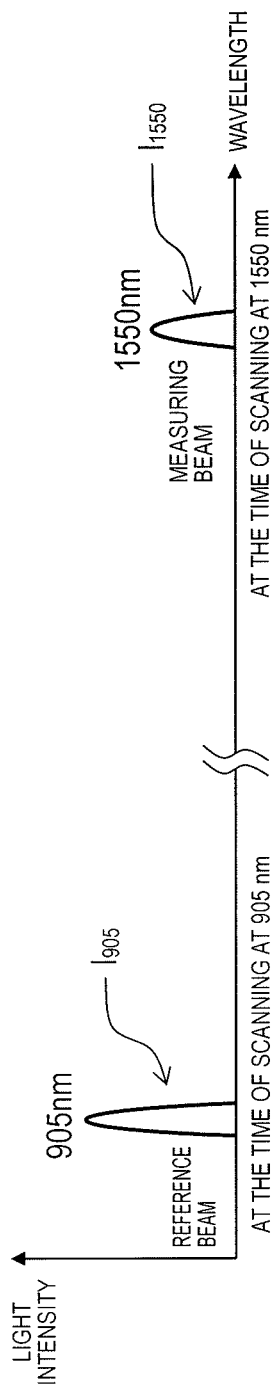
FIG. 43A
FIG. 43B
FIG. 43C

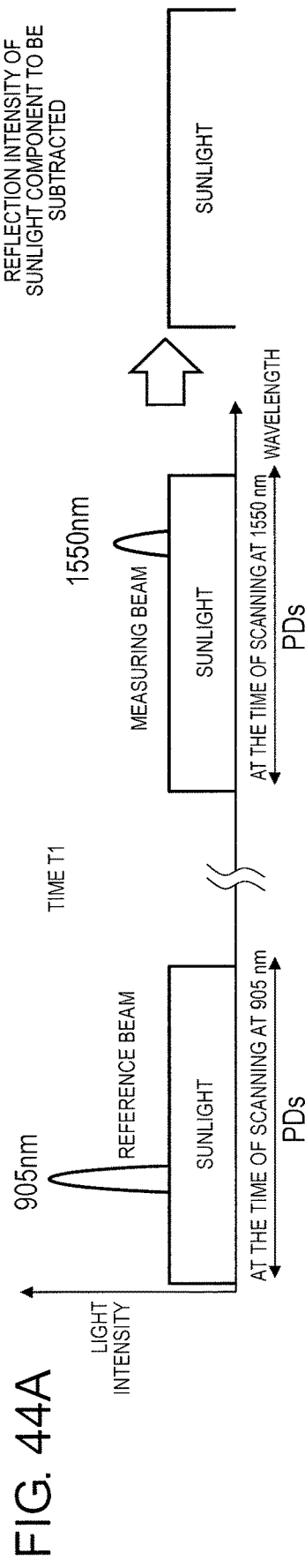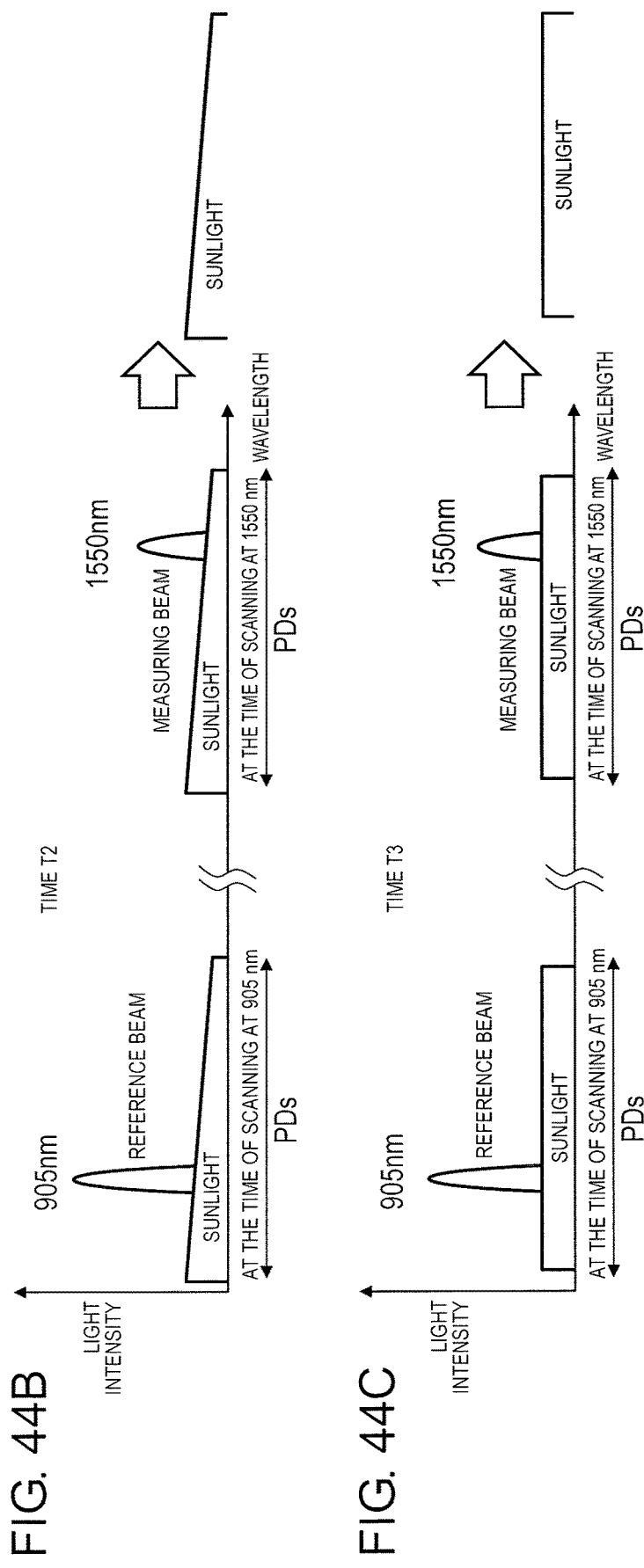
FIG. 44A
FIG. 44B
FIG. 44C

US 10,598,591 B2

MOISTURE CONTENT OBSERVATION DEVICE, MOISTURE CONTENT OBSERVATION METHOD, CULTIVATION DEVICE AND SAMPLE

TECHNICAL FIELD

The present disclosure relates to a device for observing water content which contained in a plant, a method for observing water content, and a cultivation device.

BACKGROUND ART

It is known that there is a potential difference inside and outside of a cell in a normal plant and electromotive force is generated. It is possible to describe a mechanism which generates such electromotive force based on, for example, an electrophysiological model of an axial organ of a higher plant. In particular, various methods are suggested in which a state of a root of the plant (for example, water stress) is examined non-destructively utilizing electromotive force between the root and soil.

As a prior technique in which water stress in a plant is measured utilizing the method described above, for example, Patent Document 1 is known. In Patent Document 1, connecting a first nonpolarizable electrode to the plant, connecting a second nonpolarizable electrode to soil in which the plant is planted, providing a potentiometer between the two nonpolarizable electrodes, and being able to measure water stress which is received by the plant by measuring electromotive force between both nonpolarizable electrodes using the potentiometer.

As for such parallax correction, a technology which performs parallax correction by acquiring a positional relationship of an image of a subject appearing in each captured image of two cameras by block matching based on edges and feature amounts, and deforming the image based on this information is known (refer to Patent Document 1). In particular, in this technique, a stitching point that defines the degree of deformation of the image at the time of the parallax correction is changed for each frame so as to generate an appropriate combined image for each frame.

Meanwhile, as an index for meaningfully measuring water content contained in a plant, for example, it is desired to quantitatively and visually suggest a time-transition of water stress in a growing process to an observer (for example, a user such as a farmer). In farms cultivating the plant (for example, vegetables such as tomatoes), in order to improve the value of tomato (that is, the unit price), for example, it is conceivable to improve the sugar content of tomatoes. Here, the kind of irrigation to be performed and the timing of the irrigation for increasing the sugar content is mainly attributable to artificial arrangements such as farmer's past experience and intuition. The amount of the water stress applied to the tomato is required to accurately predict to some extent in grasping irrigation timing so as to improve a sugar content of the tomato.

In general, increasing a sugar content of a fruit such as a tomato leads to quality improvement, and thus the unit price rises. On the other hand, since it is not easy to cultivate fruit such as tomato, yield is decreased and thereby production volume is decreased. In other words, there is a trade-off relationship between high performance of fruits and the yield. In the future, it is expected to increase the productivity by improving the yield.

An object of the present disclosure is to estimate water content contained in the plant by using an external standard sample has the same chemical properties as water, quantitatively and visually suggest a time-transition of the water content to a user, and early teach the timing of irrigation to the plant with high accuracy.

CITATION LIST

Patent Literature

PTL 1; Japanese Patent Unexamined Publication No. 2001-272373

SUMMARY OF THE INVENTION

A device for observing water content of the present disclosure is disposed facing a background material which covers back surfaces of an observation portion of a plant and at least one external sample having the same chemical properties as water contained in the observation portion of the plant, the device includes a first light source which radiates a reference beam having a characteristic in which light tends not to be absorbed in water while sequentially scanning toward the background material; a second light source which radiates a measuring beam having a characteristic in which light tends to be absorbed in water while sequentially scanning toward the background material; a water content derivation unit that derives the water content contained in the observation portion based on each reflection light of the reference beam reflected on the observation portion and the external sample and each reflection light of the measuring beam reflected on the observation portion and the external sample, in a certain measurement period; and a controller that displays a time-transition of the water content, which is contained in the observation portion during the measurement period, derived by the water content derivation unit on a display unit.

A device for observing water content of the present disclosure is disposed facing a background material which covers back surfaces of an observation portion of a plant and at least one external sample having the same chemical properties as water contained in the observation portion of the plant, the device includes a first light source which radiates a reference beam having a characteristic in which light tends not to be absorbed in water while sequentially scanning toward the background material; a second light source which radiates a measuring beam having a characteristic in which light tends to be absorbed in water while sequentially scanning toward the background material; a water content derivation unit that derives the water content contained in the observation portion based on each reflection light of the reference beam reflected on the observation portion and the external sample and each reflection light of the measuring beam reflected on the observation portion and the external sample, in a certain measurement period; and a controller that displays a time-transition of the water content, which is contained in the observation portion during the measurement period, derived by the water content derivation unit on a display unit, in which the controller controls irradiation timing of the reference beam and the measuring beam so as to provide a non-irradiation period between an irradiation cycle of the reference beam and an irradiation cycle of the measuring beam, and the water content derivation unit subtracts the same wavelength component as the reference beam of sunlight received in the non-irradiation period from the reflection light of the reference beam reflected on the observing portion, subtracts the same wavelength component as the measuring beam of the sunlight received in the non-irradiation period from the reflection light of the measuring beam reflected on the observing portion, and derives the water content contained in the observation portion based on each reflection light after subtraction.

The cultivation device of the present disclosure is provided with the device for observing water content, and a cultivation controller that irrigates the plant with a predetermined amount of water based on the time-transition of the water content calculated by the water content derivation unit in a certain period of the measurement periods.

In addition, according to the present disclosure, a method for observing water content in a device including a first light source and a second light source, the method includes, disposing the device for observing water content of the present disclosure to face a background material which covers back surfaces of an observation portion of a plant and at least one external sample having the same chemical properties as water contained in the observation portion of the plant, radiating a reference beam having a characteristic in which light tends not to be absorbed in water while sequentially scanning toward the background material, by a first light source which; radiating a measuring beam having a characteristic in which light tends to be absorbed in water while sequentially scanning toward the background material, by a second light source; deriving the water content contained in the observation portion based on each reflection light of the reference beam reflected on the observation portion and the external sample and each reflection light of the measuring beam reflected on the observation portion and the external sample, in a certain measurement period on a display unit; and displaying a time-transition of the water content contained in the measurement period.

According to the present disclosure, it is possible to estimate water content contained in the plant by using an external standard sample having the same chemical properties as water, quantitatively and visually suggest a time-transition of the water content to a user, and early teach the timing of irrigation to the plant with high accuracy.

BRIEF DESCRIPTION OF DRAWINGS

FIG. 9 is a diagram illustrating an example of the method of measuring Comparative Examples.

FIG. 10A is a graph illustrating an example of the reflection light intensity with respect to wavelength of the near infrared beam when near infrared beam is radiated toward the leaf outdoors.

FIG. 10B is a graph illustrating an example of the reflection light intensity with respect to wavelength of the near infrared beam when near infrared beam is radiated toward the leaf on which white reference substrate bd is installed indoors and outdoors.

FIG. 11 is a diagram which describes an example of attachment of the leaf on a white reference substrate.

FIG. 19A is a graph schematically illustrating an example of a water stress profile.

FIG. 19B is a graph schematically illustrating an example of a water stress profile.

FIG. 19C is a graph schematically illustrating an example of a water stress profile.

FIG. 19D is a graph schematically illustrating an example of a water stress profile.

FIG. 23 is a diagram illustrating a table indicating an example of the standardized pixel average water content index before and after positional deviation correction in time series.

FIG. 41A is a diagram illustrating a first modification example of attachment with respect to the white reference substrate of the true leaf and the artificial leaf.

FIG. 41B is a diagram illustrating a first modification example of attachment with respect to the white reference substrate of the true leaf and the artificial leaf.

FIG. 42A is a diagram illustrating a second modification example of attachment with respect to the white reference substrate of the true leaf and the artificial leaf.

FIG. 42B is a diagram illustrating a second modification example of attachment with respect to the white reference substrate of the true leaf and the artificial leaf.

FIG. 43A is a graph illustrating an example of the intensity of the reflection light with respect to each wavelength of the near infrared laser beam when irradiated with the near infrared laser beam of 905 nm and 1550 nm toward the true leaf outdoors.

FIG. 43B is a graph illustrating an example of the intensity of the reflection light with respect to each wavelength of the near infrared laser beam when irradiated with the near infrared laser beam of 905 nm and 1550 nm toward the true leaf on white reference substrate bd installed outdoors.

FIG. 43C is a graph illustrating an example of the intensity of the reflection light for each of near infrared laser beam of 905 nm and 1550 nm which is originally necessary for accurately calculating the water content of the true leaf.

FIG. 44A is a graph illustrating an example of a change of a rise of background of the intensity of the reflection light based on the influence of sunlight at time T1 when the white reference substrate is installed outdoor.

FIG. 44B is a graph illustrating an example of a change of a rise of background of the intensity of the reflection light based on the influence of sunlight at time T2 when the white reference substrate is installed outdoor.

FIG. 44C is a graph illustrating an example of a change of a rise of background of the intensity of the reflection light based on the influence of sunlight at time T3 when the white reference substrate is installed outdoor.

DESCRIPTION OF EMBODIMENTS

Hereinafter, embodiments in which a device for observing water content, a cultivation device, and a method for observing water content according to the present disclosure are specifically described are described in detail with reference to the drawings as appropriate. However, detailed description may be omitted as necessary. For example, detailed description of already well-known matter and overlapping description with respect to substantially the same configuration may be omitted. This because the following description is prevented from unnecessarily becoming redundant, and a process of the inventor is easily set. Note that, drawings and the following description are provided by the inventor for sufficient understanding of the present disclosure, and thereby, the present disclosure is not intended to be limited to a subject described in the range of the claims.

First Embodiment

Figure 1:
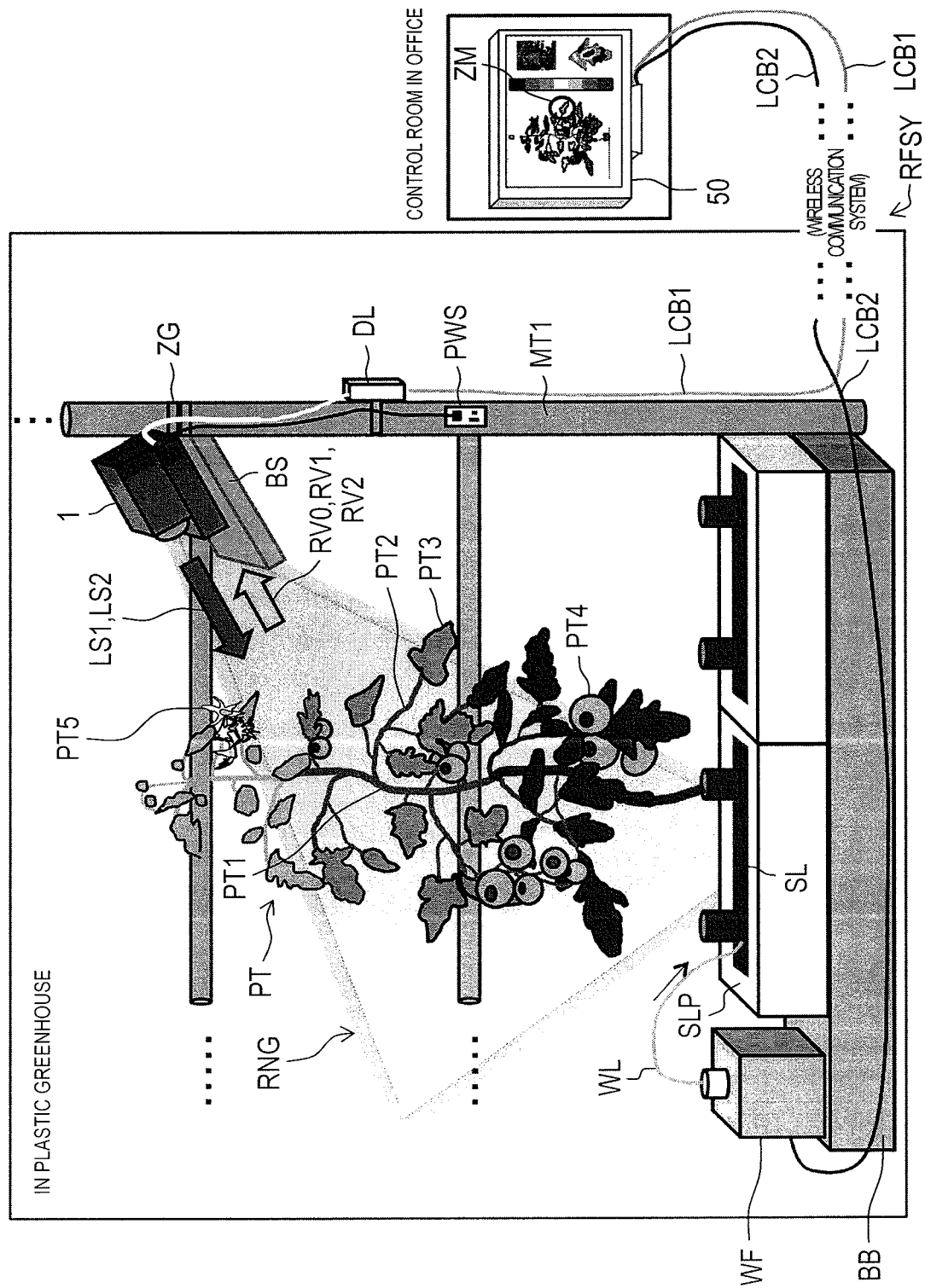
FIG. 1 is a conceptual explanatory diagram illustrating an example of usage circumstances of a plant detection camera in a first embodiment.

As an example of the device for observing water content of the present embodiment, description will be given by exemplifying plant detection camera 1 as illustrated in FIG. 1. In addition, the cultivation device of the present embodiment has a configuration of including plant detection camera 1 as illustrated in FIG. 1, fertilizer or water supply device WF as an example of a cultivation controller that supplies a fertilizer (for example, a liquid fertilizer) or irrigates the plant with a predetermined amount of the water content, and monitor 50 as a display unit that displays (user Interface) screen 60 (refer to FIG. 16) or the like. Further, the present disclosure can realize a method for observing water content for executing each process performed by plant detection camera 1. Plant detection camera 1 of the present embodiment is able to detect a distribution state of presence or absence of water content of the leaf or the part of the plant.

Here, an observation target of plant detection camera 1 of the present embodiment is the leaf or the part of the plant, and description is made by exemplifying a fruit vegetable that is given as a more specific example. Since sugar content of a fruit of a tomato is increased in growth of fruit vegetables such as, for example, the tomato, it is known that it is necessary for water or fertilizer to be in an insufficient state and not a state in which water or fertilizer is sufficiently supplied as a result of water or fertilizer of a root or a leaf being digested by a suitable amount in photosynthesis. For example, if sufficient water is supplied to the leaf, the leaf has a flat shape in a sound state. Meanwhile, when water of the leaf is equivalently insufficient, the shape of the leaf is bent. Meanwhile, when fertilizer in the soil is equivalently insufficient, a condition is generated of the leaf turning yellow and the like.

In the present embodiment below, plant detection camera 1 radiates near infrared laser beams of a plurality of types which are different in wavelength on the plant (for example leaf), and detects water content of the leaf based on an intensity ratio of respective diffuse reflection light that are reflected on irradiation positions of the leaf. Note that, in the present embodiment, the leaf of the plant is the measurement target, but the measurement target is not limited to the leaf, and may be other parts of a seed, stalk, flower, and the like. This also applies to the second and subsequent embodiments.

(Outline of Plant Detection Camera)

FIG. 1 is a conceptual explanatory diagram illustrating an example of usage circumstances of plant detection camera 1 in a first embodiment; Plant detection camera 1 is installed at a fixed point within a greenhouse in which, for example, fruit vegetables such as the tomato are planted. In detail, for example, plant detection camera 1 is installed on base BS that is fixed to mounting jig ZG which is attached so as to interpose support column MT1 with a cylindrical shape extend in a vertical direction from the ground. Plant detection camera 1 operates by a power source to be supplied from power source switch PWS that is attached to support column MT1, and radiates reference beam LS1 and measuring beam LS2 that are a plurality of types of laser beams which have different wavelengths toward plant PT that is the observation target across irradiation range RNG.

Plant PT is, for example, a fruit vegetable plant such as the tomato, a root of plant PT which grows from soil SL that is filled in soil pot SLP which is installed on base BB, and plant PT has each of stalk PT1, stalk PT2, leaf PT3, fruit PT4, and flower PT5. Fertilizer or water supply device WF is installed on base BB. Fertilizer or water supply device WF supplies water to soil spot SLP via, for example, cable WL according to an instruction from wireless communication system RFSY that is connected via local area network (LAN) cable LCB2. Thereby, since water is supplied to soil SL, the root of plant PT absorbs water, and transmits water to each part within plant PT (that is, stalk PT1, stalk PT2, leaf PT3, fruit PT4, and flower PT5).

In addition, plant detection camera 1 receives diffuse reflection light RV1 and RV2 that are reflected on an irradiation position of plant PT which is radiated by reference beam LS1 and measuring beam LS2, and furthermore, receives ambient light RV0. As will be described later, plant detection camera 1 may also have a normal camera function, and is able to image an image (that is, visible light image of plant PT within the greenhouse indicated in FIG. 1) within a default angle of view due to ambient light RV0 entering. Plant detection camera 1 outputs output data which includes various detection results (refer to description below) or image data to data logger DL based on diffuse reflection light RV1 and RV2.

Data logger DL transmits output data from plant detection camera 1 to management personal computer (PC) of a control room within an office at a position geographically separated from the greenhouse via LAN cable LCB1 and wireless communication system RFSY. Wireless communication system RFSY is not particularly limited in communication specification, but controls communication between data logger DL within the greenhouse and management PC within the control room in the office, and furthermore transmits an instruction from management PC which relates to supply of water or fertilizer of soil spot SLP to fertilizer or water supply device WF.

Monitor 50 is connected to management PC within the control room in the office, and management PC displays output data of plant detection camera 1 that is transmitted from data logger DL on monitor 50. In FIG. 1, for example, monitor 50 displays the entirety of plant PT that is the observation target and a distribution state which relates to presence or absence of water in the entirety of plant PT. In addition, monitor 50 generates and is able to comparatively display an enlargement distribution state of a specific designated location out of the entirety of plant PT (that is, designated location ZM that is specified by a zoom operation of an observer who uses management PC) and image data corresponding to the designated location of the enlargement distribution state. Further, monitor 50, which is an example of the display unit, displays UI screen 60 including screen for monitoring water content in leaf Gm1 (refer to FIG. 16) described later.

Plant detection camera 1 may be configured to include, for example, invisible light sensor NVSS or may be configured to include visible light camera VSC and invisible light sensor NVSS. Here, a case where plant detection camera 1 includes both visible light camera VSC and invisible light sensor NVSS will be described. Visible light camera VSC (acquiring unit) images plant PT within the greenhouse using ambient light RV0 with respect to visible light that has a predetermined wavelength (for example, 0.4 to 0.7 μm) in the same manner as, for example, existing monitoring camera. Image data of the plant that is imaged by visible light camera VSC refers to "visible light camera image data".

Invisible light sensor NVSS incidents reference beam LS1 and measuring beam LS2 which is invisible light (for example, infrared beam) that has a plurality of types of wavelengths (refer to description below) with respect to the same plant PT as invisible light camera VSC. Invisible light sensor NVSS detects presence or absence of water at the irradiation position of plant PT which is the observation target using the intensity ratio of diffuse reflection light RV1 and RV2 that are reflected on the irradiation position of plant PT which is radiated by reference beam LS1 and measuring beam LS2.

In addition, in visible light camera image data that is imaged by visible light camera VSC, plant detection camera 1 generates and outputs output image data (hereinafter referred to as "detection result image data") which is equivalent to the detection result of water of invisible light sensor NVSS or display data that composites information which relates to detection result image data. Display data is not limited to image data in which detection result image data and visible light camera image data are composited, and for example, may be image data that is generated such that detection result image data and visible light camera image data are able to be compared. An output destination of the display data from plant detection camera 1 is an externally connected device that is connected to plant detection camera 1 via, for example, a network, and is data logger DL or communication terminal MT (refer to FIG. 2). The network may be a wired network (for example, intranet or internet), and may be a wireless network (for example, wireless LAN).

(Description of Each Part of Plant Detection Camera)

Figure 2:
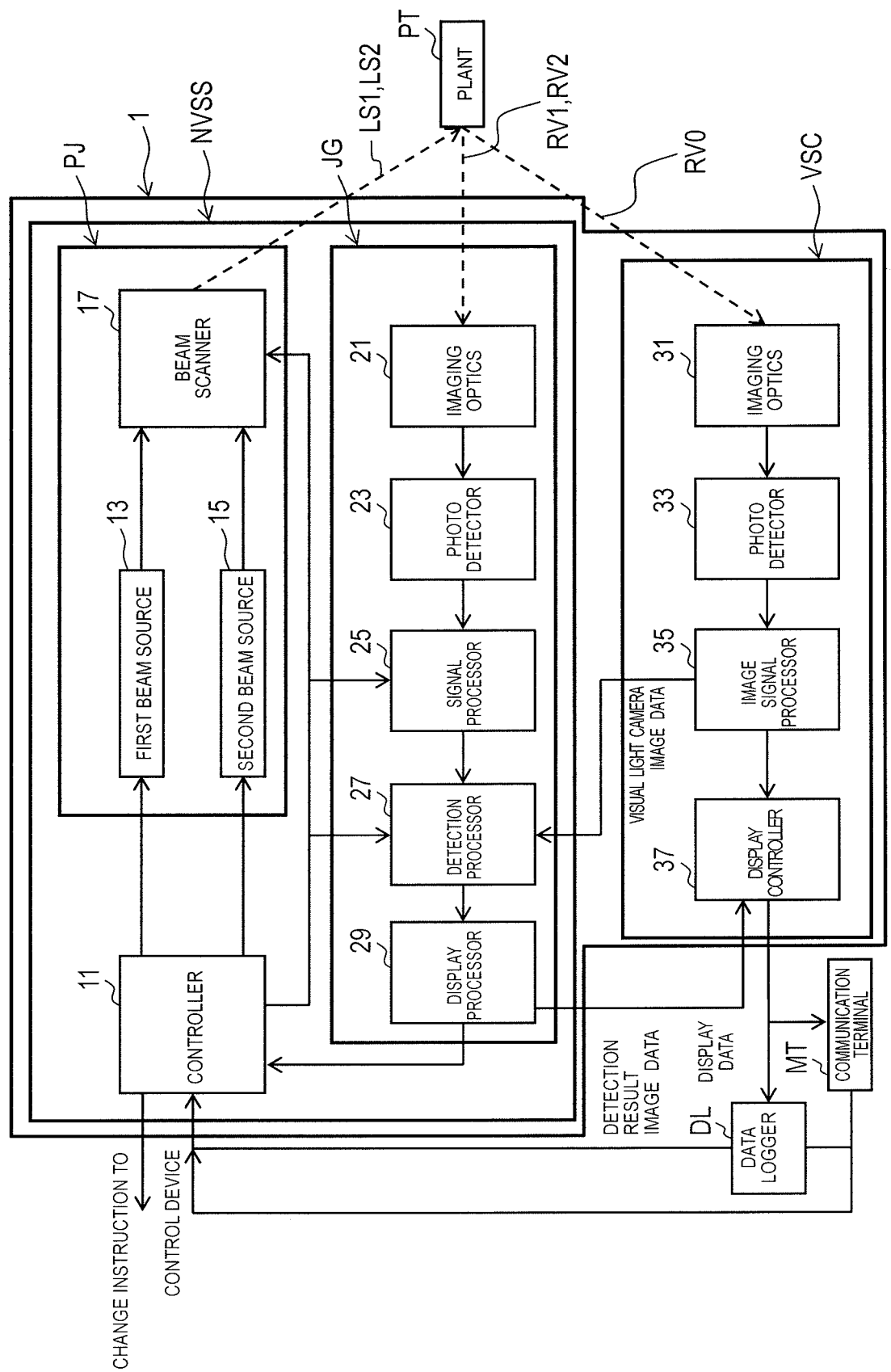
FIG. 2 is a block diagram illustrating in detail an example of an internal configuration of the plant detection camera.

FIG. 2 is a block diagram illustrating in detail an example of an internal configuration of plant detection camera 1. Plant detection camera 1 which is illustrated in FIG. 2 has a configuration which includes invisible light sensor NVSS and visible light camera VSC. Invisible light sensor NVSS has a configuration which includes controller 11, beam output PJ, and determiner JG. Beam output PJ has first beam source 13, second beam source 15, and beam scanner 17. Determiner JG has imaging optics 21, photo detector 23, signal processor 25, detection processor 27, and display processor 29. Visible light camera VSC has imaging optics 31, photo detector 33, image signal processor 35, and display controller 37. Communication terminal MT is portable by a user (for example, observer of growth of plant PT of fruit vegetable plant such as the tomato, hereinafter the same).

In the description of each part of plant detection camera 1, controller 11, invisible light sensor NVSS, and visible light camera VSC are described in order.

Controller 11 is configured using, for example, a central processor (CPU), a microprocessor (MPU), or a digital signal processor (DSP), (and also configured using, for example, a program memory and a work memory) and performs a signal process for totally controlling an operation control of each part of visible light camera VSC and invisible light sensor NVSS, an input and output process of data within other parts, a computing process of data, and a storage process of data. In addition, controller 11 includes timing controller 11a described later (refer to FIG. 3).

Controller 11 sets detection threshold level M of plant PT which is the detection target of invisible light sensor NVSS to detection processor 27 described later. Details of the operation of controller 11 will be described later with reference to FIG. 4.

Timing controller 11a controls output timing of first beam source 13 and second beam source 15 in beam output PJ. In detail, timing controller 11a outputs timing signal for beam scanning TR to first beam source 13 and second beam source 15 in a case where light is incident to first beam source 13 and second beam source 15.

In addition, during the start of a predetermined incidence period, timing controller 11a alternately outputs beam output signal RF to first beam source 13 or second beam source 15. In detail, during the start of the incidence period of an odd number of times, timing controller 11a outputs beam output signal RF to first beam source 13 and during the start of the incidence period of an even number of times, outputs beam output signal RF to second beam source 15.

Next, each part of invisible light sensor NVSS is described.

When first beam source 13 as an example of the first light source receives timing signal for beam scanning TR from timing controller 11a of controller 11, reference beam LS1 (for example, near infrared beam) that is a laser beam of invisible light that has a predetermined wavelength (for example, 905 nm) is incident on plant PT via beam scanner 17 according to beam output signal RF from timing controller 11a in each incidence period (default value) of an odd number of times.

Note that, presence or absence of detection of water in plant PT may be determined by comparing to the predetermined detection threshold level M. Detection threshold level M may be a predetermined value, may be an arbitrarily set value, and furthermore, may be a value based on intensity of the diffuse reflection light that is acquired in a state in which there is no water (for example, a value in which a predetermined margin is added to a value of intensity of the diffuse reflection light that is acquired in a state in which there is no water). That is, presence or absence of detection of water may be determined by comparing detection result image data that is acquired in a state in which there is no water and detection result image data that is acquired thereafter. In this manner, it is possible to set a threshold level appropriate for an environment in which plant detection camera 1 is installed as detecting threshold level M of presence or absence of water by acquiring intensity of the diffuse reflection light in the state in which there is no water.

When second beam source 15 as an example of the second light source receives timing signal for beam scanning TR from timing controller 11a of controller 11, measuring beam LS2 (for example, infrared beam) that is the laser beam of invisible light that has a predetermined wavelength (for example, 1550 nm) is incident on plant PT via beam scanner 17 according to beam output signal RF from timing controller 11a in each incidence period (default value) of an even number of times. In the present embodiment, measuring beam LS2 that is incident from second beam source 15 is used in determination of presence or absence of detection of water in plant PT. Wavelength 1550 nm of measuring beam LS2 is a wavelength which has a characteristic in which light tends to be absorbed in water (refer to FIG. 6).

Furthermore, plant detection camera 1 detects presence or absence of water at the irradiation position of plant PT that is radiated by reference beam LS1 and measuring beam LS2 using diffuse reflection light RV1 of reference beam LS1 as reference data for detecting water at the irradiation position of plant PT, and using diffuse reflection light RV2 at the irradiation position of plant PT that is radiated by measuring beam LS2 and diffuse reflection light RV1 of reference beam LS1. Accordingly, plant detection camera 1 is able to detect water of plant PT with high precision using reference beam LS1 and measuring beam LS2 of two types of wavelengths that detect water in plant PT differently and diffuse reflection lights RV1 and RV2 thereof.

Beam scanner 17 two-dimensionally scans reference beam LS1 which is incident from first beam source 13 and measuring beam LS2 which is incident from second beam source 15 with respect to plant PT that is present in a detection area in invisible light sensor NVSS. Thereby, plant detection camera 1 detects presence or absence of water at the irradiation position of plant PT that is radiated by reference beam LS1 and measuring beam LS2 based on diffuse reflection light RV2 that is reflected at the irradiation position of plant PT by measuring beam LS2 and diffuse reflection light RV1 described above.

Figure 3:
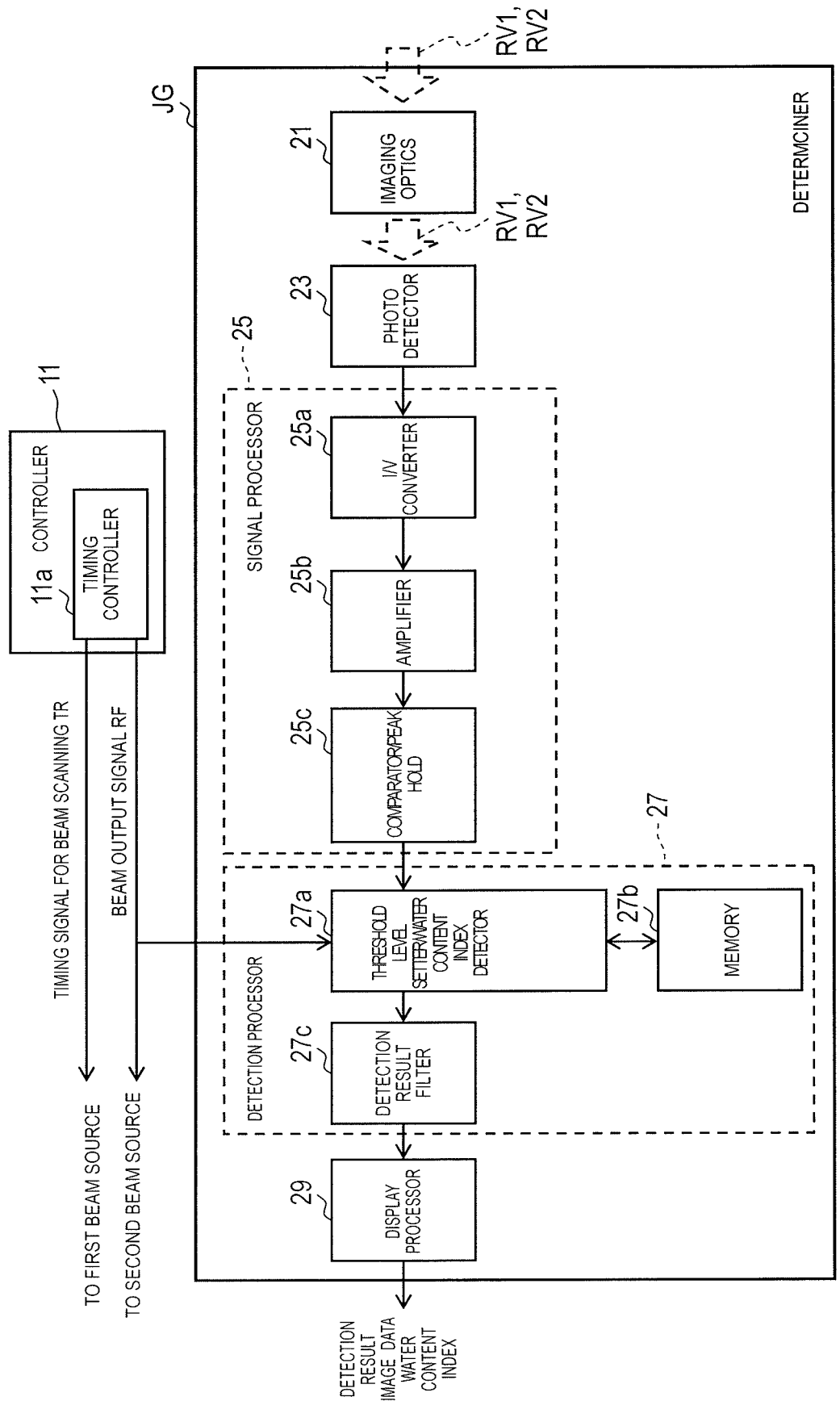
FIG. 3 is a diagram illustrating in detail an example of an internal configuration of a determiner of the plant detection camera.

Next, an internal configuration of determiner JG is described in detail with reference to FIGS. 2 and 3. FIG. 3 is a diagram illustrating in detail an example of an internal configuration of a determiner JG of plant detection camera 1.

Imaging optics 21 is configured using, for example, a lens, light (for example, diffuse reflection light RV1 or diffuse reflection light RV2) which is incident from outside of plant detection camera 1 is concentrated, and diffuse reflection light RV1 or diffuse reflection light RV2 form an image on a predetermined imaging area of photo detector 23.

Photo detector 23 is an image sensor which has a peak of spectral sensitivity with respect to wavelengths of both of reference beam LS1 and measuring beam LS2. Photo detector 23 converts an optical image of diffuse reflection light RV1 or diffuse reflection light RV2 that form an image on the imaging area to an electrical signal. Output of photo detector 23 is input to signal processor 25 as the electrical signal (current signal). Note that, imaging optics 21 and photo detector 23 functions as an imaging unit in invisible light sensor NVSS.

Signal processor 25 has I/V converter 25a, amplifier 25b, and comparator/peak hold 25c. I/V converter 25a converts the current signal that is an output signal (analog signal) of photo detector 23 to a voltage signal. Amplifier 25b amplifies a level of the voltage signal that is the output signal (analog signal) of I/V converter 25a up to a processable level in comparator/peak hold 25c.

Comparator/peak hold 25c binarizes the output signal of amplifier 25b and outputs to threshold level setter/water content index detector 27a according to a comparative result of the output signal (analog signal) of amplifier 25b and the predetermined threshold level. In addition, comparator/peak hold 25c includes an analog digital converter (ADC), detects and holds the peak of an analog digital (AD) converter result of the output signal (analog signal) of amplifier 25b and furthermore, outputs peak information to threshold level setter/water content index detector 27a.

Detection processor 27 has threshold level setter/water content index detector 27a, memory 27b, and detection result filter 27c. Threshold level setter/water content index detector 27a (an example of threshold holding unit) generates and registers frequency distribution data in advance. Frequency distribution data indicates frequency distribution of the reflection intensity ratio (water content index) in all pixels or one frame image. As will be described later, threshold level setter/water content index detector 27a (threshold level calculation unit) is set by calculating threshold level Sh of the reflection intensity ratio for identifying the shape of the leaf using the frequency distribution data.

In addition, threshold level setter/water content index detector 27a detects presence or absence of water at the irradiation position of reference beam LS1 and measuring beam LS2 of plant PT based on output (peak information) of comparator/peak hold 25c in diffuse reflection light RV1 of reference beam LS1 and output (peak information) of comparator/peak hold 25c in diffuse reflection light RV2 of measuring beam LS2.

In detail, threshold level setter/water content index detector 27a temporarily stores, for example, output (peak information) of comparator/peak hold 25c in diffuse reflection light RV1 of reference beam LS1 in memory 27b, and next, waits until the output (peak information) of comparator/peak hold 25c in diffuse reflection light RV2 of measuring beam LS2 is obtained. Threshold level setter/water content index detector 27a obtains output (peak information) of comparator/peak hold 25c in diffuse reflection light RV2 of measuring beam LS2, and then calculates a ratio of output (peak information) of comparator/peak hold 25c in diffuse reflection light RV1 of reference beam LS1 and output (peak information) of comparator/peak hold 25c in diffuse reflection light RV2 of measuring beam LS2 in the same line of plant PT that are contained in the angle of view with reference to memory 27b.

For example, at the irradiation position at which there is water, since a portion of measuring beam LS2 tends to be absorbed, intensity (that is, amplitude) of diffuse reflection light RV2 is attenuated. Accordingly, it is possible for threshold level setter/water content index detector 27a to detect presence or absence of water at the irradiation position of reference beam LS1 and measuring beam LS2 based on a calculation result (for example, calculation result of difference (difference ΔV of amplitude) of each intensity of diffuse reflection light RV1 and diffuse reflection light RV2 or intensity ratio of diffuse reflection light RV1 and diffuse reflection light RV2) of each line of plant PT which is contained in the angle of view.

Note that, threshold level setter/water content index detector 27a may detect presence or absence of water at the irradiation position of reference beam LS1 and measuring beam LS2 of plant PT (refer to FIG. 5) according to a comparison of the size of rate RT of amplitude difference between amplitude VA of diffuse reflection light RV1 of reference beam LS1 and amplitude VB of diffuse reflection light RV2 of measuring beam LS2 (VA−VB) and amplitude VA with predetermined detection threshold level M.

Further, threshold level setter/water content index detector 27a calculates the intensity ratio of diffuse reflection light RV1 to diffuse reflection light RV2, that is, the reflection intensity ratio (also referred to as measurement value) Ln $(I_{905}/I_{1550})$, and obtains a total sum of the water content index corresponding to the water content contained in the leaf from the total sum of reflection intensity ratio Ln $(I_{905}/I_{1550})$. Reflection intensity ratio Ln $(I_{905}/I_{1550})$ is, for example, calculated by a predetermined pixel number (4×4 pixels) in all pixels in one frame image captured by visible light camera VSC, and is expressed as reflection intensity rate W1 to Wk in each predetermined pixel number.

Memory 27b is configured using, for example, a random access memory (RAM), and temporarily stores output (peak information) of comparator/peak hold 25c in diffuse reflection light RV1 of reference beam LS1.

Detection result filter 27c filters and then extracts information which relates to detection result of water from plant detection camera 1 based on output of threshold level setter/water content index detector 27a. Detection result filter 27c outputs information which relates to the detection result to display processor 29. For example, detection result filter 27c outputs information which relates to the detection result of water at the irradiation position of reference beam LS1 and measuring beam LS2 of plant PT to display processor 29.

Display processor 29 uses output of detection result filter 27c and generates data of detection result image that indicates the position of water at the irradiation position at each distance from plant detection camera 1 as an example of information which relates to water at the irradiation position. Display processor 29 outputs detection result image data which includes information on distance from plant detection camera 1 to the irradiation position to display controller 37 of visible light camera VSC.

Next, each part of visible light camera VSC will be described. Imaging optics 31 is configured using, for example, a lens, ambient light RV0 from in the angle of view of plant detection camera 1 is concentrated, and ambient light RV0 forms an image on a predetermined imaging area of photo detector 33.

Photo detector 33 is an image sensor which has a peak of spectral sensitivity with respect to wavelength of visible light (for example, 0.4 to 0.7 μm). Photo detector 33 converts an optical image that forms an image on the imaging surface to the electrical signal. Output of photo detector 33 is input to image signal processor 35 as the electrical signal. Note that, imaging optics 31 and photo detector 33 function as an imaging unit in visible light camera VSC.

Image signal processor 35 uses the electrical signal which is output of photo detector 33, and visible light image data is generated which is specified by a user in recognizable red, green, and blue (RGB), brightness and color difference (YUV), and the like. Thereby, visible light image data that is imaged by visible light camera VSC forms visible light camera image data. Image signal processor 35 outputs the visible light image data to display controller 37.

In a case where display controller 37 uses visible light image data that is output from image signal processor 35 and detection result image data that is output from display processor 29, and detects water at any position of the visible light image data, display data in which visible light image data and detection result image data are composited, or display data which comparatively represents the visible light image data and detection result image data are generated as examples of information related to water. Display controller 37 (output unit) prompts display by transmitting display data to data logger DL or communication terminal MT that are connected via, for example, a network.

Data logger DL transmits display data that is output from display controller 37 to communication terminal MT or one or more externally connected device (not shown), and prompts display of display data on a display screen of communication terminal MT or one or more externally connected device (for example, monitor 50 within the control room in the office indicated in FIG. 1).

Communication terminal MT is, for example, a portable communication terminal which is used by an individual user, receives display data that is transmitted from display controller 37 via the network, and displays display data on the display screen of communication terminal MT.

(Description of Example of Initial Operation in Invisible Light Sensor Controller)

Figure 4:
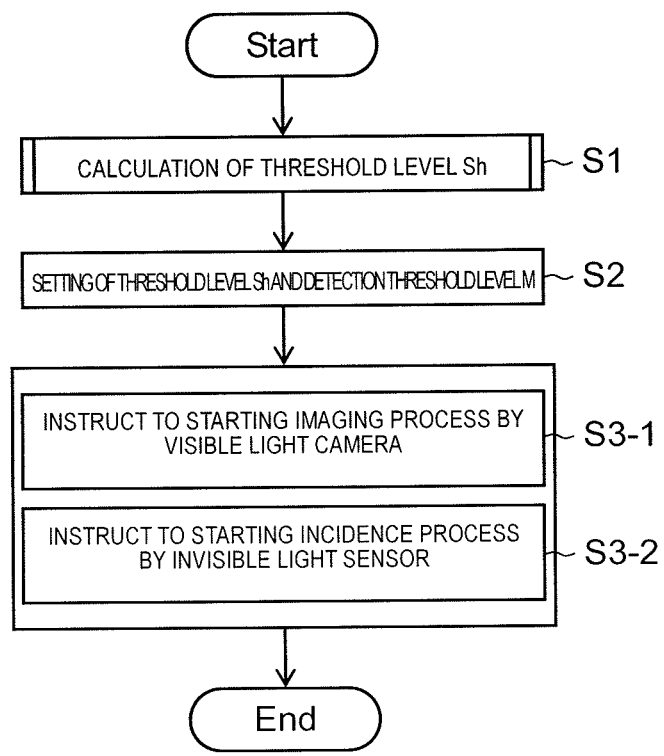
FIG. 4 is a flow chart illustrating an example of an initial setting operation in controller of the plant detection camera.

Next, an example of an initial operation in controller 11 of invisible light sensor NVSS of plant detection camera 1 of the present embodiment will be described with reference to FIG. 4. FIG. 4 is a flow chart illustrating an example of an initial setting operation in controller 11 of plant detection camera 1.

When controller 11 instructs settings of threshold level Sh of reflection intensity ratio for identifying the shape of the leaf with respect to threshold level setter/water content index detector 27a, threshold level setter/water content index detector 27a calculates and sets threshold level Sh (S1). Details of the process in which threshold level Sh is set will be described in detail with reference to FIGS. 27 to 29. Note that, in a case where threshold level Sh is a fixed value, the process of step S1 may be omitted.

In addition, controller 11 sets detection threshold level M of water in detection processor 27 of invisible light sensor NVSS in threshold level setter/water content index detector 27a (S2). It is preferable to appropriately provide detection threshold level M according to a specific substance that is a detection target.

After the process of step S2, controller 11 outputs a control signal for starting an imaging process to each part of visible light camera VSC (S3-1). Furthermore, controller 11 outputs to first beam source 13 and second beam source 15 of invisible light sensor NVSS timing signal for beam scanning TR for starting incidence of reference beam LS1 and measuring beam LS2 to first beam source 13 and second beam source 15 (S3-2). Note that, either an execution timing of an operation of step S3-1 or an execution timing of an operation of step S3-2 may be first, or may be simultaneous.

Figure 5:
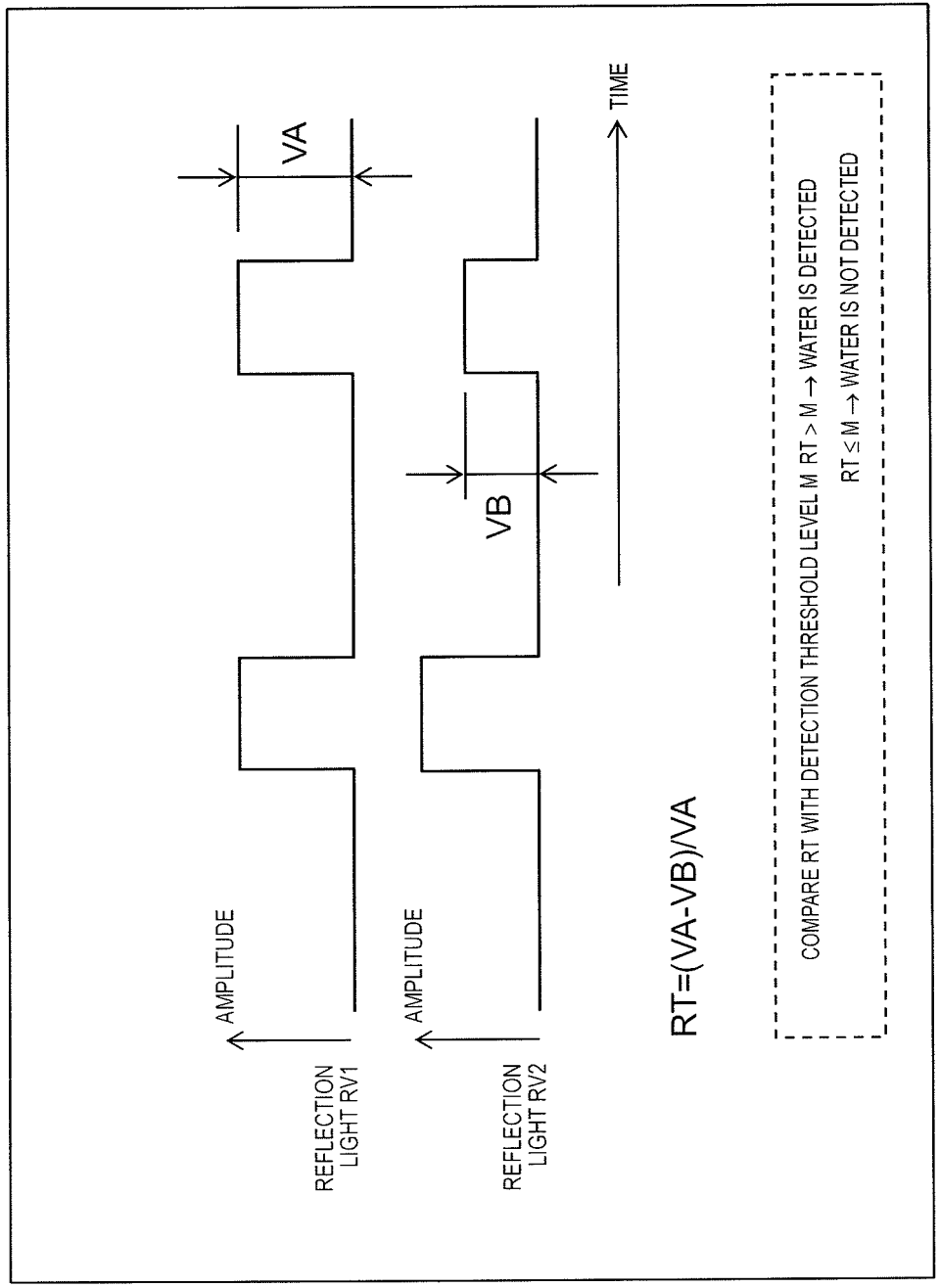
FIG. 5 is a principle explanatory diagram of detection of water in invisible light sensor.

FIG. 5 is a principle explanatory diagram of detection of water in invisible light sensor NVSS. For example, threshold level setter/water content index detector 27a determines that water is detected if RT>M, and determines that water is not detected if RT≤M. In this manner, threshold level setter/water content index detector 27a is able to eliminate influence of noise (for example, disturbance light) and is able to detect presence or absence of water with high precision by detecting presence or absence of water according to a comparative result of rate RT between amplitude difference (VA−VB) and amplitude VA and detection threshold level M.

Figure 6:
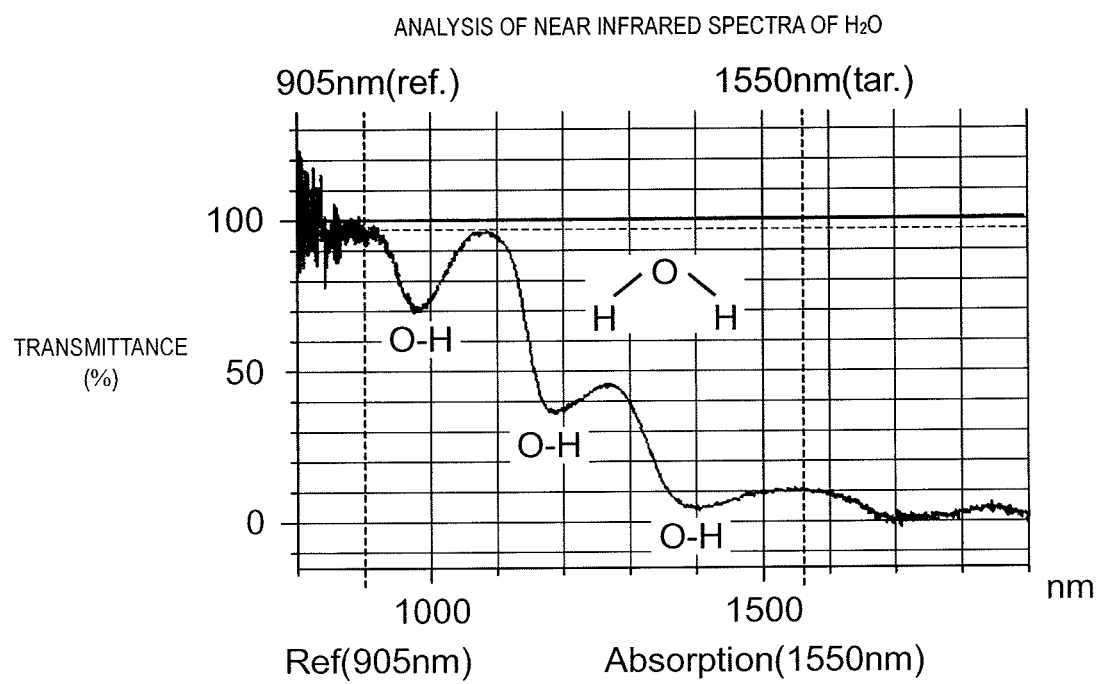
FIG. 6 is a graph illustrating an example of the near infrared spectra of water ($H_2O$).

FIG. 6 is a graph illustrating an example of the near infrared spectra of water ($H_2O$). A horizontal axis of FIG. 6 indicates wavelength (nm), and a vertical axis of FIG. 6 indicates transmittance (transparency) (%). As illustrated in FIG. 6, since reference beam LS1 of wavelength 905 nm has transmittance in water ($H_2O$) that is close to 100%, it is understood that reference beam LS1 has a characteristic in which light tends not to be absorbed in water (refer to ref. in FIG. 6). In the same manner, since measuring beam LS2 of wavelength 1550 nm has transmittance in water ($H_2O$) that is close to 10%, it is understood that measuring beam LS2 has a characteristic of tending to be absorbed in water (refer to tar. in FIG. 6). Therefore, in the present embodiment, the wavelength of reference beam LS1 which is incident from first beam source 13 is 905 nm, and the wavelength of measuring beam LS2 which is incident from second beam source 15 is 1550 nm.

Even in a case where the projection range of the near infrared beam is decreased as the leaf withers, or the leaf is warped or rolled up to increase the thickness of the leaf, in the present embodiment, an average of total sum of the reflection intensity ratio in all pixels of the leaf (hereinafter, referred to as "standardized pixel average water content index" "average water content index", or simply referred to as "water content index") is used as an index of the water content. Accordingly, standardized pixel average water content index Dw is represented by "(1/number of pixels of leaf)$\times \Sigma$ $Ln(I_{905}/I_{1550})$", and has strong correlation with water potential.

(Description of Detailed Operation Relating to Detection of Water of Invisible Light Sensor)

Figure 7:
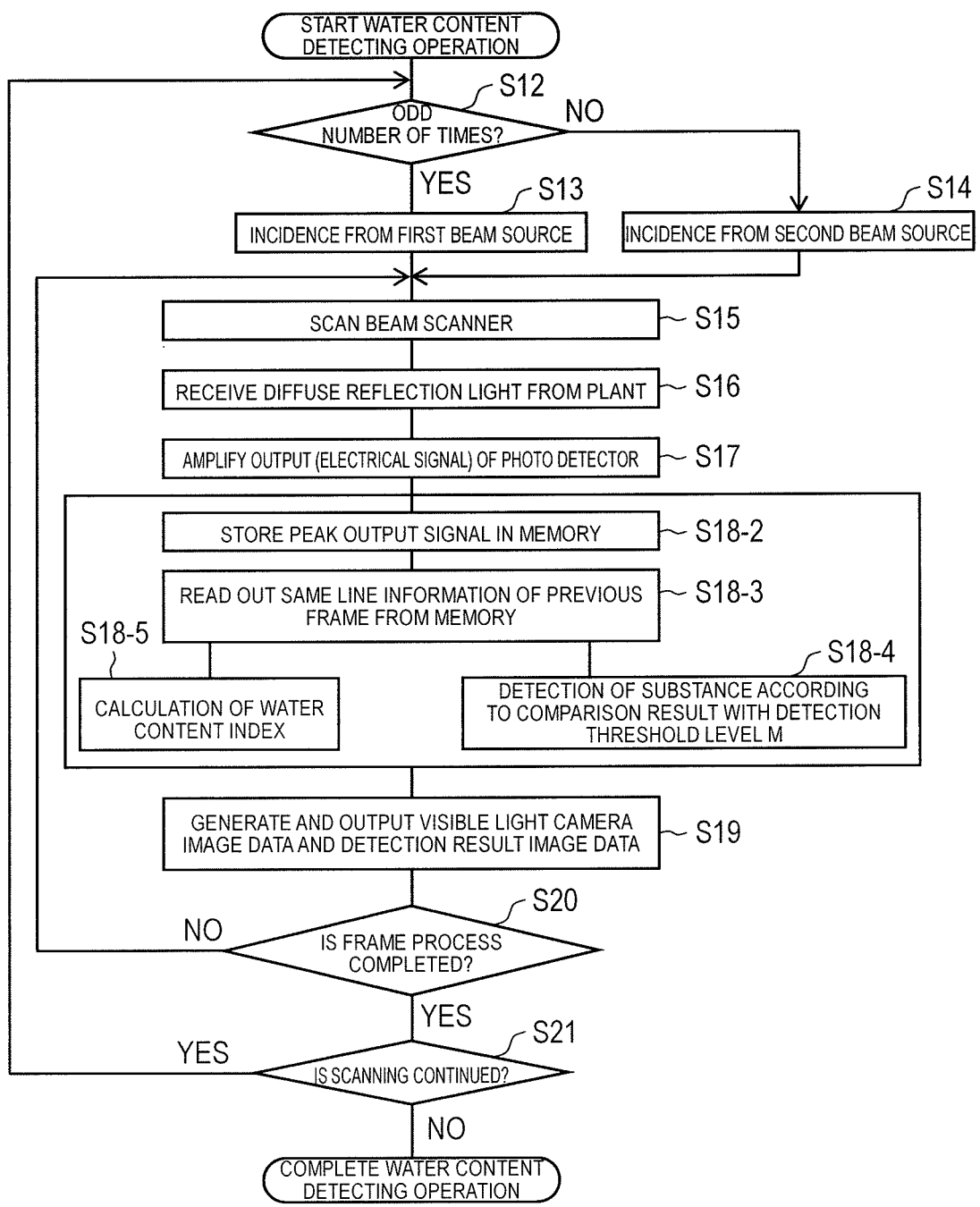
FIG. 7 is a flow chart illustrating an example of a detailed operation procedure which relates to detection of water that is contained in a leaf of a plant in an invisible light sensor.

Next, a detailed operation procedure which relates to detection of water in invisible light sensor NVSS of plant detection camera 1 will be described with reference to FIG. 7. FIG. 7 is a flow chart illustrating an example of a detailed operation procedure which relates to detection of water that is contained in leaf PT3 of plant PT in invisible light sensor NVSS. As a premise of description of the flow chart illustrated in FIG. 7, timing controller 11a outputs timing signal for beam scanning TR to first beam source 13 or second beam source 15, and reference beam LS1 or measuring beam LS2 from plant detection camera 1 is radiated toward leaf PT3 of plant PT.

In FIG. 7, controller 11 determines whether or not beam output signal RF in incidence period of an odd number of times is output from timing controller 11a (S12). In a case where controller 11 determines that beam output signal RF in incidence period of an odd number of times is output from timing controller 11a (YES in S12), first beam source 13 incidents reference beam LS1 according to beam output signal RF from timing controller 11a (S13). Beam scanner 17 one-dimensionally scans reference beam LS1 of one line or more in an X direction of plant PT which is contained in the angle of view of plant detection camera 1 (S15). At the irradiation position on each line in the X direction on which the reference beam LS1 is radiated, diffuse reflection light RV1 that is generated by reference beam LS1 being diffused and reflected is received by photo detector 23 via imaging optics 21 (S16).

In signal processor 25, output (electrical signal) in photo detector 23 of diffuse reflection light RV1 is converted to the voltage signal, and the level of the electrical signal is amplified up to a processable level in comparator/peak hold 25c (S17). Comparator/peak hold 25c binarizes the output signal of amplifier 25b and outputs to threshold level setter/water content index detector 27a according to a comparative result of the output signal of amplifier 25b and the predetermined threshold level. Comparator/peak hold 25c outputs peak information of output signal of amplifier 25b to threshold level setter/water content index detector 27a.

Threshold level setter/water content index detector 27a temporarily stores output (peak information) of comparator/peak hold 25c with respect to diffuse reflection light RV1 of reference beam LS1 in memory 27b (S18-2). In addition, threshold level setter/water content index detector 27a reads from memory 27b output of comparator/peak hold 25c with respect to the same line in diffuse reflection light RV1 or diffuse reflection light RV2 with respect to reference beam LS1 or measuring beam LS2 in a previous frame (incidence period) that is stored in memory 27b (S18-3).

Threshold level setter/water content index detector 27a detects presence or absence of water on the same line based on output (peak information) of comparator/peak hold 25c in diffuse reflection light RV1 of reference beam LS1 and output (peak information) of comparator/peak hold 25c in diffuse reflection light RV2 of measuring beam LS2 on the same line and predetermined detection threshold level M (S18-4).

Threshold level setter/water content index detector 27a calculates a water content index which is a total sum $\Sigma$ Ln $(I_{905}/I_{1550})$ of the reflection intensity ratio (S18-5). Details of calculation of the water content index will be described below.

Display processor 29 uses output of detection result filter 27c and generates detection result image data that indicates the detection position of water. Display controller 37 outputs detection result image data that is generated by display processor 29 and visible light camera image data of a visible light image that is imaged by visible light camera VSC (S19). Each operation of steps S15, S16, S17, S18-2 to S18-5, and S19 is executed in each line within the detection area of one frame (incidence period).

That is, when each operation of steps S15, S16, S17, S18-2 to S18-5, and S19 is complete with respect to one line in the X direction, each operation of steps S15, S16, S17, S18-2 to S18-5, and S19 is performed with respect to a subsequent line in the X direction (NO in S20), hereinafter until each operation of steps S15, S16, S17, S18-2 to S18-5, and S19 is complete in one frame, each operation of steps S15, S16, S17, S18-2 to S18-5, and S19 is repeated regarding the scanning in the Y direction.

Meanwhile, in a case where execution of each operation of steps S15, S16, S17, S18-2 to S18-5, and S19 is complete with respect to all lines in one frame (YES in S20), and in a case where scanning of incident light is continued (YES in S21), an operation of invisible light sensor NVSS returns to step S12. Meanwhile, in a case where scanning of reference beam LS1 and measuring beam LS2 is not continued (NO in S21), the operation of invisible light sensor NVSS is complete.

Figure 8:
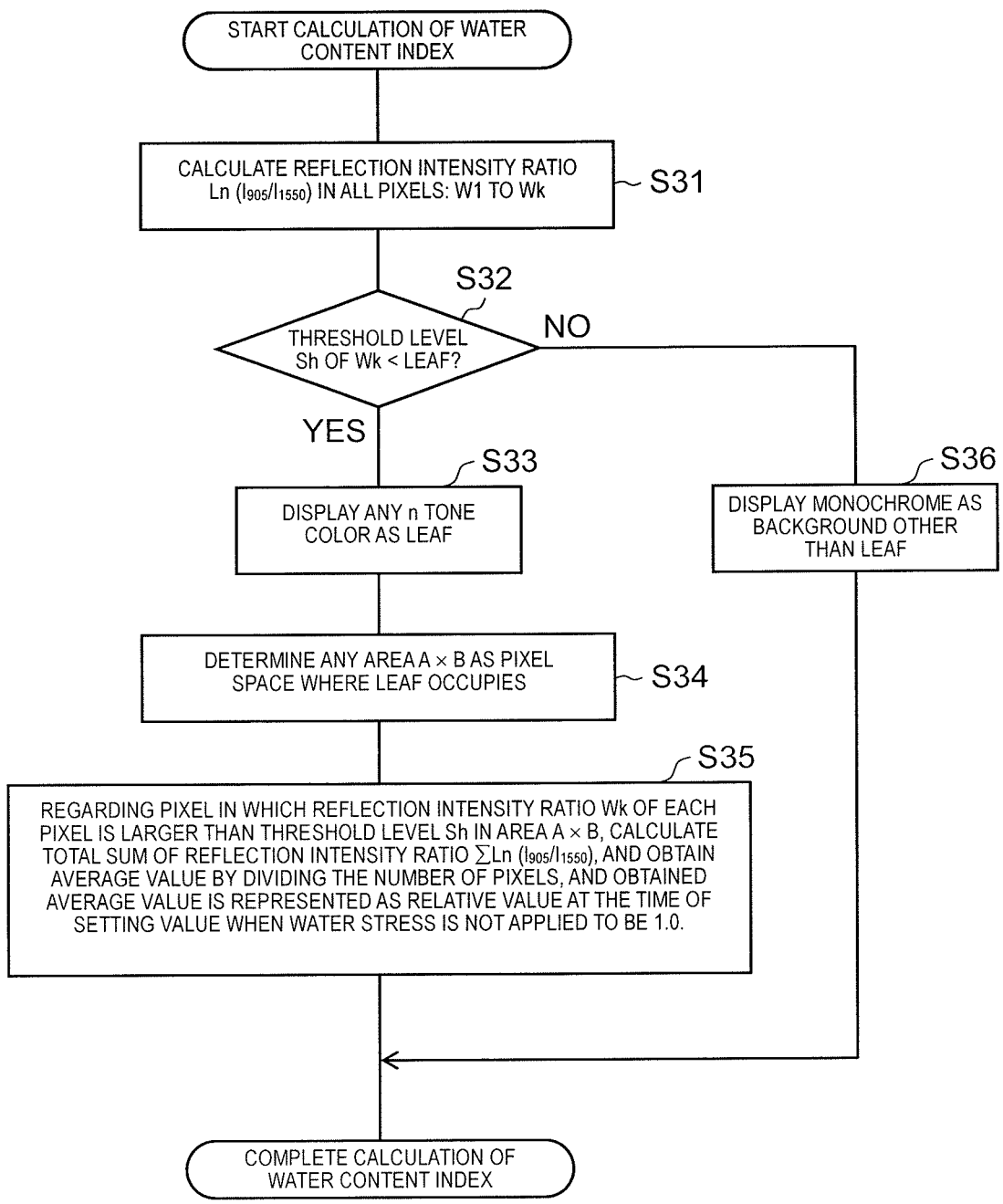
FIG. 8 is a flow chart illustrating an example of a calculation procedure of a water content index in step S18-5.

FIG. 8 is a flow chart illustrating an example of a calculation procedure of a water content index in step S18-5. Threshold level setter/water content index detector 27a calculates the reflection intensity ratio of $\Sigma$ Ln $(I_{905}/I_{1550})$ in all pixels from the frame image (S31). Here, a measurement value of reflection intensity ratio Ln $(I_{905}/I_{1550})$ of each pixel is represented by reflection intensity ratios W1 to Wk. For example, in a case where the image of the near infrared beam is configured from 76,800 (=320×240) pixels, a suffix k of Wk is a variable which represents 1 to 76,800.

Threshold level setter/water content index detector 27a determines whether or not the reflection intensity ratio Wk of each pixel is larger than threshold level Sh for identifying leaf PT3 (S32). An initial value of threshold level Sh is registered in advance in threshold level setter/water content index detector 27a as an empirical value. The empirical value is determined according to a specification of the device for observing water content (intensity of the irradiation laser beam, sensitivity of a light receiving element, and the like), water content (approximately 90%) of the leaf that is the measurement target, thickness of the leaf (for example, 200 µm), inside/outside (or "indoor/outdoor"), and the like. In particular, in a case of outside, there is change according to how sunlight hits or manner of growth of foliage, and the variable is changed each time.

For example, as the empirical value, in the case of an imaging distance of 1 m, threshold level Sh during imaging inside is set to approximately 0.3. Threshold level Sh during imaging outside is set to approximately 0.9. In addition, in the case of an imaging distance of 3 m, threshold level Sh during imaging inside is set to approximately 0.05. It is preferable to change threshold level Sh in a case where threshold level Sh is set as the initial value, it is determined whether or not the threshold level is optimal in comparison to the actual shape of the leaf, and the threshold level is not optimal. In addition, as will be described later, a calculation process of threshold level Sh is performed, and it is possible to register calculated threshold level Sh as the initial value.

In step S32, in a case where reflection intensity ratio Wk is less than threshold level Sh, the pixel is a pixel that represents a background other than the leaf, and display processor 29 generates monochromatic display data for displaying pixels monochromatically (S36).

Meanwhile, in step S32, in a case where reflection intensity ratio Wk is threshold level Sh or more (threshold level or more), display processor 29 displays pixels in a tone color corresponding to reflection intensity ratio Ln $(I_{905}/I_{1550})$ (S33). Here, it is possible to display the tone color corresponding to reflection intensity ratio Ln $(I_{905}/I_{1550})$ at n tone. n is an arbitrary positive number.

In detail, in a case where reflection intensity ratio Ln $(I_{905}/I_{1550})$ is less than 0.3, that is, in a case of being threshold level Sh of the leaf or less, the pixel is displayed using, for example, white (monochrome). Meanwhile, in a case where reflection intensity ratio Ln $(I_{905}/I_{1550})$ is 0.3 to less than 0.4, the pixel is displayed using, for example, dark green. In the same manner, in a case of being 0.4 to less than 0.5, the pixel is displayed using green. In a case of being 0.5 to less than 0.55, the pixel is displayed using yellow. In a case of being 0.55 to less than 0.6, the pixel is displayed using orange. In a case of being 0.6 to less than 0.75, the pixel is displayed using red. In a case of being 0.75 or more, the pixel is displayed using purple. In this manner, the color of the pixel that belongs to the leaf is set in any of six tones.

Note that, in a case where a pixel space which the leaf occupies is not appropriate in comparison to the actual shape of the leaf, the user may set threshold level Sh up or down in each predetermined increment (for example, 0.01). Alternatively, the user may set appropriate threshold level Sh by activating a process in which threshold level Sh described later is automatically set.

Threshold level setter/water content index detector 27a specifies an area of the pixel space which the leaf occupies (S34). The pixels of the leaf are pixels in which reflection intensity ratio Ln ($I_{905}/I_{1550}$) exceeds threshold level Sh (here, 0.3). In addition, an area of a rectangle (A×B) is specified such that the pixels of the leaf are enclosed. The area is used as a value which determines the size of the leaf. Note that, the size of the leaf may represent the pixel number which exceeds threshold level Sh.

Threshold level setter/water content index detector 27a (water content derivation unit) calculates the water content index $\Sigma$ Ln ($I_{905}/I_{1550}$) that is a total sum of reflection intensity ratio Ln ($I_{905}/I_{1550}$) where a measurement value (reflection intensity ratio Ln ($I_{905}/I_{1550}$) is larger than threshold level Sh in area (S35). The water content which is contained in the entirety of the leaf is understood by obtaining water content index $\Sigma$ Ln ($I_{905}/I_{1550}$).

Furthermore, in step S35, it is possible for threshold level setter/water content index detector 27a to calculate the number of pixels in which the measurement value (reflection intensity ratio Ln ($I_{905}/I_{1550}$) is larger than threshold level Sh in the above-described area, and calculate an average value by dividing total sum $\Sigma$ Ln ($I_{905}/I_{1550}$) of the reflection intensity ratio by the number of calculated pixels. The average value is a value in which the total sum of the reflection intensity ratio is divided by the area of the leaf where the external form of the leaf is determined by threshold level Sh, and a value in which the total sum of the reflection intensity ratio in a spot is divided by a fixed area of the spot are different. After this, the calculation operation of the water content index ends.

In this manner, in the present embodiment, the reflection intensity ratio of each irradiation position is not obtained, the reflection intensity ratio of each pixel in the frame image is obtained, and it is possible to correctly calculate the water content index from the total sum of reflection intensity ratio of each pixel. Accordingly, it is possible to accurately determine status of the leaf, that is, the plant.

Figure 27A:
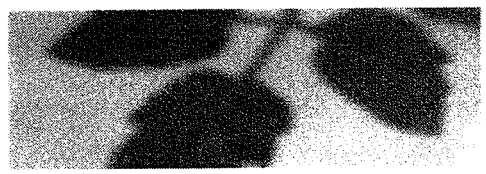
FIG. 27A is a diagram illustrating a frame image that images stalks and leaves of a tomato.
Figure 27B:
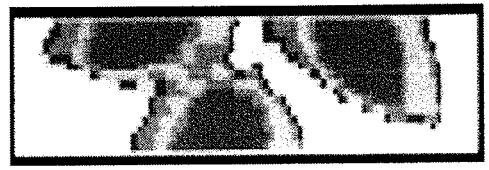
FIG. 27B is a diagram illustrating the occupancy space of the leaf which is obtained in a case where the imaging distance is set to 3 m and a threshold level is set to 0.05 with respect to the visualized near infrared absorption image in FIG. 27A.
Figure 27C:
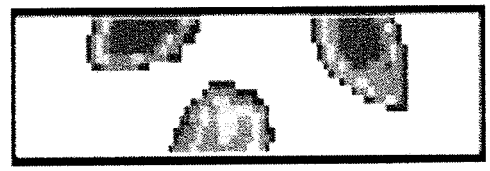
FIG. 27C is a diagram illustrating the occupancy space of the leaf which is obtained in a case where the imaging distance is set to 1 m and a threshold level is set to 0.3 with respect to the visualized near infrared absorption image in FIG. 27A.

Here, as described above, threshold level Sh of the leaf is set to a subsequent value as the initial value. In a case where plant detection camera 1 is installed inside and leaf PT3 is imaged inside, and in a case where imaging distance is empirically 1 m, threshold level Sh is set to approximately 0.3. In the case of an imaging distance of 3 m, threshold level Sh is set to approximately 0.05. Meanwhile, in a case of imaging outside (For example in a greenhouse VGH), since a condition of external light (for example, sunlight) is fluctuated, threshold level Sh is empirically set to approximately 0.9. FIGS. 27A, 27B, and 27C are diagrams illustrating an occupancy range of the leaf. FIG. 27A is a diagram illustrating a frame image that images stalks and leaves of a tomato. A distance between leaves is approximately 1 cm. FIG. 27B illustrates the occupancy space of the leaf which is obtained in a case where the imaging distance is set to 3 m and threshold level Sh is set to 0.05 with respect to the visible light image in FIG. 27A. In this case, it is understood that the leaves overlap in portions and threshold level Sh (=0.05) is a value that is inappropriately set. FIG. 27C illustrates the occupancy space of the leaf which is obtained in a case where the imaging distance is set to 1 m and threshold level Sh is set to 0.3 with respect to the visible light image in FIG. 27A. In this case, the outer form of the leaf does not overlap with another leaf, and the occupancy space of the leaf is the same as the size of the outer form of the leaf of the visible light image. In this case, it is understood that threshold level Sh 0.3) is a value that is correctly set.

Figure 28:
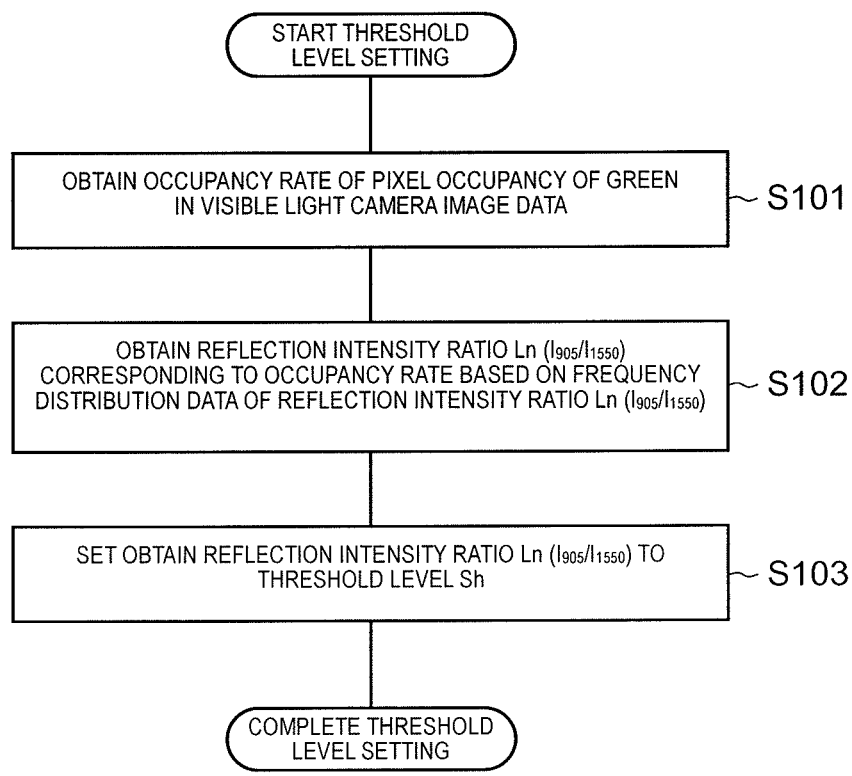
FIG. 28 is a flow chart illustrating a threshold level setting procedure.

In addition, threshold level Sh of the leaf may not be registered before the subsequent process is performed and the calculation process of the water content index indicated in FIG. 8 is executed. FIG. 28 is a flow chart illustrating an example of a threshold level setting procedure.

Threshold level setter/water content index detector 27a obtains an occupancy rate that is determined as the leaf (G pixel number/all pixel numbers), i.e. a pixel occupancy of green (G) that is determined as the color of the leaf with respect to the frame image (for example, refer to FIG. 27A) that is imaged by visible light camera VSC (S101).

Figure 29:
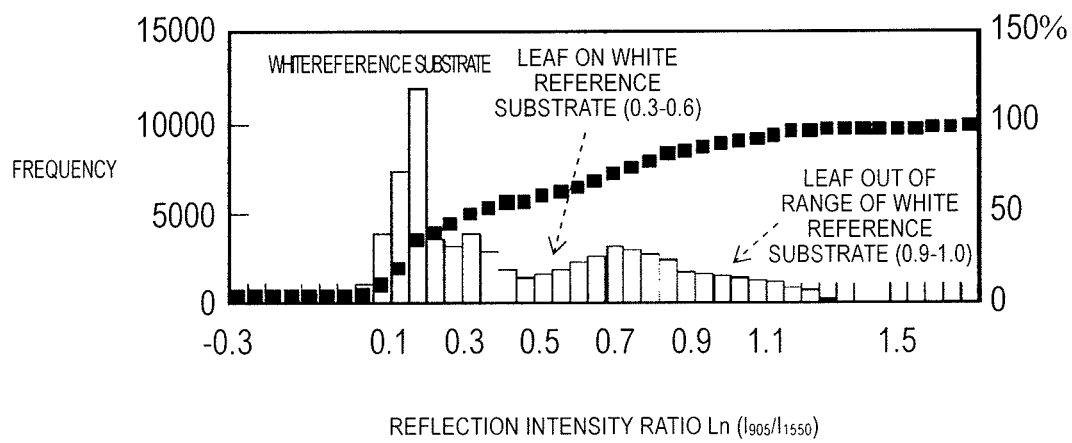
FIG. 29 is a graph illustrating frequency distribution of a reflection intensity ratio in all pixels.

Threshold level setter/water content index detector 27a obtains the water content index corresponding to the occupancy rate of the leaf based on frequency distribution data of the water content index (S102). FIG. 29 is a graph illustrating the frequency distribution of the reflection intensity ratio in all pixels. Frequency distribution data is registered in threshold level setter/water content index detector 27a. When using the frequency distribution data, in a case where, for example, the occupancy rate that is determined as the pixel occupancy of green (G) that is determined as the color of the leaf is 52%, the water content index is approximately 0.3.

Threshold level setter/water content index detector 27a sets the water content index that is obtained in step S102 to threshold level Sh (S103). After this, threshold level setter/water content index detector 27a ends the present process.

In this manner, it is possible to correctly determine the outer form of the leaf by obtaining an occupancy pixel number of green (specified color) of the leaf and threshold level Sh corresponding to cumulative frequency of Ln ($I_{905}/I_{1550}$) that is the measurement value which is the same pixel number by utilizing the visible light image that is imaged by visible light camera VSC, that is, by modifying the threshold level of the water content of each pixel that is contained in the leaf. Accordingly, it is possible to accurately calculate the average value of the pixel unit by correctly determining the outer form of the leaf. In contrast to this, in a case where the fixed area of the spot or the outer form of the visible light image is used, when the outer form of the leaf is not correctly captured, a large error is generated in the average value of the pixel unit.

Here, Comparative Examples will be described for another method of measuring the water content in the leaf. FIG. 9 is a diagram illustrating an example of the method of measuring Comparative Examples. Macrophyll leaf PT3 that is sealed and packed in vinyl bag fk is taken out and fixed to white board wb such that leaf PT3 does not move. White board wb that is firmly fixed to leaf PT3 is placed on weight scale gm, and the weight is measured. At this time, since the weight of white board wb is measured in advance, and is adjusted by 0 points, the weight of the leaf is displayed on a meter of weight scale gm. Change of weight due to transpiration of the leaf is measured while the time elapses. After all measurement ends, the leaf completely dries and the weight is obtained. It is possible to obtain the average water content of leaf at the time of measurement by subtracting the weight of the leaf at depletion from the weight of the leaf at the time of the measurement and further obtaining a ratio of the result of the subtraction to the weight of the leaf before the depletion. The average water content of the leaf substantially lowers while the time elapses.

On the other hand, in the respective embodiments including the present embodiment, at the time of measuring the water content of the leaf, a background material is disposed so as to cover a back surface (rear side) of the leaf that is the measurement target. As the material of the background material, a material that does not contain water and that does not deform due to pesticide, sprinkling, or $CO_2$ spraying is given such as plastic, coated paper, sheets such as aluminum foil (plate), a plate, or a block. In addition, it is desirable that the size of the background material has a large surface such that the leaf that is the measurement target is covered and is a size so as not to interfere with photosynthesis of another leaf within two times the projection area of the leaf that is the measurement target. In addition, it is preferable that the thickness of the background material is a thickness of 50 µm to 1 mm self-supporting without curling, and in particular, 50 to 200 µm. In addition, in a case of being supported by the stalk of the leaf, it is preferable that the weight of the background material is a weight to a degree that the leaf does not wilt. In addition, it is preferable that the color of the background material is white or silver with high reflectance of visible light and the near infrared beam.

In the respective embodiments including the present embodiment, as the background material, a case of using a white reference substrate is indicated. Note that, a white plastic plate, an aluminum plate, a standard white plate, white paper, white nonwoven fabric, and the like are given as the white reference substrate. For example, using a white nonwoven fabric as a white reference substrate makes it easier for $CO_2$ absorption, transpiration, and respiration without hurting the leaf of the observation target even after a few months of observation.

FIG. 10A is a graph illustrating an example of the reflection light intensity with respect to wavelength of the near infrared beam when near infrared beam is radiated toward the leaf outdoors. The vertical axis indicates intensity of the near infrared light which is detected by invisible light sensor NVSS, and the horizontal axis indicates wavelength of a near infrared area. Intensity of light that is scattered by the peripheral leaf other than intensity of light according to sunlight is included in intensity of the near infrared light which is detected by invisible light sensor NVSS. That is, a rise of the background due to multiple scattering of sunlight being carried out on the peripheral leaf is included in the intensity of the detected near infrared light. In addition, intensity of light detected by invisible light sensor NVSS is small due to the near infrared beam which has a wavelength of 1550 nm being absorbed by the peripheral leaf. Accordingly, the value of reflection intensity ratio Ln ($I_{905}/I_{1550}$) is large. Therefore, in a case where water content of the leaf outside is measured, it is necessary to set the value of threshold level Sh that is compared to reflection intensity ratio Ln ($I_{905}/I_{1550}$) to be large.

FIG. 10B is a graph illustrating an example of the reflection light intensity with respect to wavelength of the near infrared beam when near infrared beam is radiated toward the leaf on which white reference substrate bd is installed indoors and outdoors. The vertical axis indicates intensity of the near infrared light which is detected by invisible light sensor NVSS, and the horizontal axis indicates wavelength of a near infrared area. Multiple scattering from peripheral leaf PT3o does not occur due to white reference substrate bd being disposed to cover the back surface (rear side) of leaf PT3t that is the measurement target. Accordingly, a lowering of intensity of the near infrared beam which has a wavelength of 1550 nm does not occur. In addition, in the case of inside, a rise of the background does not occur. Note that, in a case of measuring outside, threshold level Sh is set to approximately 0.5. In addition, in a case of measuring inside, threshold level Sh is set to approximately 0.3.

In a case where white reference substrate bd is disposed on the back surface of leaf PT3t that is the measurement target, the leaf may be disposed without being fixed, and leaf PT3t may be attachably fixed to white reference substrate bd. Here, a case where leaf PT3t is attached to white reference substrate bd is illustrated. In each embodiment including the present embodiment, as seen from first beam source 13 and second beam source 15 of plant detection camera 1, white reference substrate bd is disposed on the back of at least one leaf that is the measurement target.

FIG. 11 is a diagram which describes an example of attachment of leaf PT3t on white reference substrate bd. White reference substrate bd is a white plastic plate which has a vertical rectangular shape. Aperture bd1 that is hollowed out in a rectangular shape is formed in the center of white reference substrate bd. In addition, round hole bd2 is formed in an upper portion of white reference substrate bd. Slit bd21 which reaches up to an upper end surface is formed on hole bd2. In addition, three slits bd3, bd4, and bd5 are respectively formed on the lower side and both sides of aperture bd1 that is formed on white reference substrate bd.

In a case where leaf PT3t is attached to white reference substrate bd, a tip end of leaf PT3t is inserted into one of three slits bd3, a void is generated by shifting horizontal white reference substrate bd in a longitudinal direction centered on slit bd21, stalk PT2 of the leaf passes inside, and stalk PT2 is fixed to hole bd2.

Next, control experiment for the water potential contained in the leaf is performed as the observation of the water content contained in the leaf of plant PT by using plant detection camera 1 of the present embodiment, and the sugar content in the leaf due to the water stress obtained by the result of the experiment is considered.

Figure 12:
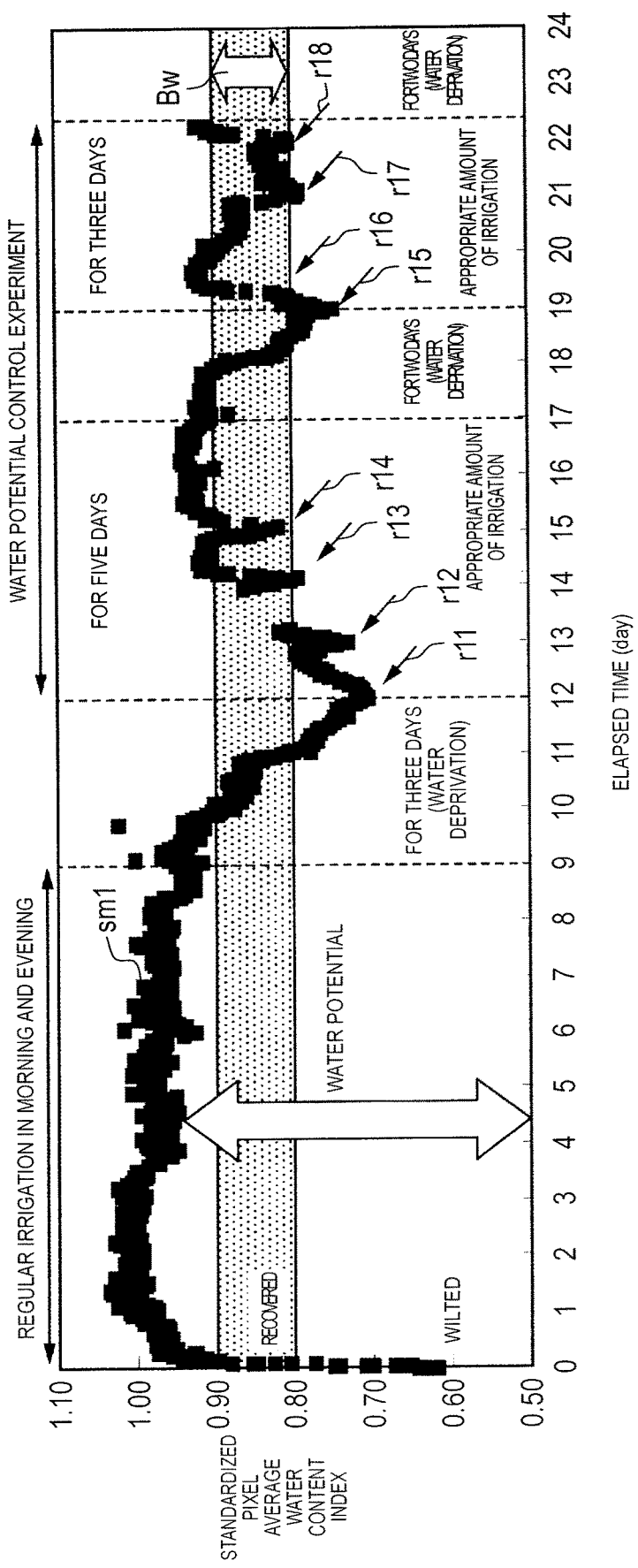
FIG. 12 is a graph illustrating an example of a time-transition of a standardized pixel average water content index in a first water potential control experiment.

FIG. 12 is a graph illustrating an example of a time-transition (time-serial change) of standardized pixel average water content index Dw in the first water potential control experiment. The vertical axis of the graph indicates a standardized pixel average water content index. The standardized pixel average water content index represents a water potential as an index of the water content contained in the leaf that is a measurement target, and corresponds to an average water content in the leaf contained in each pixel in the image capturing the leaf of the plant. The horizontal axis of the graph represents the elapsed time in days. Target range Bw as an example of the range of the target water content represents, for example, The target range of water content determined to be suitable for increasing a sugar content of a fruit of a tomato, and here, a value corresponding to standardized pixel average water content index Dw is set to be a value in a range of 0.8 to 0.9. This target range Bw varies depending on the types of plants and even the same plants or the site of observation (leaves, stalks, and the like). In addition, in FIG. 12 and FIG. 13, in a case where standardized pixel average water content index Dw is smaller than target range Bd, the plant feels water stress.

The first water potential control experiment as illustrated in FIG. 12 shows an example of time-transition of the standardized pixel average water content index in a case where irrigation with nearly adequate irrigation amount is performed at irrigation timing. In FIG. 12, starting from a state where the leaf which is plant sample sm1 is wilted, the water potential control experiment is started after recovering by regular irrigation. In the regular irrigation, irrigation was periodically performed twice a day in the morning and evening in the day. On the other hand, in the water potential control experiment, the irrigation is performed at the timing determined to be appropriate based on the value of standardized pixel average water content index Dw, and periodical irrigation is not performed. Hereinafter, experiment results illustrated in FIG. 12 will be described. In addition, a temporal transition of standardized pixel average water content index Dw as illustrated in FIG. 12 is displayed on monitor 50.

Standardized pixel average water content index Dw of the leaf begins with a wilting state close to the value 0.60 and normal irrigation is started (day 0). After the start of normal irrigation, the next day, standardized pixel average water content index Dw of the leaf recovered to the value close to 1.0. In addition, the normal irrigation was periodically (dayS1 to 8) performed so that the value of standardized pixel average water content index Dw of the leaf was kept to be close to 1.0 for about a week. After that, water deprivation was performed for three days (days 9, 10, and 11). As a result of water deprivation, standardized pixel average water content index Dw of the leaf was gradually decreased and fell down to the value close to 0.7 (day 12).

As indicated by arrow r11 at current point, when a certain amount of irrigation is performed, standardized pixel average water content index Dw in the leaf rises and the peak thereof is temporarily included within target range Bw, then falls down based on the non-irrigation, and falls out of target range Bw. When the same certain amount of the irrigation is performed again at the timing indicated by arrow r12, standardized pixel average water content index Dw in the leaf rises again and the peak thereof is temporarily included in target range Bw, and thereafter, standardized pixel average water content index Dw in the leaf falls down based on the non-irrigation. At this time, standardized pixel average water content index Dw is lower than target range Bw, but the deviation amount thereof is smaller than that in the previous time. When the same certain amount of the irrigation is performed again at the timing indicated by arrow r13, the peak of standardized pixel average water content index Dw falls down after exceeding the upper limit value of target range Bw, but in this time, standardized pixel average water content index Dw is not lower than target range Bw. Furthermore, when the same certain amount of the irrigation is performed at the timing indicated by arrow r14, the peak of standardized pixel average water content index Dw falls down after exceeding the upper limit value of target range Bw, but standardized pixel average water content index Dw is mostly stayed in target range Bw (dayS12 to 16).

Even though water deprivation occurred for the following two days (dayS17 and 18), as indicated by arrows r15, r16, r17, and r18, similar irrigation was performed so that standardized pixel average water content index Dw was controlled to be substantially within target range Bw.

Figure 13:
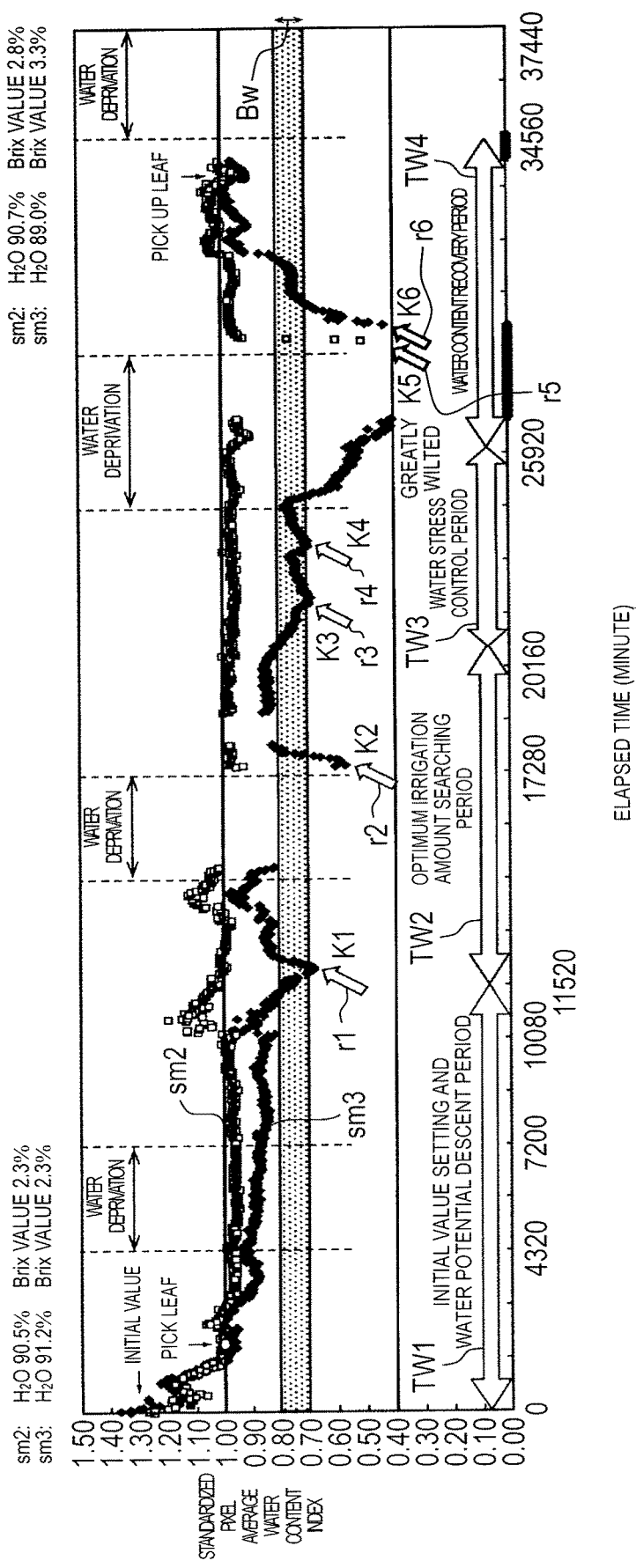
FIG. 13 is a graph illustrating an example of a time-transition of a standardized pixel average water content index in a second water potential control experiment.

FIG. 13 is a graph illustrating an example of a time-transition of standardized pixel average water content index Dw in the second water potential control experiment. The vertical axis of the graph indicates standardized pixel average water content index Dw, as illustrated in FIG. 12. The horizontal axis of the graph represents the elapsed time in minutes. In the second water potential control experiment, two plant samples sm2 and sm3 (for example, tomatoes) of the same types, which are different from the first plant sample sm1, were used. For plant sample sm2 (Comparative Example), the normal irrigation is periodically performed twice a day in the morning and evening in the day. On the other hand, for plant sample sm3 (Example corresponding to the present embodiment), the irrigation is performed while applying the water stress. That is, for plant sample sm3, similar to the water potential control period (dayS12 to 22) as illustrated in FIG. 12, the irrigation is only performed at the irrigation timing.

In the second water potential control experiment, as illustrated in FIG. 13, the observation of standardized pixel average water content index Dw in the leaf was performed during four periods of water potential descent period TW1, optimum irrigation amount searching period TW2, water stress control period TW3, and water content recovery period TW4. Target range Bw of standardized pixel average water content index Dw was different from target range Bw illustrated in FIG. 12, and was set to be a value in a range of in a range of 0.70 to 0.80. The reason for this that the plant samples used in the second water potential control experiment were different from each other.

The initial values of the water content rate of the leaf in Comparative Example and Example are respectively 90.5% and 91.2%, which are almost the same each other. In addition, these standardized pixel average water content indexes Dw are close to the value of 1.30, which are almost the same each other. Further, the Brix values representing the sugar content of Comparative Example and Examples are the value of 2.3%, which are almost the same each other.

During the period of the control experiment of the water potential, the normal irrigation was continued for plant sample sm2 of Comparative Example.

On the other hand, the irrigation was not performed for plant sample sm3 of Example during water potential descent period TW1 (period from 0 to 11520 minutes) for plant sample sm3 of Example. As a result, since the initial value is set, standardized pixel average water content index Dw in the leaf of Comparative Example is nearly constant at the value close to 1.0; whereas standardized pixel average water content index Dw in the leaf of Example is gradually lowered, and is smaller than the value 0.70 which is the lower limit value of target range Bw at the end of water potential descent period TW1.

In optimum irrigation amount searching period TW2 (period from 11520 to 20160 minutes), firstly, standardized pixel average water content index Dw in the leaf of Example was smaller than the lower limit value of 0.70 of the target range so that the irrigation of irrigation amount K1 was performed at the time (timing) indicated by arrow r1. As a result, standardized pixel average water content index Dw in the leaf of Example rapidly rose, exceeded the upper limit value of target range Bw, and became the value close to 1.00. It is determined that irrigation amount K1 was excessively large at this point. After that, the water deprivation period began, and standardized pixel average water content index Dw in the leaf of Example was smaller than the lower limit value of the target range again so as to reach the value of 0.60. The water deprivation period is completed, irrigation of irrigation amount K2 was performed at the time indicated by arrow r2. As a result, standardized pixel average water content index Dw rose, and slightly exceeded target range Bw. Based on these results displayed on monitor 50, it can be determined that the optimum irrigation amount is less than irrigation amounts K1 and K2.

In water stress control period TW3 (period from 20160 to 25920), when standardized pixel average water content index Dw in the leaf of Example was decreased again, and was smaller than the lower limit value of target range Bw, the irrigation with irrigation amount K3 smaller than irrigation amounts K1 and K2 was performed at the time indicated by arrow r3. Also, standardized pixel average water content index Dw was smaller than the lower limit value of target range Bw, and at the time indicated by arrow r4, the irrigation was performed with irrigation amount K4 similar to irrigation amount K3. As described above, when the irrigation with irrigation water amounts K3 and K4 is intermittently performed, standardized pixel average water content index Dw transitions so as to be substantially within target range Bw while applying the water stress to plant sample sm3. Thereafter, since the leaf of plant sample sm3 of Example entered a certain water deprivation period, the degree of wilting of the leaf was increased, standardized pixel average water content index Dw was decreased, and thereby standardized pixel average water content index Dw of plant sample sm3 dropped to the value of 0.4.

The water deprivation period was completed, and in water content recovery period TW4 (period from 25920 to 34560), the degree of wilting of the leaf of plant sample sm3 was large, and thus the irrigation was performed with irrigation amounts K5 and K6 which are larger than irrigation amounts K3 and K4 at the time indicated by arrows r5 and r6.

At the end of water content recovery period TW4, when the rate of water content in the leaf of the plant samples sm2 and sm3 in Comparative Example and Example reached approximately the same values as the initial values (90.7%, 89.0%), as a result of measuring the Brix value representing each sugar content, the Brix value in Comparative Example was 2.8%; whereas in Example, the Brix value was 3.3%. That is, the Brix value of Comparative Example was increased by 0.5% from the value of 2.3% to 2.8% before and after the water potential control; whereas the Brix value of Example was greatly increased by 1% from the value of 2.3% to 3.3%.

In this way, compared to plant sample sm2 of Comparative Example in which the irrigation was performed at regular intervals without applying the water stress, in plant sample sm3 of Example, the irrigation was performed at the timing when standardized pixel average water content index Dw reached close to the lower limit of the target range while applying water stress based on non-irrigation so that an increase in the sugar content in the leaf was increased, and the sugar content in the leaf was increased due to the water stress. In this way, it was found that the sugar content of the leaf was increased by applying the water stress through the water potential control experiment in FIG. 13. In addition, when the sugar content of the leaf becomes higher, the leaf becomes in a healthy state as a whole plant by transferring the sugar content to the root and the fruit by the phenomenon of translocation and osmoregulation.

Here, the sugar content in the leaf was measured in the following procedures (T1) to (T5).

(T1) A leaf such as a tomato is dried at temperature of 105° C. for two hours. From this change in weight, the water content can be calculated.

(T2) The dried leaf is put into a mortar, and is crushed and ground to be in a powder state.

(T3) The powder obtained by crushing the leaf is put into a container containing hot water at 60° C. which has four times water content (before drying) contained in the leaf, and stir at room temperature for 2 hours.

(T4) The container containing the leaf powder is left to stand, and the leaf powder is allowed to be settled spontaneously for 15 hours or more.

(T5) A supernatant was extracted and the Brix value thereof was measured by using a sugar content meter. Here, since this Brix value is a provisional Brix value obtained using hot water four times the water content in the leaf, a true Brix value can be obtained according to Expression (1). Note that, the calculation of the true Brix value by Expression (1) may be performed by controller 11 when the Brix value obtained by the sugar content meter is input.

$$\text{True Brix value (\%)} = [\text{provisional Brix value} \times \text{water content} \times 4 \text{ times}/(1-\text{provisional Brix value})] \div [\text{water content} + (\text{provisional Brix value} \times \text{water content} \times 4 \text{ times})/(1-\text{provisional Brix value})] \times 100 \quad (1)$$

Figure 14:
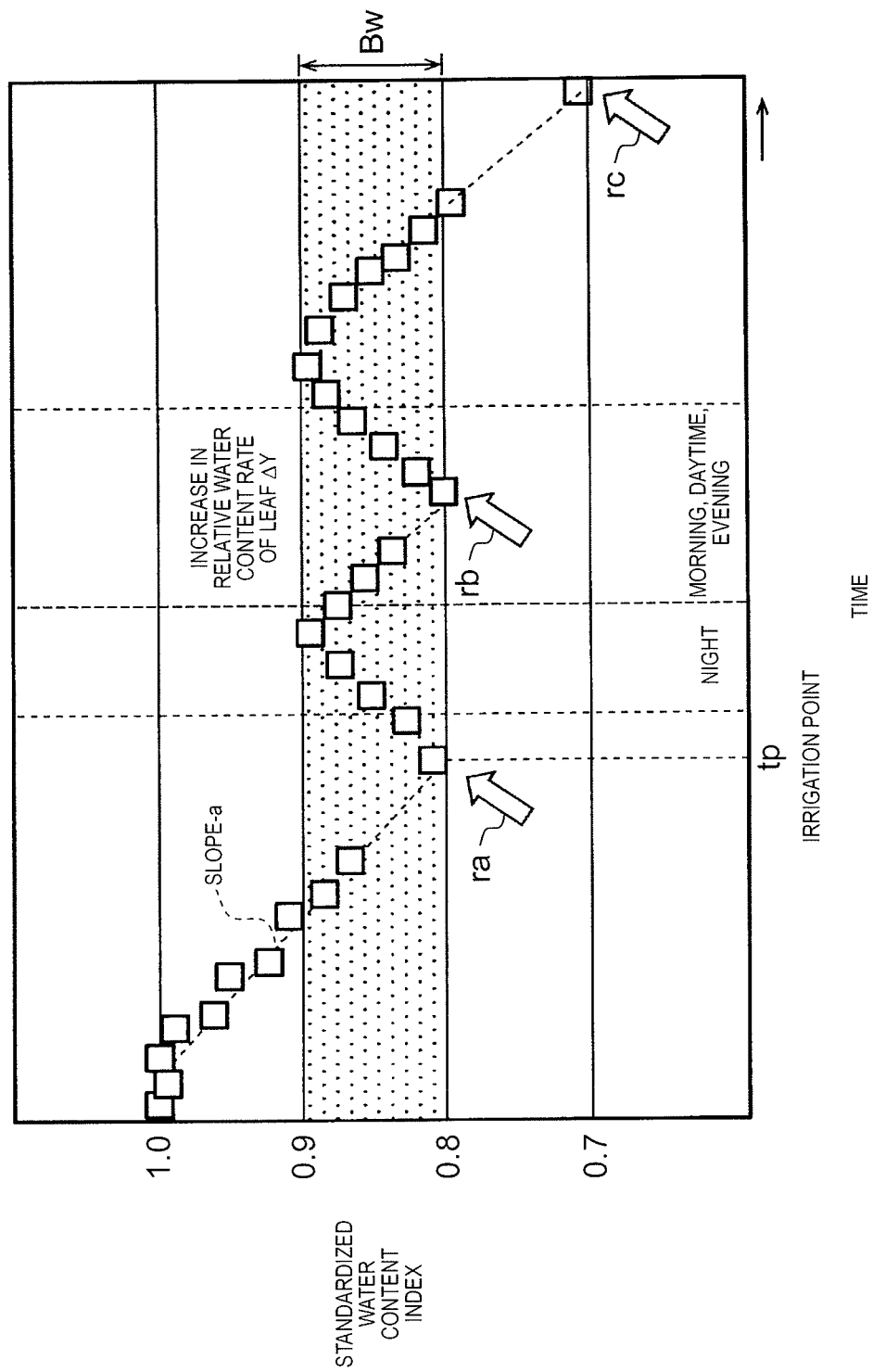
FIG. 14 is a graph illustrating an example of an irrigation amount and irrigation timing.

On the basis of the control experiment of the water potential, the following irrigation amount and irrigation timing are considered. FIG. 14 is a graph illustrating an example of an irrigation amount and irrigation timing. The vertical axis of the graph indicates a standardized water content index (that is, standardized pixel average water content index Dw). The horizontal axis represents elapsed time. In the graph, a measurement point is represented by a rectangle. Target range Bw is set to be a value in a range of 0.8 to 0.9.

An initial value of standardized pixel average water content index Dw in the leaf is set a value of 1.0. When standardized pixel average water content index Dw is gradually decreased with the lapse of time from the initial value and reaches close to the lower limit value of target range Bw, the following irrigation is performed. When a slope (descending speed) at which standardized pixel average water content index Dw is decreased is "−a", the timing indicated by arrow ra at which standardized pixel average water content index Dw crosses the lower limit value of target range Bw is irrigation point tp.

Irrigation amount Kp in irrigation point tp is calculated by using, for example, Expression (2).

$$\text{Next water content in leaf} = \text{present water content in leaf} + \text{amount of water absorption from root} - \text{amount of transpiration from leaf} \quad (2)$$

Here, the amount of water absorption from the root is calculated by the irrigation amount, osmotic pressure (electric conductivity) of a liquid fertilizer, the number (surface area) of roots, and the like. The amount of transpiration from the leaf is obtained from the number of leaves, a leaf area, saturation deficit (that is, a difference between saturated water vapor pressure and relative humidity), and the like. Generally, it is said that photosynthesis of a leaf is active and the transpiration is actively performed on a sunny day and when the saturation deficit is between 3 to 7 g/m³ (that is, the period in which the relative humidity is around 75% RH). Therefore, the water content in the leaf tends to be decreased due to the transpiration in the morning and daytime on a sunny day; whereas in the evening (sunset), when the amount of transpiration of the leaf is decreased, the water content in the leaf is increased. In addition, the leaf is not subjected to the photosynthesis at night, and thus the change in the water content in the leaf is small. Since the relative humidity is high on a rainy day, the transpiration is not performed even if the pore is opened, and thus the change in the water content in the leaf is small, and on the day when the temperature is high such as summer, the plant closes the pores so as not to lose the water in the body any more so that the transpiration is not performed, and thereby the change in the water content in the leaf is small.

When the irrigation is performed, standardized pixel average water content index Dw rises, reaches the upper limit value of target range Bw, and then repeats a falling-down operation. At the timing indicated by arrow rb, the same irrigation as that at the timing indicated by arrow ra is performed. Thereafter, at the timing indicated by arrow rc, the irrigation is performed at the timing when standardized pixel average water content index Dw reaches the value 0.7, which is lower than the lower limit value of target range Bw, that is, in a state where the water stress is increased. This makes it possible to apply the water stress to the plant.

Figure 15:
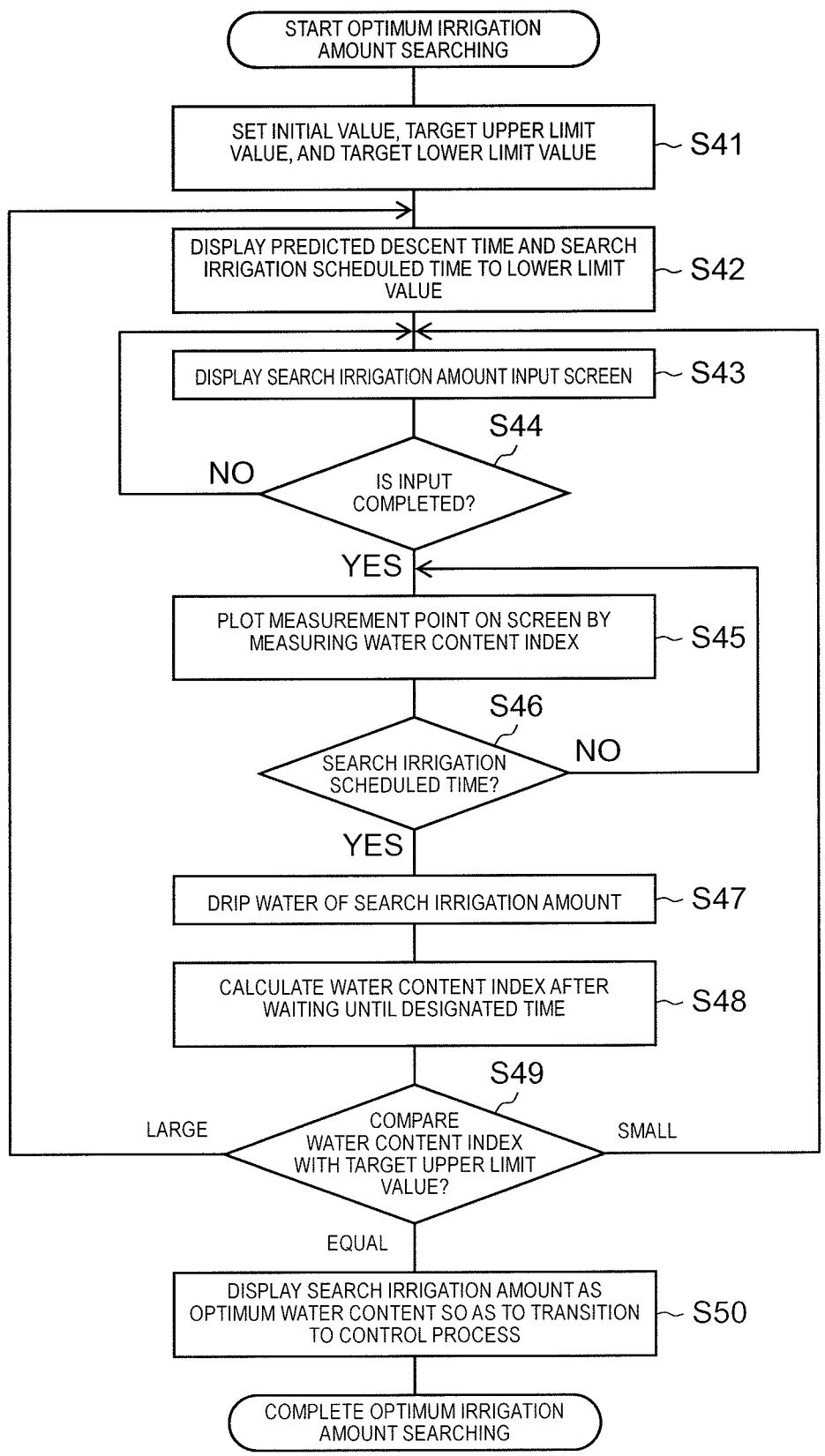
FIG. 15 is a flow chart illustrating an example of searching procedure of the optimum irrigation amount in the first embodiment.
Figure 16:
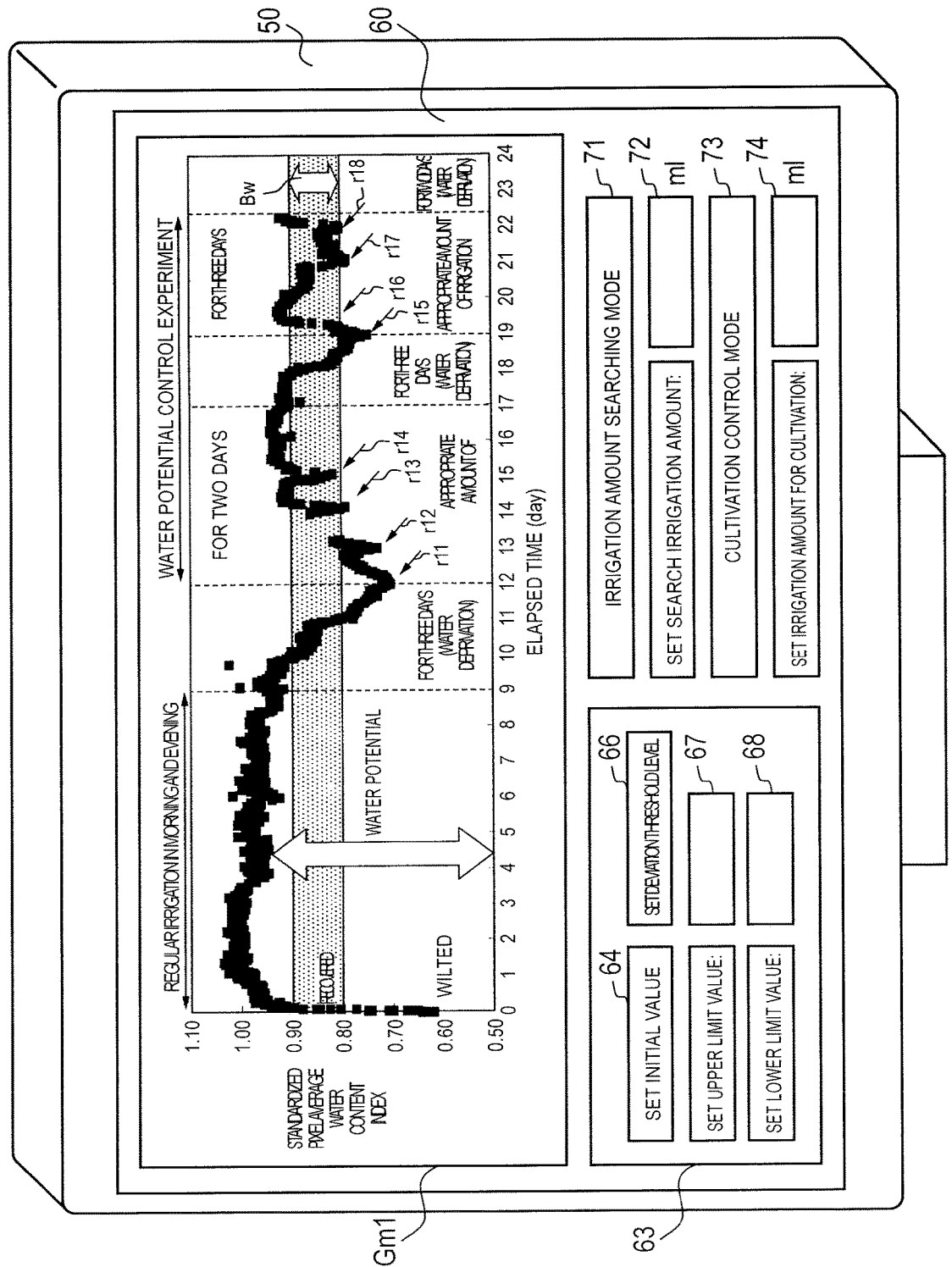
FIG. 16 is a diagram illustrating an example of a user interface (UI) screen relating to water potential control.

FIG. 15 is a flow chart illustrating an example of searching procedure of the optimum irrigation amount in the first embodiment. This optimum irrigation amount searching operation is a process executed in optimum irrigation amount searching period TW2 as illustrated in FIG. 13. For example, when irrigation amount searching mode button 71 is pressed on UI screen 60 as illustrated in FIG. 16, the optimum irrigation amount searching operation is executed.

In the optimum irrigation amount searching operation, first, controller 11 sets an initial value, and the upper limit value and the lower limit value of target range Bw by the operation of a user with respect to UI screen 60 (for example, a farmer of tomatoes who is a user) (S41). Controller 11 displays a predicted descent time and a search irrigation scheduled time up to the lower limit value of target range Bw (S42). Note that, this search irrigation scheduled time is set to be the same as or near the predicted descent time.

Figure 17:
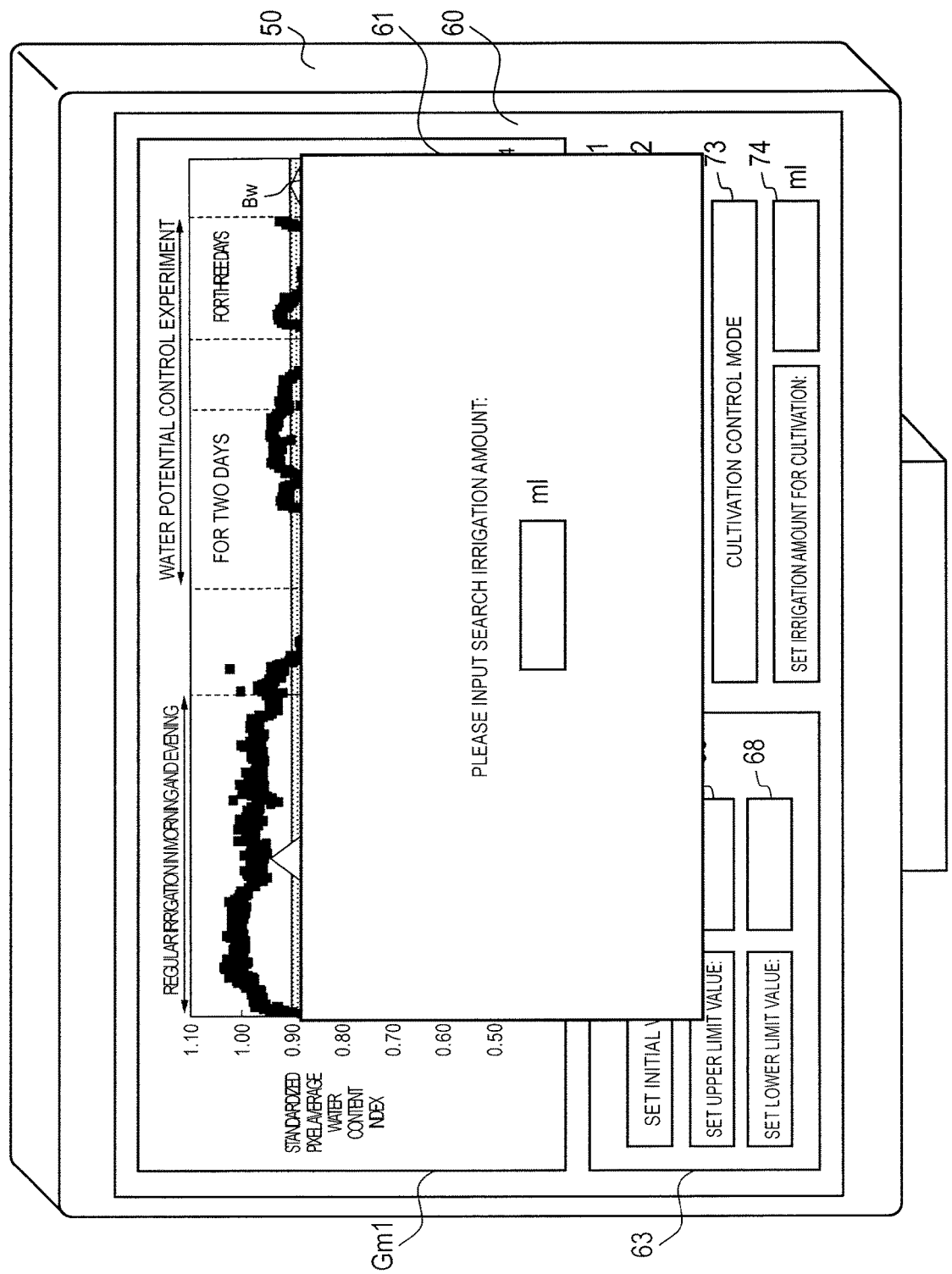
FIG. 17 is a diagram illustrating an example of a search irrigation amount input screen pop-up displayed on a UI screen.

Controller 11 displays search irrigation amount input screen 61 illustrated in FIG. 17 (S43). Controller 11 determines whether or not the input of the search irrigation amount has been completed (S44), and if the input is not completed, controller 11 continues to display search irrigation amount input screen 61 in step S43.

In addition, when the input of the search irrigation amount is completed, controller 11 measures standardized pixel average water content index Dw, and adds this measurement point to the graph in screen for monitoring water content in leaf Gm1 which is displayed on UI screen 60 (S45). Controller 11 determines whether or not search irrigation scheduled time has come (S46). In a case where the search irrigation scheduled time has come, controller 11 returns to the process of step S45.

When the search irrigation scheduled time has come, controller 11 controls the dripping water of the search irrigation amount (S47). The search irrigation amount corresponds to irrigation amounts K1 and K2 in FIG. 13. In addition, the dripping of water of the search irrigation amount may be automatically performed by fertilizer or water supply device WF, or may be performed manually by a user. After waiting until the designated time, controller 11 calculates the water content index (S48). This designated time is a time designated so that standardized pixel average water content index Dw reaches the upper limit value of target range Bw, and is set based on the predicted descent time and the search irrigation scheduled time.

Controller 11 compares standardized pixel average water content index Dw with the upper limit value of target range Bw (S49). In a case where standardized pixel average water content index Dw exceeds the upper limit value of target range Bw, controller 11 returns to step S42, and displays the predicted descent time and the search irrigation scheduled time on UI screen 60 again. In addition, in a case where standardized pixel average water content index Dw does not exceed the upper limit value of target range Bw, controller 11 returns to step S43, and displays search irrigation amount input screen 61.

Further, in a case where standardized pixel average water content index Dw becomes equal to the upper limit value of target range Bw, controller 11 displays the search irrigation amount as an optimum water content so as to transition to the process of the cultivation control (S50). This display is pop-up displayed, for example, by a message or the like. Thereafter, controller 11 completes the present operation.

FIG. 16 is a diagram illustrating an example of a user interface (UI) screen 60 relating to water potential control. UI screen 60 includes screen for monitoring water content in leaf Gm1. A graph representing a time-transition of standardized pixel average water content index Dw is displayed on screen for monitoring water content in leaf Gm1 disposed on the upper portion of UI screen 60. This graph is similar to the graph of FIG. 12 described above.

Set area 63 is displayed on the left side of the lower portion of UI screen 60. Initial setting button 64 and deviation threshold level setting button 66 are disposed in set area 63. In addition, input box 67 for setting the upper limit value of target range Bw and input box 68 for inputting the lower limit value of target range Bw are disposed. For inputting numerical values to input boxes 67 and 68, it is possible to use a touch panel, a numeric keypad, a portable terminal, or the like.

Figure 18:
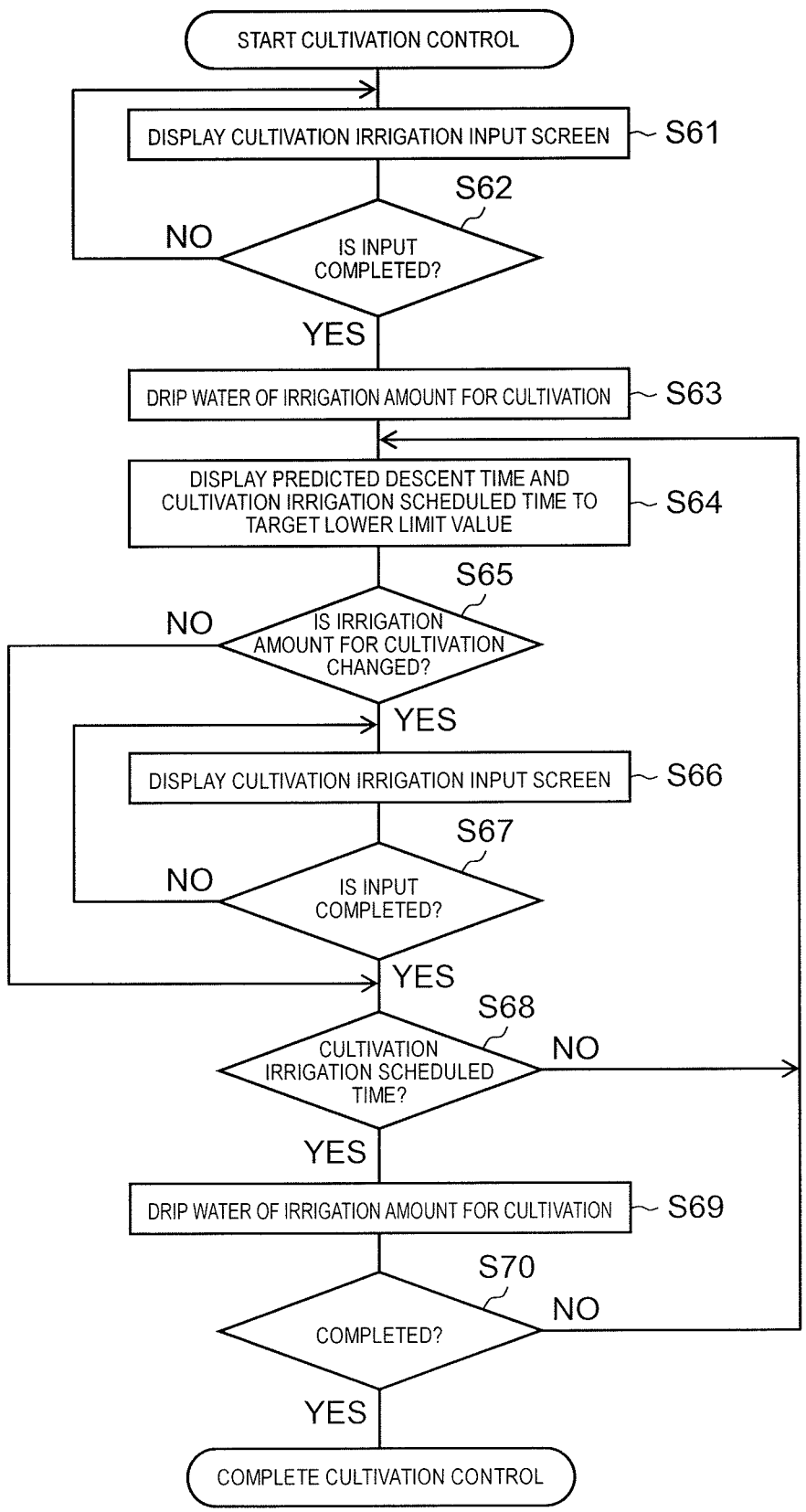
FIG. 18 is a flow chart illustrating an example of procedure of water stress control (cultivation control) of the first embodiment.

In addition, irrigation amount searching mode button 71 and water stress control (cultivation control) mode button 73 are disposed on the right side of the lower portion of UI screen 60. When irrigation amount searching mode button 71 is pressed, the optimum irrigation amount searching operation as illustrated in FIG. 15 is started. When water stress control (cultivation control) mode button 73 is pressed, the cultivation control operation as illustrated in FIG. 18 to be described later is started. Further, on UI screen 60, display box 72 for displaying a setting value of the search irrigation amount and display box 74 for displaying a setting value of the irrigation amount for cultivation are disposed.

FIG. 17 is a diagram illustrating an example of search irrigation amount input screen 61 pop-up displayed on UI screen 60. In search irrigation amount input screen 61, the search irrigation amount is input and set by unit of milliliter (ml). A touch panel, a numeric keypad, a mobile terminal, and the like can be used for inputting the search irrigation amount.

FIG. 18 is a flow chart illustrating an example of procedure of water stress control (cultivation control) of the first embodiment. This cultivation control operation is a process executed in water stress control period TW3 as illustrated in FIG. 13. For example, when water stress control (cultivation control) mode button 73 is pressed on UI screen 60 as illustrated in FIG. 16, the cultivation control operation is executed.

In the water stress control operation, controller 11 firstly displays a cultivation (control) irrigation water content input screen (S61). The input screen of irrigation amount for cultivation is pop-up displayed on UI screen 60 similar to the search irrigation amount input screen.

Controller 11 determines whether or not the input of the irrigation amount for cultivation is completed on the input screen of irrigation amount for cultivation (S62). The irrigation amount for cultivation represents the appropriate irrigation amount calculated in the searching process of optimum irrigation amount searching period TW2 (that is, the flow chart as illustrated in FIG. 15). In a case where the input of the irrigation amount for cultivation is not completed, controller 11 returns to step S61 and continues to display the input screen of irrigation amount for cultivation.

On the other hand, when the input of the irrigation amount for cultivation is completed, controller 11 drips the water of the irrigation amount for cultivation (S63). Controller 11 displays the predicted descent time and the cultivation irrigation scheduled time up to the lower limit value of target range Bw (S64). Note that, this cultivation irrigation scheduled time is set to be the same as or near the predicted descent time.

Controller 11 determines whether or not the irrigation amount for cultivation is changed (S65). In a case where the irrigation amount for cultivation is not changed, controller 11 proceeds to the process of step S68. On the other hand, in a case where the irrigation amount for cultivation is changed, controller 11 displays the input screen of irrigation amount for cultivation again (S66). Controller 11 determines whether or not the input of the irrigation amount for cultivation is completed on the input screen of irrigation amount for cultivation (S67). In the case where the input of the irrigation amount for cultivation is completed, controller 11 returns to step S66 and continues to display the input screen of irrigation amount for cultivation.

On the other hand, when the input of the irrigation amount for cultivation is completed, controller 11 determines whether or not the cultivation irrigation scheduled time has come (S68). In a case where the cultivation irrigation scheduled time has come, controller 11 returns to the process of step S64. When the cultivation irrigation scheduled time has come, controller 11 drips the water of the irrigation amount for cultivation (S69). Controller 11 determines whether or not the cultivation control is completed (S30). In a case where the cultivation control is not completed, controller 11 returns to the process of step S64. On the other hand, in the case where the cultivation control is completed, controller 11 completes the present operation.

Next, a water stress profile for applying the water stress to the plant will be described. FIG. 19A, FIG. 19B, FIG. 19C, and FIG. 19D is a graph schematically illustrating an example of a water stress profile. In water stress profile pf 1 as illustrated in FIG. 19A, the irrigation is performed such that the water content index (that is, standardized pixel average water content index Dw) is fluctuated between the upper limit value and the lower limit value target range Bw (the range of the target water content). That is, the irrigation with the irrigation amount which reaches the upper limit value of target range Bw is performed at the timing of the lower limit value of target range Bw. In this case, the water stress is small.

In water stress_profile pf2 as illustrated in FIG. 19B, the irrigation is performed by the lower limit value of target range Bw, and the peak of standardized pixel average water content index Dw falls in the middle of target range Bw such that the fluctuation of standardized pixel average water content index Dw is reduced. In this case, the water stress is slightly small.

In water stress profile pf3 as illustrated in FIG. 19C, after standardized pixel average water content index Dw falls down to an wilting point, the irrigation is performed with a large amount of irrigation, and after standardized pixel average water content index Dw rises until it exceeds the value of 1, it falls down again to the wilting point, and the irrigation is performed in the same manner. In this case, there is no water stress in an area where standardized pixel average water content index Dw exceeds the value of 1, and the water stress is large in the vicinity of the wilting point. This water stress profile pf3 is used, for example, in a case where the water content index is changed at flowering and fruiting season of the plant in another stage or the weather is changed.

In water stress profile pf4 as illustrated in FIG. 19D, after standardized pixel average water content index Dw falls down to the wilting point, the irrigation is performed with the irrigation amount that reaches the upper limit value of target range Bw, and when standardized pixel average water content index Dw reached the upper limit value of target range Bw, and then reaches the lower limit value of target range Bw again, the irrigation with the irrigation amount that reaches the upper limit value of target range Bw is performed. Such operations are alternately repeated. In this case, when standardized pixel average water content index Dw is in the vicinity of the wilting point, the water stress becomes larger, and when standardized pixel average water content index Dw is in the vicinity of the lower limit value of target range Bw, the water stress becomes smaller. Note that, these water stress profiles are an example, and other water stress profiles can be applied.

As described above, in plant detection camera 1 according to the first embodiment, first beam source 13 of plant detection camera 1 performs optical scanning so that the near infrared beam (reference beam) of the first wavelength (905 nm), which has a characteristic in which light tends not to be absorbed in water is radiated toward leaf PT3 of plant PT. Second beam source 15 of plant detection camera 1 performs optical scanning so that the near infrared beam (measuring beam) of the second wavelength (1550 nm), which has a characteristic easily absorbed by water is radiated toward leaf PT3 of plant PT. Threshold level setter/water content index detector 27a calculates water content index of one leaf, which is a total sum of the reflection intensity ratio $\Sigma$ Ln $(I_{905}/I_{1550})$ based on the reflection light of 905 nm reflected on the entire irradiation position of leaf PT3 and the reflection light of 1550 nm reflected on the entire irradiation position of leaf PT3. Controller 11 displays a graph representing the time-transition of the water content contained in leaf PT3 of plant PT from the start to the end of the measurement period on UI screen 60 of monitor 50. When viewed from first beam source 13 and second beam source 15, white reference substrate bd (background material) which covers a back surface of leaf PT3 of plant PT is disposed on leaf PT3 of plant PT.

As such, according to plant detection camera 1, it is possible to suggest quantitatively and time-serially transition of the water content contained in the plant by displaying the graph representing the time-transition of the water content contained in leaf PT3 of plant PT on UI screen 60 of monitor 50. In addition, according to the time-transition of standardized pixel average water content index Dw contained in leaf PT3 displayed on UI screen 60 of monitor 50, plant detection camera 1 can teach the user the timing of the irrigation to leaf PT3 and the irrigation amount. The user can perform the irrigation with an appropriate irrigation amount at an appropriate irrigation timing from the graph displayed on UI screen 60 of monitor 50. Accordingly, it is possible to perform optimum cultivation control when realizing a function of the plant such as a tomato so that yield can be improved and productivity can be enhanced.

Further, according to plant detection camera 1, target range Bw of standardized pixel average water content index Dw (water content) of the plant, an initial value of the water content, and the change of the water content fell down due to the non-irrigation as an example of the application of the stress (for example, water stress) are displayed, and thus the user can grasp the water content of the plant in time series.

In addition, according to plant detection camera 1, it is possible to search the optimum irrigation amount such that standardized pixel average water content index Dw (water content) of the plant is included within target range Bw.

Further, according to plant detection camera 1, both of falling down of the water content by the non-irrigation as an example of application of the stress (for example, water stress) and rising of the water content by the irrigation are displayed, and thus the optimum irrigation amount can be more easily searched such that standardized pixel average water content index Dw is included within target range Bw.

In addition, according to plant detection camera 1, target range Bw of the water content of the plant and the change of the water content by the irrigation for maintaining the water content of the plant within the target range are displayed, and thus the irrigation with the irrigation amount can be easily performed such that the water content of the plant is included within the target range.

Further, according to plant detection camera 1, the water content contained in the plant for which the irrigation is performed by the normal irrigation, and the water content contained in the plant for which the irrigation is performed while applying the water stress are relatively compared to each other, and thus the user can efficiently and highly accurately determine appropriateness of the irrigation amount and the irrigation timing.

Modification Example 1 of First Embodiment

Figure 20:
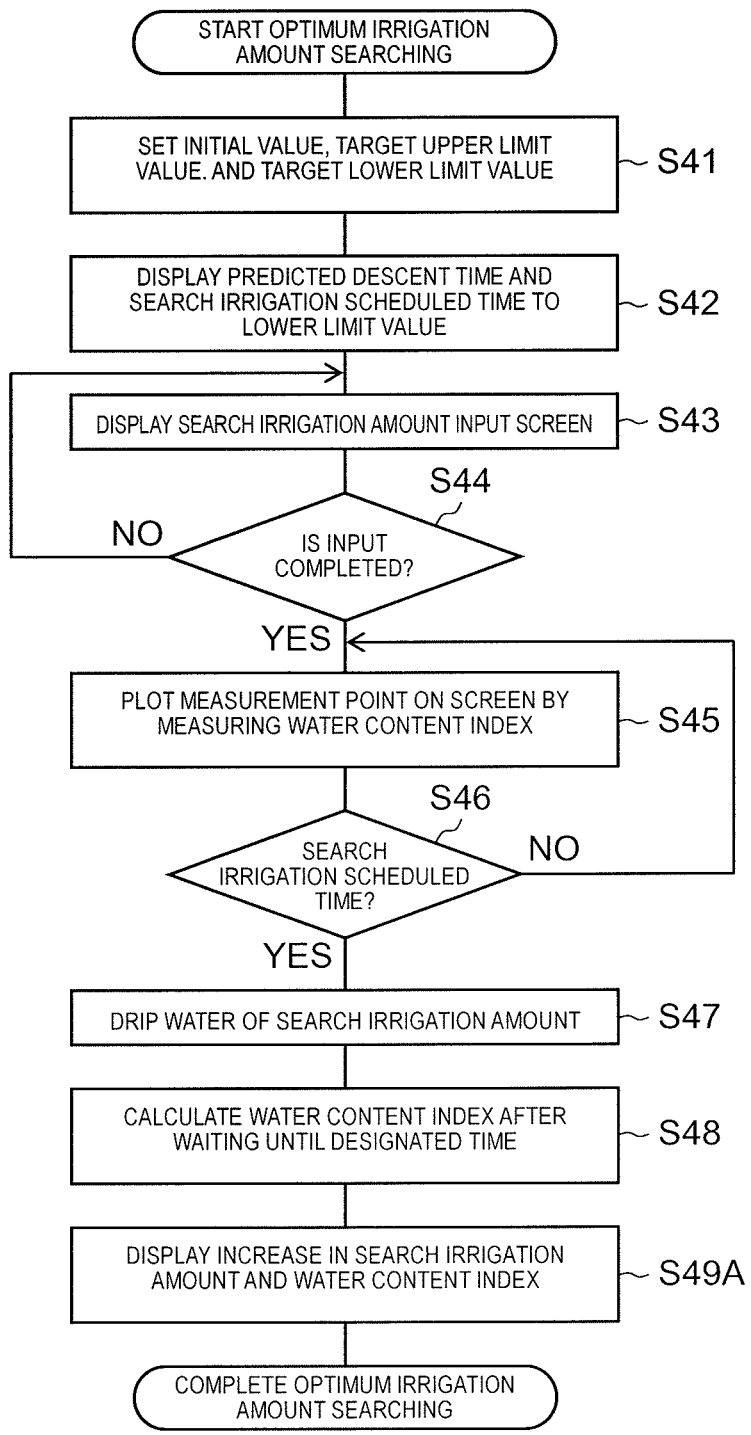
FIG. 20 is a flow chart illustrating an example of searching procedure of the optimum irrigation amount in Modification Example 1 of the first embodiment.

FIG. 20 is a flow chart illustrating an example of searching procedure of the optimum irrigation amount in Modification Example 1 of the first embodiment. The same step processing as in FIG. 15 is denoted by the same step number, and the description thereof will not be repeated. After waiting until the designated time in step S48, controller 11 calculates the water content index, and then displays the search irrigation amount and the increase in standardized pixel average water content index Dw so as to maintain the water content index within target range Bw (within the range) (S49A). Based on these displays, the user can infer the optimum water content. Thereafter, controller 11 completes the present operation.

Second Embodiment

The second embodiment describes a case where positional deviation of leaves occurs due to some influences during the continuous measurement of standardized pixel average water content index Dw in the leaf. In a case where a white reference substrate to which the leaf that is a measurement target is attached tilts due to, for example, strong wind and collision, and the positional deviation of the leaves occurs during the measurement of standardized pixel average water content index Dw in the leaf in time series, standardized pixel average water content index Dw in the leaf measured by the reflection intensity ratio due to the irradiation of the laser beam is rapidly changed.

In a case where the positional deviation of the leaf that is a measurement target occurs, data in which standardized pixel average water content index Dw in the leaf is recorded in time series is fluctuated at once, and the continuity thereof is lost, and thus, in the related art, data of standardized pixel average water content index Dw measured in time series so far is discarded, and the measurement is started again from the beginning. As a result, the acquisition efficiency of measurement data remarkably decreased.

In the second embodiment, even in a case where the positional deviation of the leaves occurs, by effectively utilizing the data measured in time series so far without discarding, the data of standardized pixel average water content index Dw in the leaf can be efficiently acquired and the increase of measurement time is suppressed.

Figure 21A:
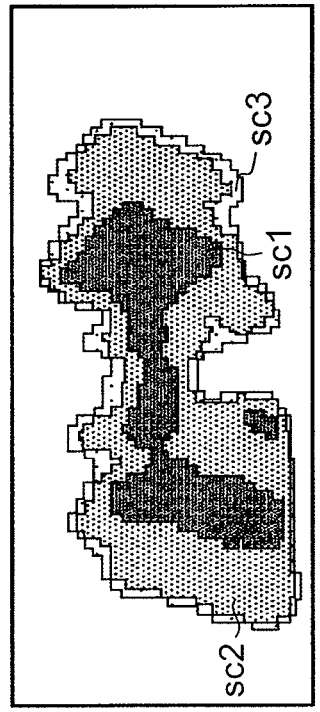
FIG. 21A is a diagram illustrating an example of an image indicating a water content in a leaf that is a measurement target, which is captured by a plant detection camera of the second embodiment, and an example of an image of a leaf before positional deviation.
Figure 21B:
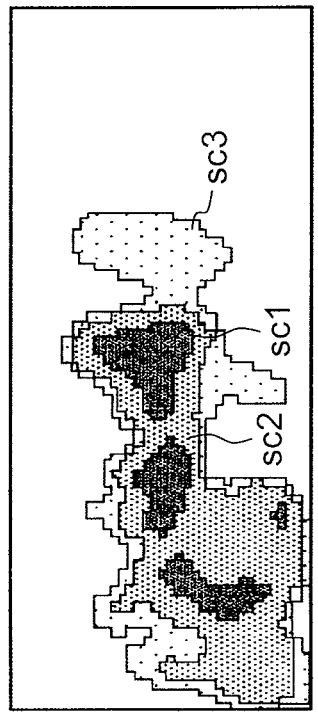
FIG. 21B is a diagram illustrating an example of an image indicating a water content in a leaf that is a measurement target, which is captured by a plant detection camera of the second embodiment, and an example of an image of a leaf after positional deviation.

FIG. 21A is a diagram illustrating an example of an image indicating a water content in a leaf that is a measurement target, which is captured by plant detection camera 1 of the second embodiment, and an example of an image of a leaf before positional deviation. FIG. 21B is a diagram illustrating an example of an image indicating a water content in a leaf that is a measurement target, which is captured by plant detection camera 1 of the second embodiment, and an example of an image of a leaf after positional deviation. In the drawings, an area which is dark and has a large number of dots is an area having a large water content. Area sc1 which is a darkest area (with the largest water content) exists inside the leaf. Area sc2 which is the next darkest area (with slightly large water content) exists around area sc1. Area sc3 which is a light area (with small water content) exists outside the leaf. In addition, compared with before the positional deviation, the size of area sc1 having a large water content is increased after the positional deviation.

Figure 22:
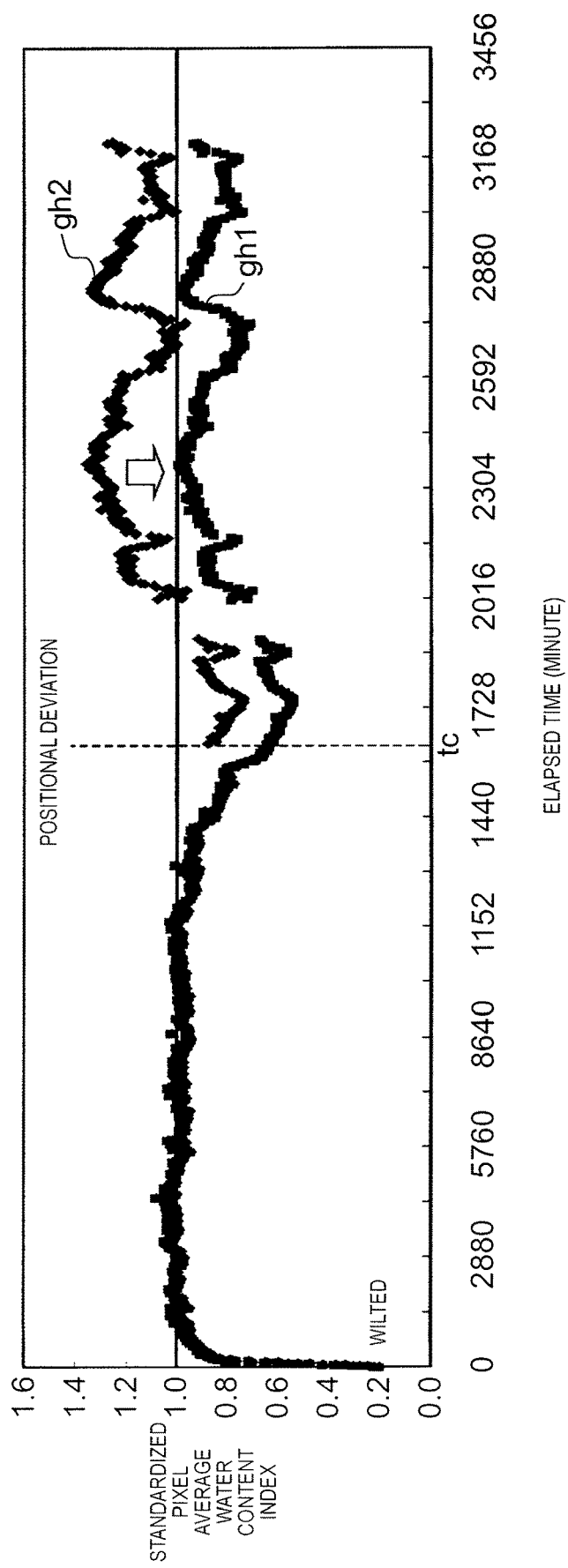
FIG. 22 is a graph illustrating an example of a time-transition of a standardized pixel average water content index in a water potential control experiment in a case where the positional deviation occurs.

FIG. 22 is a graph illustrating an example of a time-transition of standardized pixel average water content index Dw in the water potential control experiment in a case where the positional deviation occurs. This vertical axis of the graph indicates the standardized pixel average water content index similar to the first embodiment. The standardized pixel average water content index represents the water potential and represents a value corresponding to the water content contained per pixel in a captured image of the leaf of the plant. The horizontal axis of the graph represents the elapsed time in minutes.

When the positional deviation of leaves (refer to timing tc in the drawings) occurs, standardized pixel average water content index Dw is changed at once. Standardized pixel average water content index Dw in the leaf in a case where the positional deviation of leaves does not occur is changed as illustrated in graph gh1. On the other hand, standardized pixel average water content index Dw in the leaf in the case where the positional deviation of leaves occurs is changed as illustrated in graph gh2.

In the second embodiment, even in the case where the positional deviation of the leaves occurs, by performing the correction based on the following consideration, the data of standardized pixel average water content index Dw before the positional deviation of the leaves is effectively utilized, and the data of standardized pixel average water content index Dw in time series is acquired so as to maintain the continuity with the data of standardized pixel average water content index Dw after the positional deviation of the leaves.

In the following consideration, it is assumed that leaves are tilted as the positional deviation of the leaves. In this case, changing an angle as the leaves are tilted in a pan direction or a tilt direction corresponds to changing the thickness of the leaf as seen from the camera.

The water content (in other words, water potential) in the leaf is water amount contained in the leaf is proportional to standardized pixel average water content index Dw. In addition, standardized pixel average water content index Dw can be obtained from the total sum of reflection intensity ratio Ln ($I_{905}/I_{1550}$).

It is known that the reflection intensity ratio Ln ($I_{905}/I_{1550}$) is substantially proportional to (correlated with) leaf thickness t, as represented by Expression (3) based on known Lambert•Beer's law. In Expression (3), α is an absorption coefficient of water, t is a leaf thickness, C is water concentration, and β is a scattering loss term.

$$\text{Ln}(I_{905}/I_{1550}) = \alpha \cdot t \cdot C + \beta \tag{3}$$

In summary, the water content (water potential) in the leaf is represented by a linear function of standardized pixel average water content index Dw having leaf thickness t as a gradient (slope). That is, the slope of the water content in the leaf is changed with leaf thickness t.

As described above, from the fact that the change in the angle of the leaf due to the positional deviation corresponds to the change in the slope due to leaf thickness t, it is possible to obtain the data of standardized pixel average water content index Dw before the positional deviation by multiplying coefficient Q (correction coefficient) corresponding to the change (the change in the slope due to the leaf thickness t) in the leaf angle by the data of standardized pixel average water content index Dw after the positional deviation.

As a result, the data of standardized pixel average water content index Dw obtained in time series before and after the positional deviation can maintain the continuity. Here, since the acquisition of the water content immediately before and after the positional deviation is performed within a short time, the substantial water content is not changed between before and after the positional deviation.

In detail, a correction example of standardized pixel average water content index Dw before and after the positional deviation will be described. FIG. 23 is a diagram illustrating a table indicating an example of the standardized pixel average water content index before and after positional deviation correction in time series. In this table, in the graph illustrated in FIG. 22, in a case where the positional deviation occurs at the elapsed time of 16250 minutes (time 17:10), standardized pixel average water content index Dw before correction and standardized pixel average water content index Dw after correction are indicated. Here, coefficient Q corresponding to the change in the angle of the leaf is calculated by controller 11 as an example of the coefficient calculation unit, and specifically, the value is 0.7303 (=0.6416/0.8785).

Figure 24:
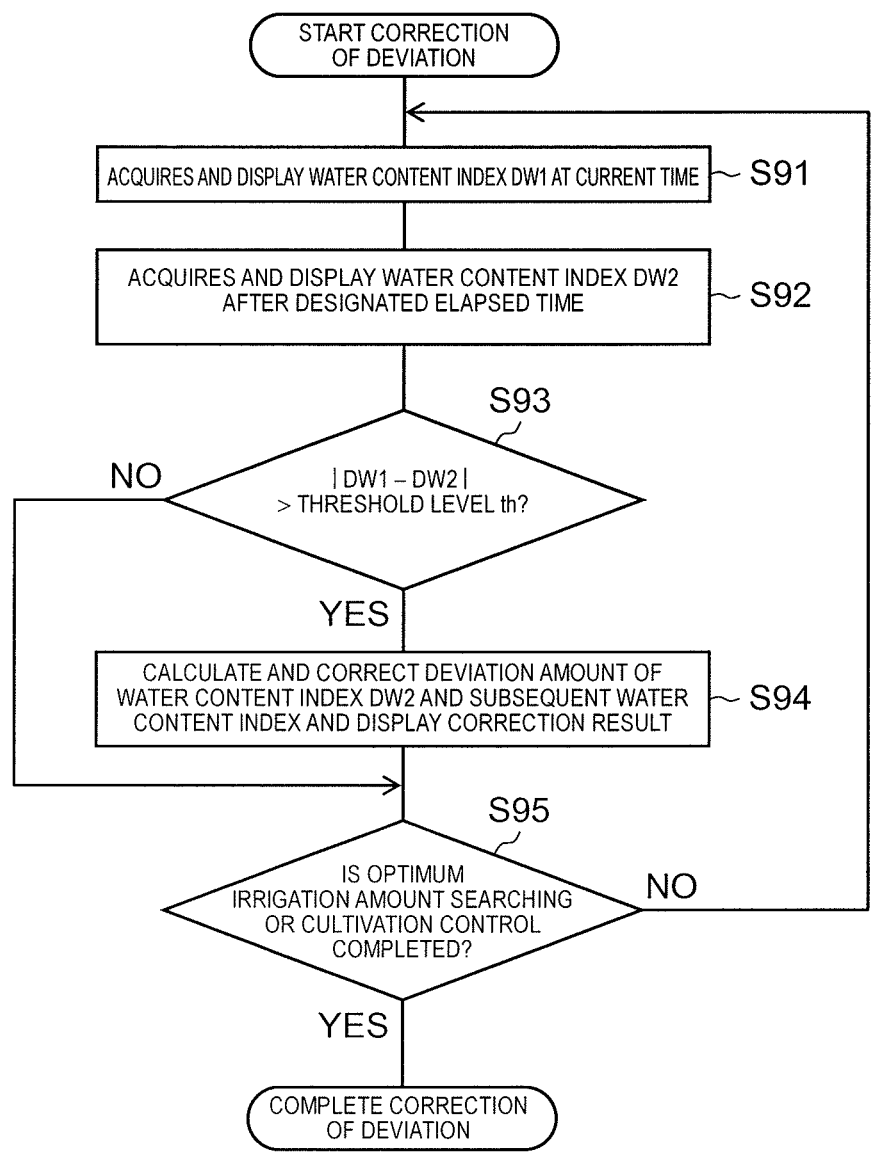
FIG. 24 is a flow chart illustrating an example of correction procedure of the positional deviation of second embodiment.

FIG. 24 is a flow chart illustrating an example of correction procedure of the positional deviation of second embodiment. Plant detection camera 1 of the second embodiment has substantially the same configuration as that of the first embodiment. The same reference numerals are used for the same constituent elements as those of the first embodiment, and a description thereof will not be repeated.

Controller 11 acquires and displays standardized pixel average water content index Dw1 at a current time on UI screen 60 (S91). Controller 11 acquires and displays standardized pixel average water content index Dw2 after designated elapsed time (for example, after 30 minutes) (S92). The designated elapsed time corresponds to a measurement interval.

Controller 11 determines whether or not the difference between standardized pixel average water content index Dw1 and standardized pixel average water content index Dw2 exceeds threshold level th (S93). This threshold level th is used for the determination of the value which is assumed to change standardized pixel average water content index Dw due to the positional deviation of the leaves.

Here, threshold level th is set in advance. At the time of setting threshold level th, controller 11 displays a deviation determining threshold level input screen. The user inputs threshold level th to the deviation determining threshold level input screen in order to determine that the positional deviation occurs. When the input is completed, controller 11 displays this input value and accepts the setting of threshold level th.

In a case where the difference between standardized pixel average water content index Dw1 and standardized pixel average water content index Dw2 does not exceed threshold level th, that is, in a case where it is assumed that the positional deviation of the leaves does not occur, controller 11 proceeds the process to step S95. On the other hand, in a case where the difference between standardized pixel average water content index Dw1 and standardized pixel average water content index Dw2 exceeds threshold level th, controller 11 determines that the positional deviation occurs, and displays the values of standardized pixel average water content index Dw2 and subsequent standardized pixel average water content index Dw on UI screen 60 by correcting the deviation amount (S94).

After that, controller 11 determines whether to complete the optimum irrigation amount searching control, to complete the cultivation control, or not to complete the cultivation control (S95). In the case where the optimum irrigation amount searching control is not completed, and the cultivation control is not completed, controller 11 returns to the process of step S91. On the other hand, in the case where the optimum irrigation amount searching control is completed, or the cultivation control is completed, controller 11 completes the present operation.

In this way, in plant detection camera 1 of second embodiment, controller 11 as an example of the detection unit detects the positional deviation of the plant. In a case where the positional deviation of the plant is detected, controller 11 calculates coefficient Q (correction coefficient) multiplied by the water content index after positional deviation based on the water content index in before and after the positional deviation. Controller 11 corrects the positional deviation amount by multiplying coefficient Q by the water content index after the positional deviation, and displays the result corrected such that water content index before the positional deviation and the water content index after the positional deviation maintain the continuity on UI screen 60 of monitor 50.

As a result, even in a case where the positional deviation of the leaves occurs, it is possible to maintain the continuity of standardized pixel average water content index Dw in the leaf measured in time series. Accordingly, the measured standardized pixel average water content index Dw value in the leaf can be meaningfully and effectively utilized without being wasted This makes it possible to efficiently acquire data of standardized pixel average water content index Dw in the leaf in time series, and suppress the increase in the measurement time of standardized pixel average water content index Dw even in a case where the positional deviation occurs on the way.

Modification Example 1 of Second Embodiment

In the second embodiment, the positional deviation of the leaves is determined based on whether or not the difference of standardized pixel average water content index Dw exceeds threshold level th; however, in Modification Example describes a case where the positional deviation of the leaves is physically detected.

Figure 25B:
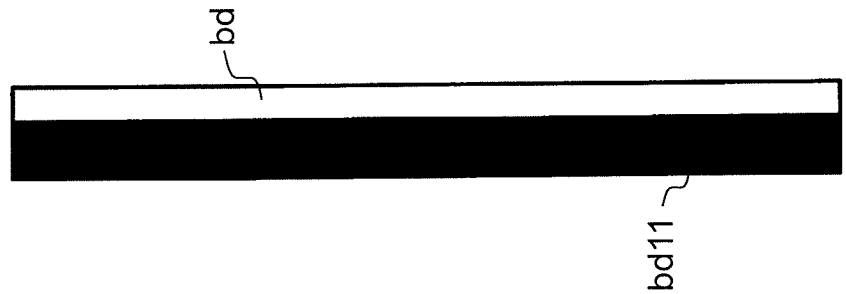
FIG. 25B is a diagram illustrating the white reference substrate used for detecting the positional deviation in Modification Example 1 of the second embodiment, and a side view of the white reference substrate as illustrated in FIG. 25A.
Figure 25A:
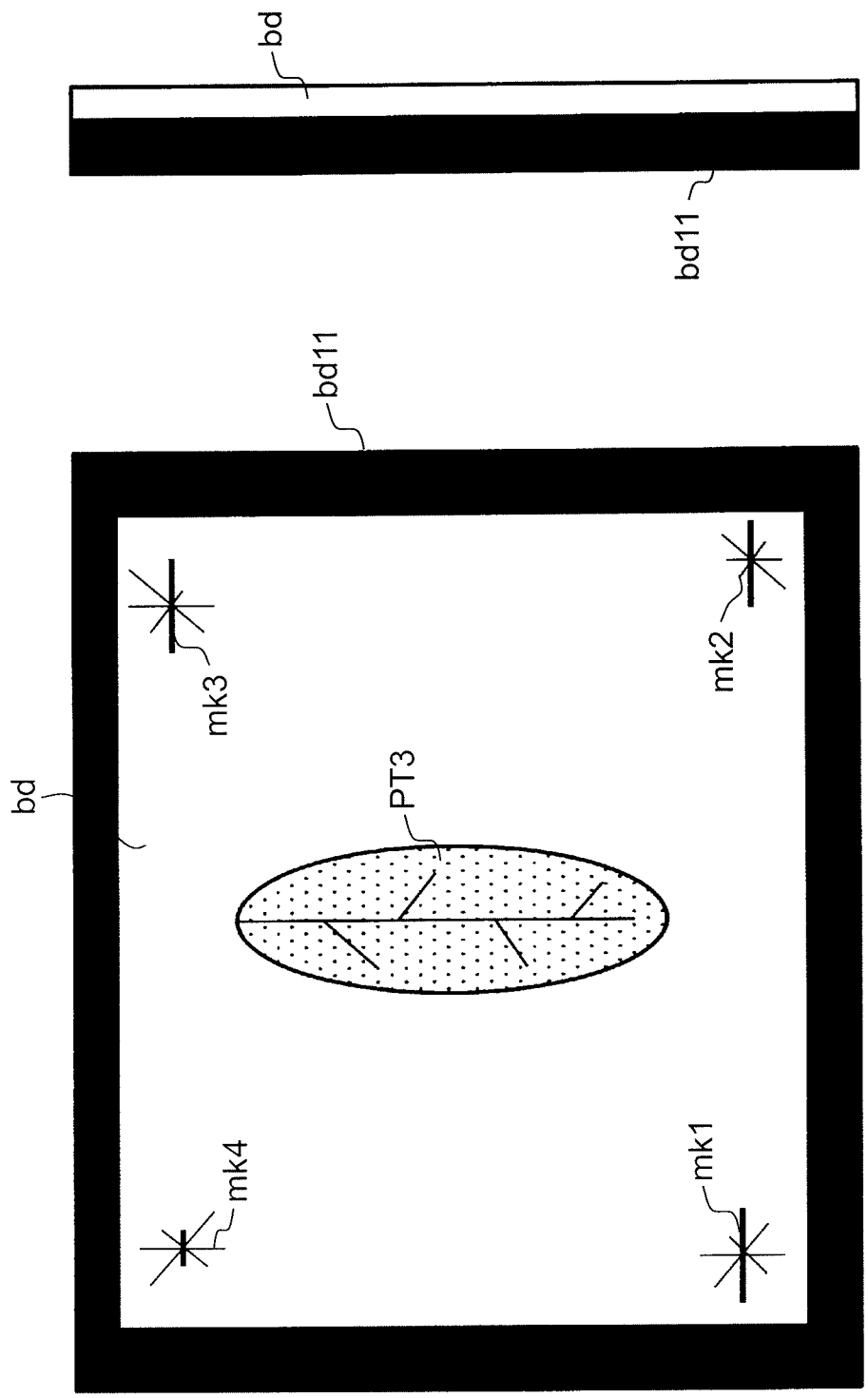
FIG. 25A is a diagram illustrating a white reference substrate used for detecting the positional deviation in Modification Example 1 of the second embodiment, and a front view of the white reference substrate.

FIG. 25A is a diagram illustrating white reference substrate bd used for detecting the positional deviation in Modification Example 1 of the second embodiment, and a front view of white reference substrate bd. FIG. 25B is a diagram illustrating white reference substrate bd used for detecting the positional deviation in Modification Example 1 of the second embodiment, and a side view of white reference substrate bd as illustrated in FIG. 25A.

At the periphery of white reference substrate bd, frame bd 11 of black rectangle having a shape like a picture frame is provided. In addition, marks mk 1 to mk 4 of rice marks are drawn at four corners of the surface (front surface) of white reference substrate bd. Also, leaf PT3 is attached to the center of the surface of white reference substrate bd.

When capturing leaf PT3 attached to white reference substrate bd with plant detection camera 1, parallelism between white reference substrate bd and the finder of plant detection camera 1 is obtained by aligning black frame bd 11 with a finder frame. By capturing white reference substrate bd in this state, each distance between marks mk 1 to mk 4 is compared with the reference distance registered in advance. This reference distance is a distance between marks mk 1 to mk 4 captured in a case where white reference substrate bd is set to be parallel to plant detection camera 1. In a case where each distance between marks mk 1 to mk 4 is shorter than the reference distance, it is determined that white reference substrate bd is tilted to cause the positional deviation.

For example, it is found that as the distance between mark mk 1 and mark mk 4 is shorter than the reference distance, a tilt angle is larger. It is found that as the distance between mark mk 1 and mark mk 2 is shorter than the reference distance, a pan angle is larger.

In this way, it is possible to physically detect positional deviation of the leaves and to measure the positional deviation amount. Furthermore, by registering coefficient Q corresponding to the measured positional deviation amount, when performing the process of multiplying the data of standardized pixel average water content index Dw after the positional deviation, there is no need to use data of standardized pixel average water content index Dw before and after correction. Therefore, the processing load can be reduced.

Modification Example 2 of Second Embodiment

Figure 26:
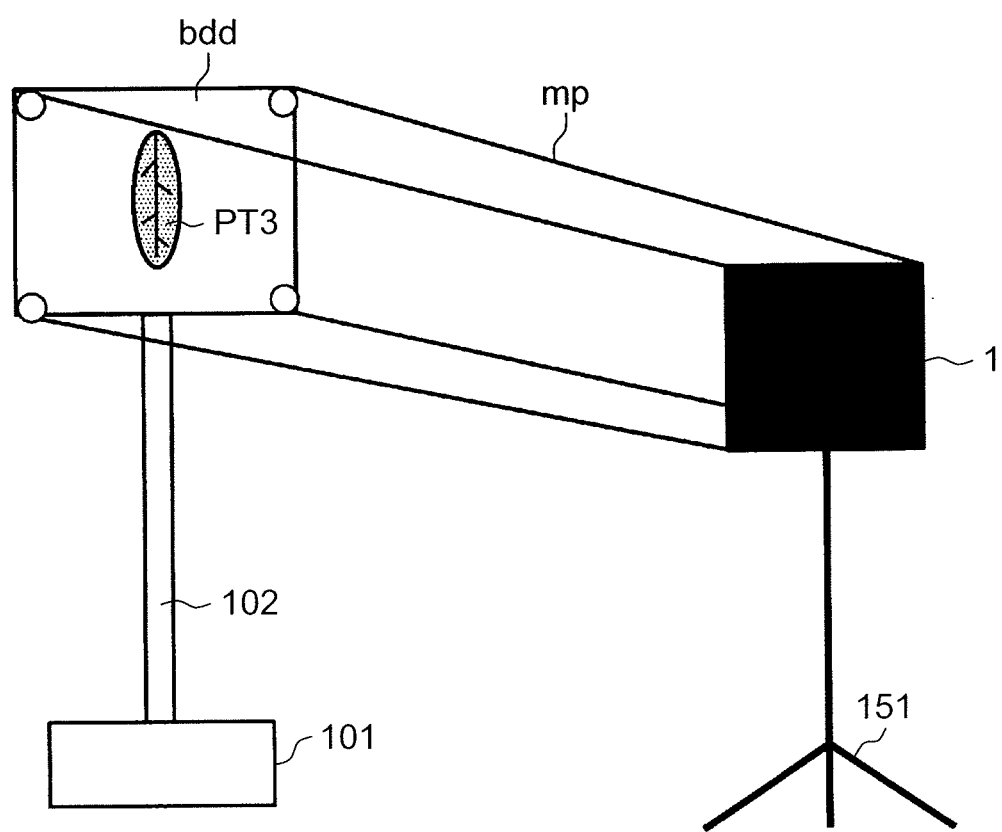
FIG. 26 is a diagram illustrating an example of mechanical disposition of the white reference substrate and the plant detection camera in Modification Example 2 of the second embodiment.

FIG. 26 is a diagram illustrating an example of mechanical disposition of white reference substrate bdd and plant detection camera 1 in Modification Example 2 of the second embodiment. White reference substrate bdd is mounted as a stand attached on bar 102 standing on base 101. Plant detection camera 1 is fixed to tripod 151. Further, white reference substrate bdd is mechanically connected and fixed to plant detection camera 1 by connecting member mp such as a wire or a bar. In the case where the positional deviation occurs on white reference substrate bdd, the change is transferred to plant detection camera 1 as it is. For example, in the case where large positional deviation occurs, a large change occurs in an image captured by plant detection camera 1.

In a case where the degree of correlation of images captured in time series becomes equal to or smaller than a threshold level, that is, in a case where the similarity between the previous frame image and the current frame image is significantly deteriorated, plant detection camera 1 may determine that the positional deviation occurs on white reference substrate bd. As a result, it is possible to relatively easily detect the positional deviation of white reference substrate bd.

In addition, a method for detecting the positional deviation is not limited to the above method. For example, plant detection camera 1 may be equipped with an acceleration sensor for sensing impact. When the positional deviation occurs on white reference substrate bdd, the change of white reference substrate bdd is transferred to plant detection camera 1 via connecting member mp. In a case where the impact is detected by the acceleration sensor mounted on plant detection camera 1, it may be detected that the positional deviation occurs on white reference substrate bdd.

Third Embodiment

In the third Embodiment, plant detection camera 1 uses an external standard sample as at least one external sample attached to the vicinity of the true leaf of white reference substrate bd at the time of deriving water content (for example, relative water content) of the leaf of tomato (hereinafter, referred to as "true leaf") as an observing portion. The relative water content rate of the true leaf is calculated by using a calculation expression described below by using a value of the relative water content in a case where the relative water content of at least one external standard sample is known. Hereinafter, the external standard sample is referred to as "artificial leaf" distinguishing from "true leaf" which is an original leaf. Specifically, plant detection camera 1 radiates white reference substrate bd on which the true leaf and a plurality of artificial leaves are attached with two kinds of near infrared laser beams (that is, reference beam LS1 and measuring beam L52) which are different from the wavelength. Plant detection camera 1 derives and calculate, as an index indicating the water content of the true leaf, water content rate (also referred to as a relative water content) by using the intensity of the reflection light reflected on the true leaf and the intensity of the reflection light reflected on each of the artificial leaves. Also, as will be described below, the artificial leaf contains fructose without water. In the following description, water content rate (water content) contained in the true leaf is referred to as "relative water content of the true leaf", and thus a fructose content rate (fructose content) contained in the artificial leaf is referred to as "relative water content of the artificial leaf".

Note that, even in the third Embodiment, an internal configuration of plant detection camera 1 is the same as the internal configuration of plant detection camera 1 of the first embodiment, and thus, the same reference numerals are used to denote the same components, and the description will be simplified or will not be repeated.

Figure 30:
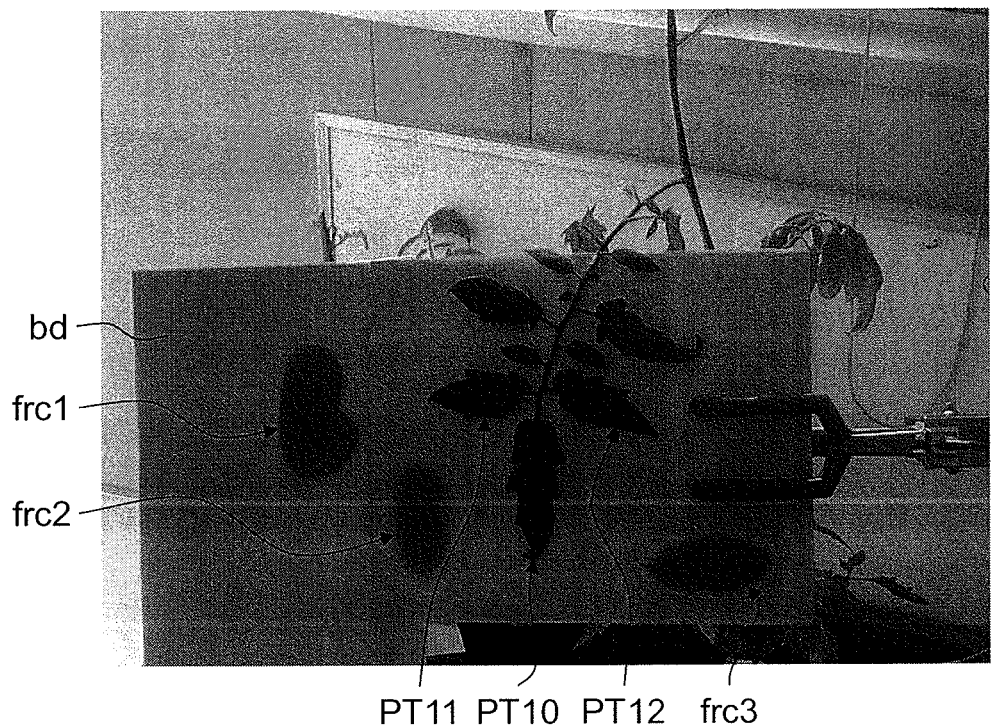
FIG. 30 is a diagram illustrating an example of a measurement state of the water content of a leaf (true leaf) of a tomato in a third embodiment.
Figure 31:
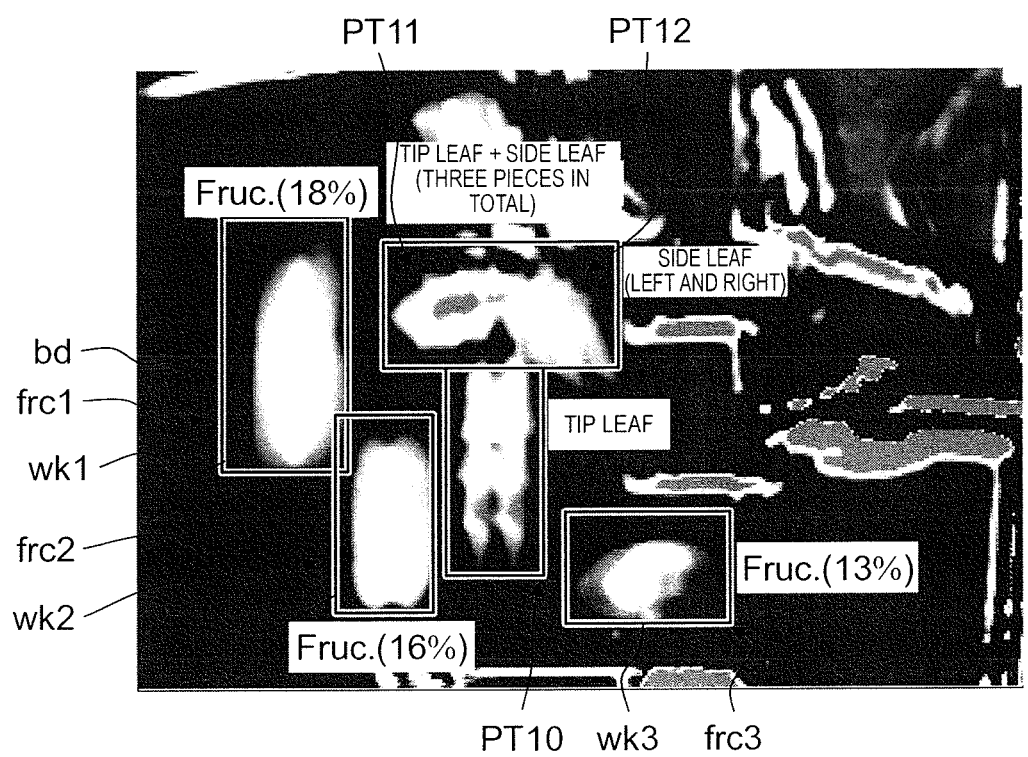
FIG. 31 is a diagram of visualized near infrared absorption image data illustrating an example of distribution of water content of a true leaf and an artificial leaf corresponding to the measurement state of FIG. 30.

First, in the third Embodiment, a measurement atmosphere of laboratory room in which the true leaf and the plurality of artificial leaves are attached on the white reference substrate will be described with reference to FIG. 30 and FIG. 31. FIG. 30 is a diagram illustrating an example of a measurement state of the water content of a leaf (true leaf) of a tomato in the third embodiment. FIG. 31 is a diagram of visualized near infrared absorption light image data illustrating an example of distribution of the water content of the true leaf and the artificial leaf corresponding to the measurement state of FIG. 30.

On rectangular white reference substrate bd, true leaves PT10, PT11, and PT12 and the plurality of artificial leaves frc1, frc2, and frc3 that are observation targets of plant detection camera 1 of the present embodiment. Hereinafter, true leaf PT10 may be also referred to as "tip end leaf", and true leaves PT11 and PT12 may be also referred to as "side leaf". Note that, true leaves PT10, PT11, and PT12 may be fixed to white reference substrate bd by using, for example, with Cellotape (registered trademark), or may be fixed with PET film or wire-netting.

First, the artificial leaf will be described. The artificial leaf is, for example, created by the following steps.

[Step 1]

First, the liquid of a viscous amine curing agent (a specially modified silicone resin) and fructose are mixed so as to be uniform. Here, in the present embodiment, the plurality of artificial leaves are created, and each of the artificial leaves has different fructose content with respect to the amount of hardened total epoxy resins. For example, as illustrated in FIG. 31, fructoses (that is, 13%, 16%, and 18%) with three different content rate is prepared in advance.

[Step 2]

An epoxy resin liquid is mixed with a mixture prepared in [Step 1]. With this, an amine curing agent and an epoxy resin promptly start a chemical reaction at room temperature, and curing starts. Note that, the epoxy resin liquid used in [Step 2] is, for example, Epoxy Resin Elastic Adhesive EP001 from Cemedine Co., Ltd. is used, but is not limited to this.

[Step 3]

Three kinds of mixtures as a result of curing in [Step 2] are placed so as to be thinly extended on white reference substrate bd and then covered with a PET film to cover the entire surface. After about 24 hours at room temperature, artificial leaves frc1, frc2, and frc3 are attached to white reference substrate bd in a state of being fixed with the PET film.

Figure 32:
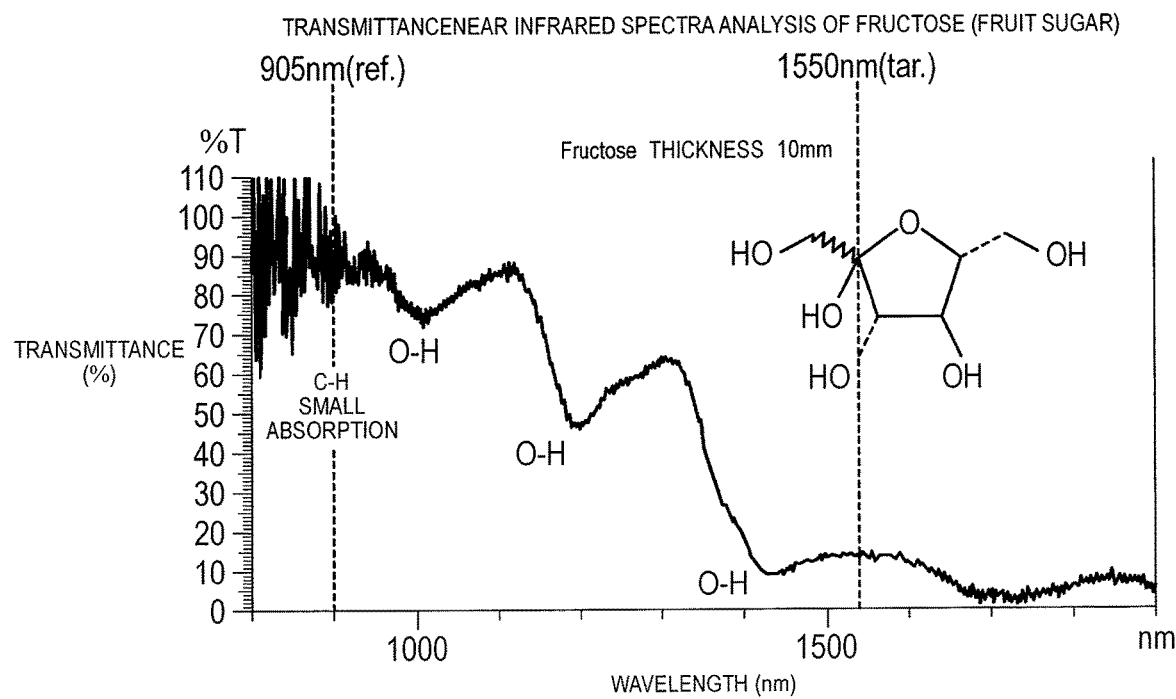
FIG. 32 is a graph illustrating an example of the near infrared spectra of fructose.

FIG. 32 is a graph illustrating an example of the near infrared spectra of fructose (fruit sugar). A horizontal axis of FIG. 32 indicates wavelength (nm), and a vertical axis of FIG. 32 indicates transmittance (transparency) (%). As illustrated in FIG. 32, similar to the transmittance of water ($H_2O$), the transmittance of fructose with reference beam LS1 having a wavelength of 905 nm is almost 100%, and thus reference beam LS1 having the wavelength of 905 nm has a characteristic in which light tends not to be absorbed in both water and fructose (refer to ref. (=reference) FIG. 32). Similarly, since the transmittance of fructose of measuring beam LS2 having a wavelength of 1550 nm is close to 10% similar to the transmittance of water ($H_2O$), in other words, since the peaks of easily absorbable wavelengths are substantially coincident, it is understood that measuring beam LS2 having the wavelength of 1550 nm has a characteristic in which light tends not to be absorbed in both water and fructose (refer to tar. (=target) in FIG. 32).

That is, in the present embodiment, applying fructose as an example of a main component of the artificial leaf as an external standard sample is due to the following reasons. As an example of chemical properties, fructose (that is, fruit sugar) has near infrared spectra (absorption spectrum) similar to that of water ($H_2O$), as illustrated in FIG. 32. The reason for this is that chemical structural formula of fructose is known as illustrated in, for example, FIG. 32, a ratio of a hydroxyl group (that is, an OH group which is a hydroxyl group) constituting water contained in the true leaf is high in the entire chemical structural formula, and thus a molar extinction coefficient is large, a vapor pressure is lower than that of water, and the fructose content does not change due to evaporation or the like at normal temperature and normal pressure, so that the reliability of the measurement value of the fructose content is high.

Furthermore, the use of epoxy resin as an example of the main components of artificial leaves as the external standard sample is due to the following reasons.

Unlike fructose, an epoxy resin has a small absorption of near infrared rays based on an OH group which is a hydroxyl group in a chemical structural formula, has no water solubility, is strong against ultraviolet rays, and hardly peels off, and the composition thereof does not change with time, and thus the stability is high.

Therefore, as the external standard sample of the present embodiment, by solidifying the fructose having water solubility and the epoxy resin having little water solubility with an amine curing agent, even when measurement is being performed in an experiment, for example, it is possible to obtain an artificial leaf in which the shape and chemical properties are less likely to change over time.

In addition, as illustrated in FIG. 30 and FIG. 31, true leaves PT10, PT11, and PT12 and artificial leaves frc1, frc2, and frc3 are closely arranged, and thus as described below, are easily affected by the same influence of the external light (for example, sunlight).

As illustrated in FIG. 31, artificial leaf frc1 is attached to white reference substrate bd so as to be sandwiched between PET films having the size of frame wk1. Similarly, artificial leaf frc2 is attached to white reference substrate bd so as to be sandwiched between PET films having the size of frame wk2. Artificial leaf frc3 is attached to white reference substrate bd so as to be sandwiched between PET films having the size of area wk3.

Further, in FIG. 31, the amount of the OH group corresponding to the water content (for example, relative water content) of true leaf PT10 (that is, tip end leaf) is a value close to the amount of the OH group corresponding to fructose content of artificial leaf frc2 (relative water content of artificial leaf frc2), true leaf PT11 (that is, the side leaf on the left side of paper surface in FIG. 31) has a large amount of the water content (for example, relative water content), and the amount of the OH group corresponding to the water content (for example, relative water content) of true leaf PT12 (that is, the side leaf on the left side of paper surface in FIG. 31) is a value close to the amount of the OH group corresponding to fructose content of artificial leaf frc1 (relative water content of artificial leaf frc2).

Figure 33:
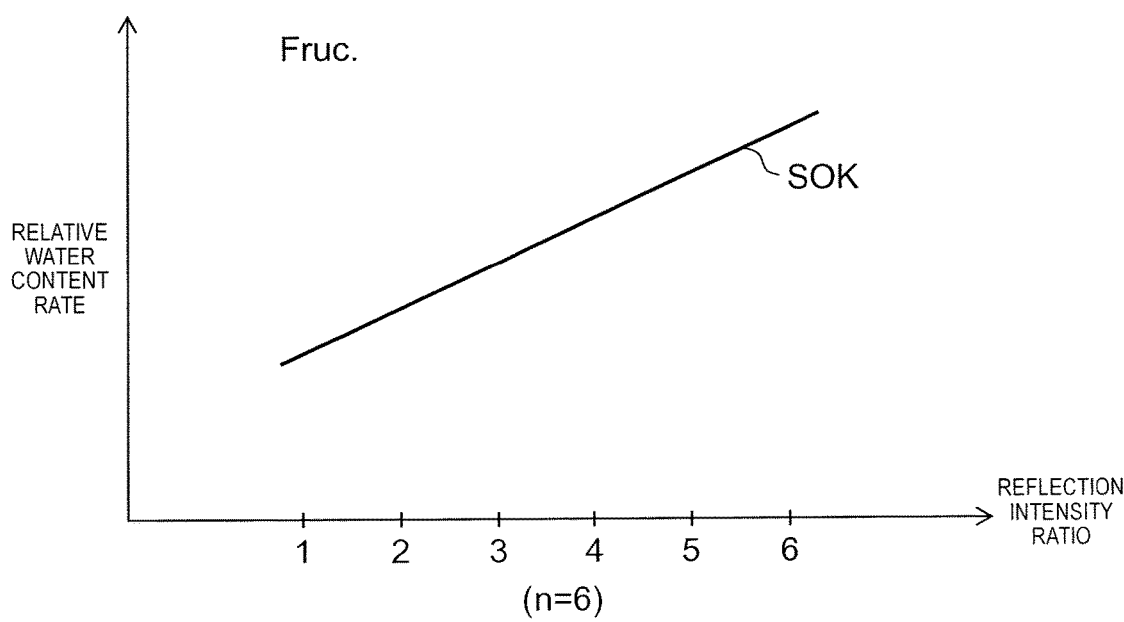
FIG. 33 is a graph illustrating a correlation between a reflection intensity ratio and relative water content rate of six kinds of artificial leaves.

FIG. 33 is a graph illustrating a correlation between a reflection intensity ratio and relative water content rate of six kinds of artificial leaves. In FIG. 30 and FIG. 31, for example, three kinds of artificial leaves are illustrated; however, six kinds of artificial leaves may be used as illustrated in FIG. 33. In the present embodiment, as illustrated in FIG. 33, there is a linear correlation between the reflection intensity ratio and the relative water content (in other words, the fructose content in the artificial leaf) as an index indicating the fructose content in the artificial leaf (refer to line SOK in FIG. 33). That is, as the reflection intensity ratio of the fructose in the artificial leaf is increased, the relative water content (in other words, the fructose rate contained in the artificial leaf) of the artificial leaf is increased. Of course, as illustrated in FIG. 30 and FIG. 31, also regarding three kinds of artificial leaves, there is correlation between the reflection intensity ratio and water content.

Next, in a case where the relative water content of each of true leaves PT10, PT11, and PT12 and artificial leaves frc1 and frc2 are not clear, an experiment for calculating each relative water content by deriving the reflection intensity ratio (average water content index) of each of true leaves PT10, PT11, and PT12, and artificial leaves frc1 and frc2, and the experimental result will be described with reference to FIG. 34 to FIG. 38.

Figure 34:
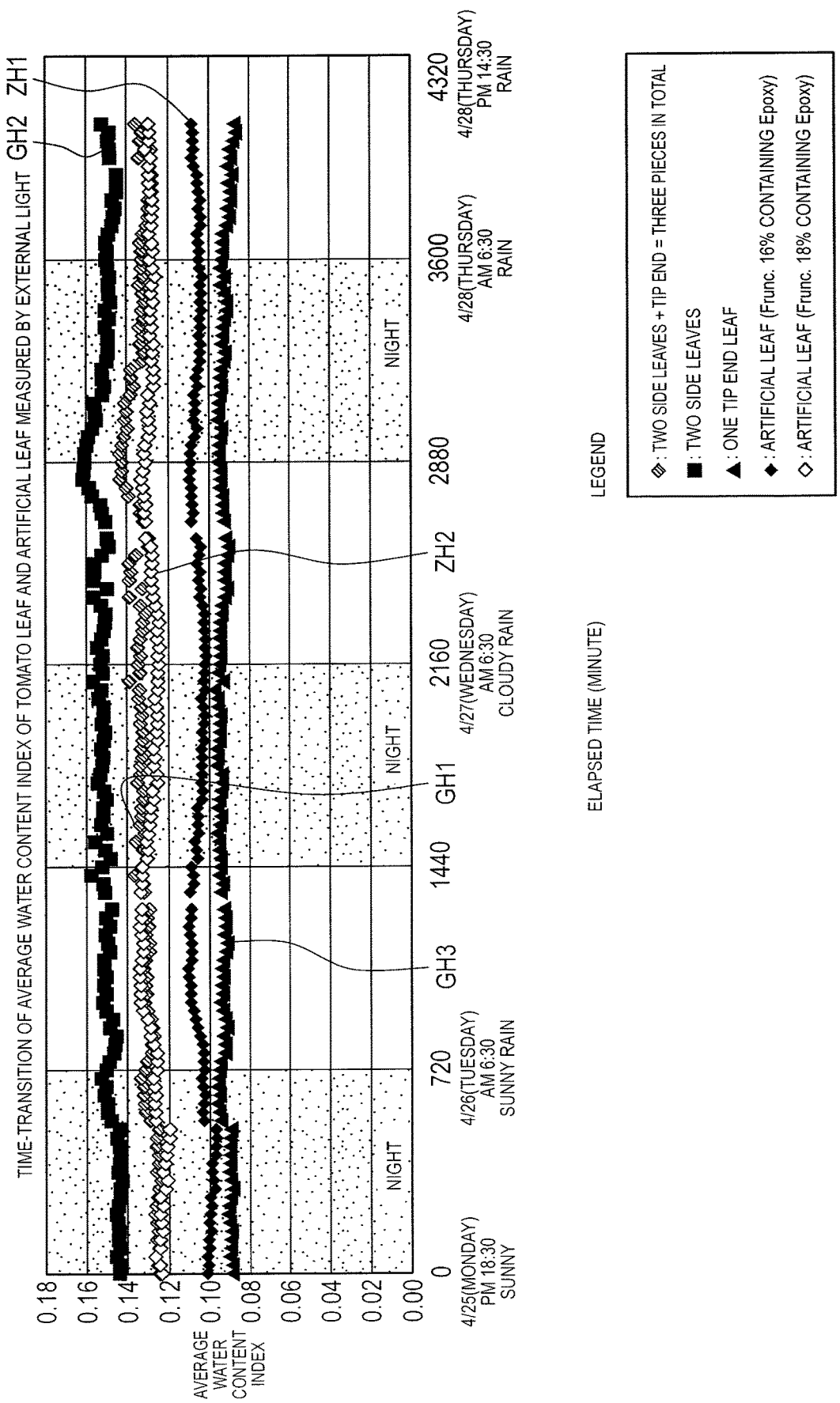
FIG. 34 is a graph illustrating an example of a time-transition of an average water content index of the true leaf and the artificial leaf measured inside and in the vicinity of a window of laboratory room where external light falls.
Figure 35:
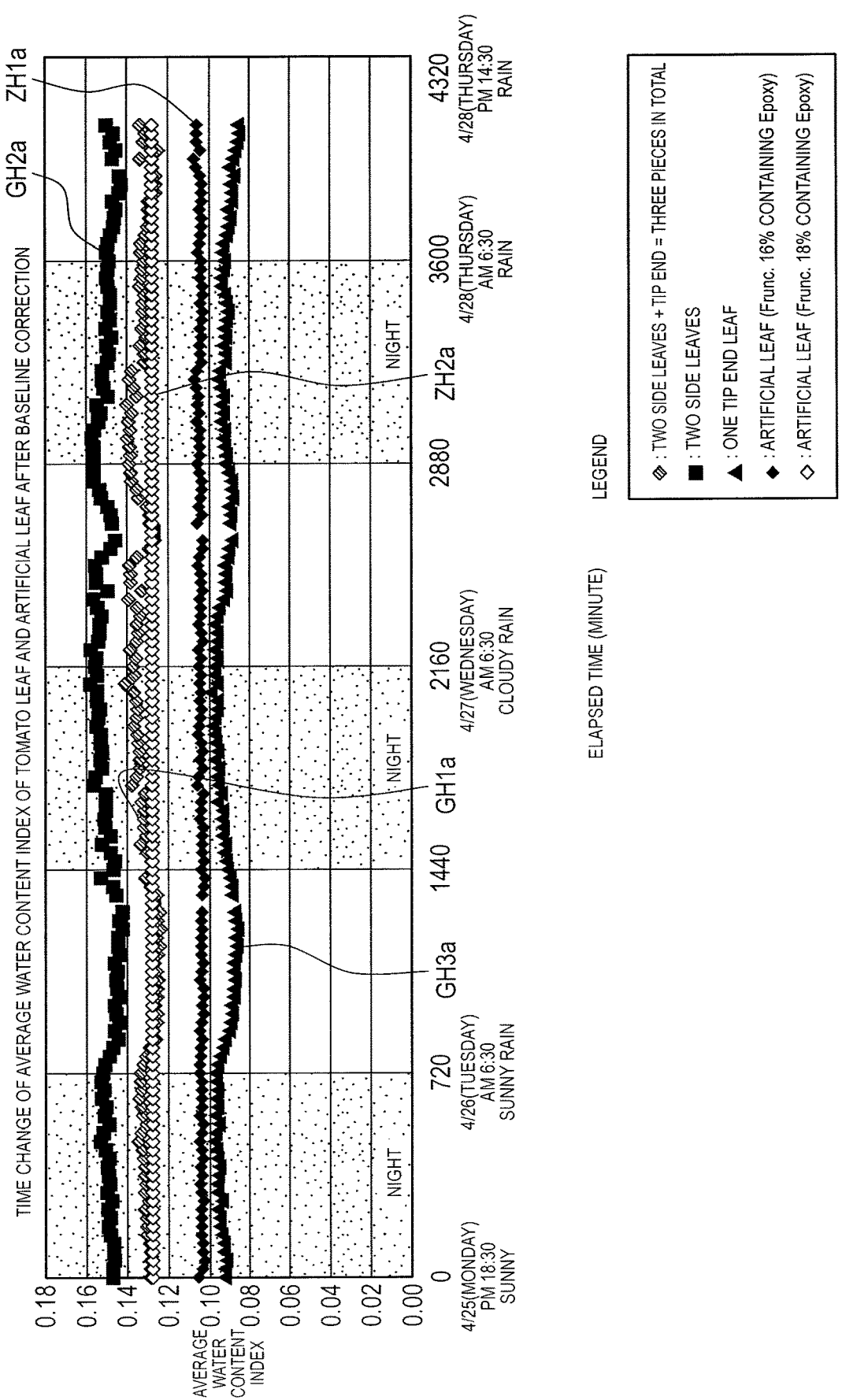
FIG. 35 is a graph illustrating an example of the time-transition of the average water content index of the true leaf and the artificial leaf after a baseline correction based on a measured value at a certain time of the average water content index in the artificial leaf containing 16% of fructose with respect to the time-transition of the average water content index as illustrated in FIG. 34.
Figure 36:
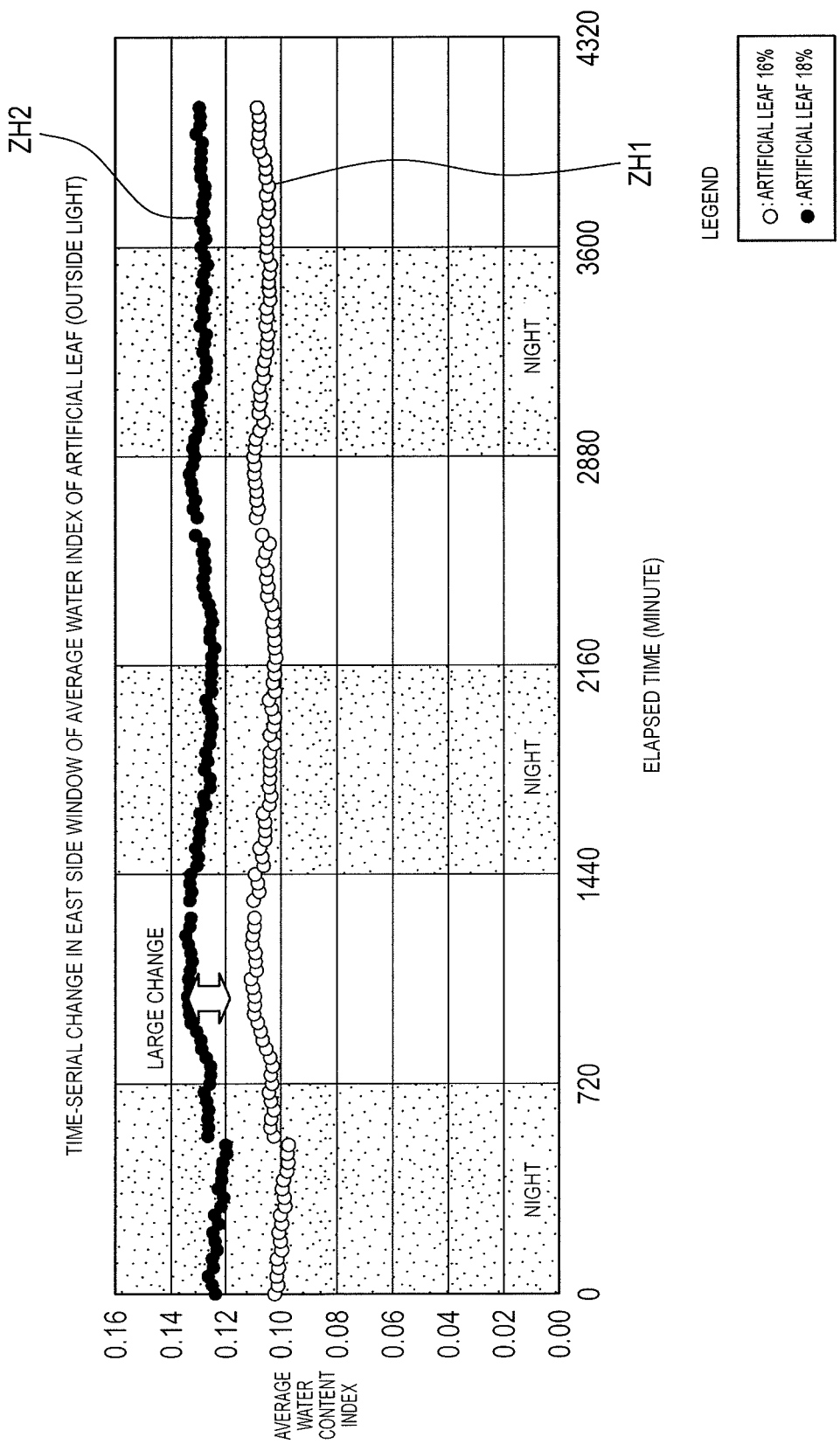
FIG. 36 is a graph illustrating an example of the time-transition of the average water content index of the artificial leaf illustrated in FIG. 34.
Figure 37:
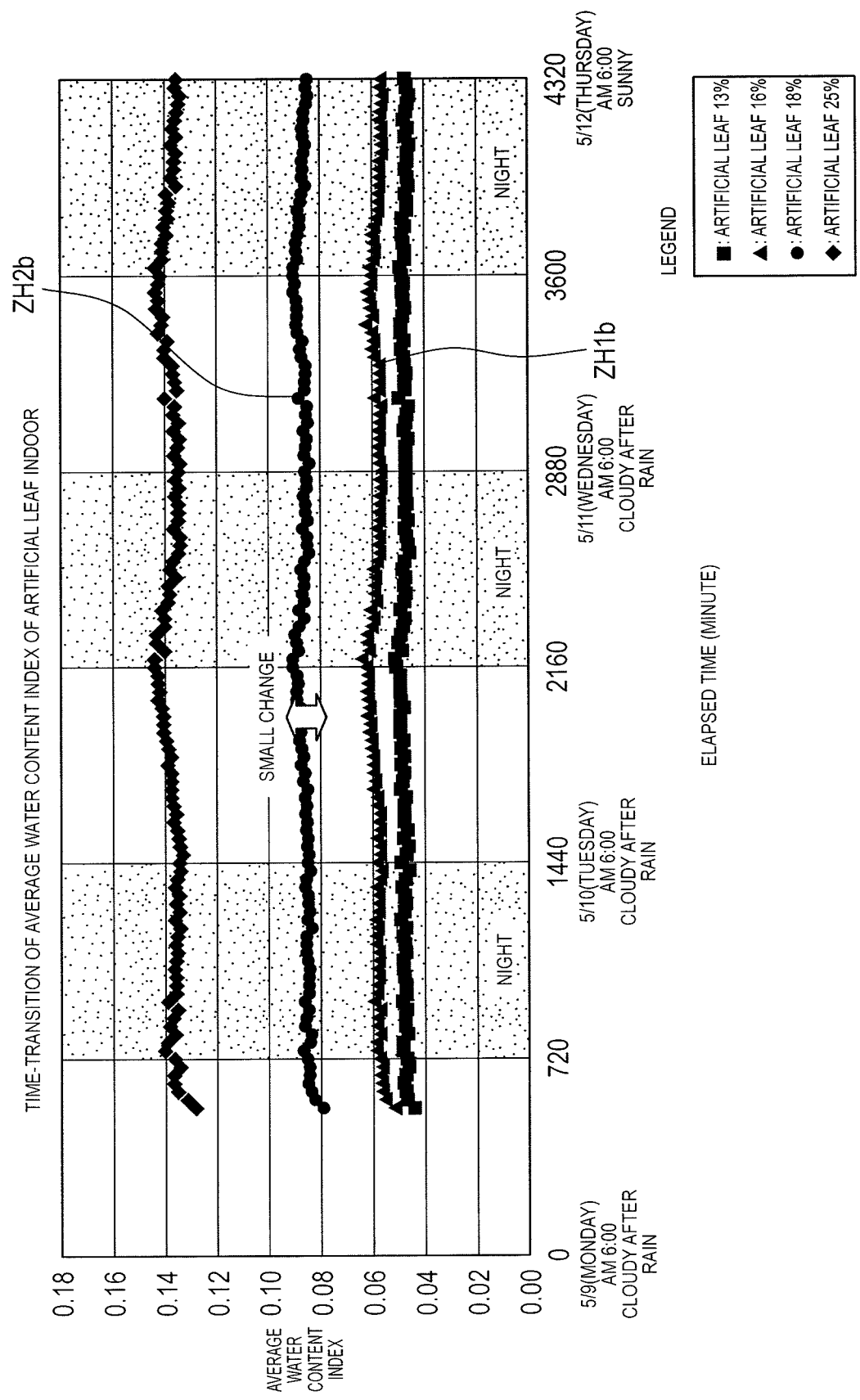
FIG. 37 is a graph illustrating the time-transition of the average water content index of the artificial leaf measured inside laboratory room where is hard to be affected by the external light.

FIG. 34 is a graph illustrating an example of a time-transition of the average water content index of true leaves PT10, PT11, and PT12 and artificial leaves frc1 and frc2 measured inside and in the vicinity of the window of laboratory room where external light falls. FIG. 35 is a graph illustrating an example of the time-transition of the average water content index of true leaves PT10, PT11, and PT12 and artificial leaves frc1 and frc2 after a baseline correction based on a measured value at a certain time of the average water content index in artificial leaf frc2 containing 16% of fructose with respect to the time-transition of the average water content index as illustrated in FIG. 34. FIG. 36 is a graph illustrating an example of the time-transition of the average water content index of artificial leaves frc1 and frc2 illustrated in FIG. 34. FIG. 37 is a graph illustrating the time-transition of the average water content index of the artificial leaves frc1 and frc2 measured inside laboratory room (indoor) where is hard to be affected by the external light falls.

The horizontal axis of FIG. 34 to FIG. 37 indicates the elapsed time (minute), and the vertical axis of FIG. 34 to FIG. 37 indicated the average water content index. In the experiment, the measurement of the reflection intensity ratio and the relative water content of true leaves PT10, PT11, and PT12 and the reflection intensity ratio and relative water content of the artificial leaves frc1 and frc2 was started at about 6:30 pm on Monday, Apr. 25, 2016 and completed at about 2:30 pm on Thursday 28th, April.

In the experimental result of FIG. 34, the measurement was performed inside and in the vicinity of the window of laboratory room where external light (for example, sunlight) falls, and thus, due to the influence of the external light (that is, the fact that sunlight is received by plant detection camera 1 and a temperature change of the true leaf and the artificial leaf by the sunlight), a value obtained by adding a certain background to the value of each average water content index as illustrated in FIG. 34 is obtained.

In document "Development of a calibration equation with temperature compensation for determining the Brix value in intact peaches" (S. Kawano et al., J. Near Infrared Spectrosc. 3, 211-218 (1995)), a technique for correcting shift of the absorption spectrum based on a hydrogen bond of a substance having an OH group such as water or saccharide to the lower wavelength side depending on the temperature is described. Here, such temperature properties are also considered as an addition for the background (including minus components).

Therefore, due to the influence of the external light described above, illuminance and movement of the sunlight change with time, and the angular dependence of the reflection light and the temperature change are observed, and thus, the average water content index of the artificial leaf, which is supposed to obtain a constant value (refer to characteristics ZH1 and ZH2 in FIG. 34). Characteristic ZH1 represents the time-transition of the average water content index of artificial leaf frc2 having 16% of fructose content. Characteristic ZH2 represents the time-transition of the average water content index of artificial leaf frc2 having 18% of fructose content.

In addition, characteristic GH3 indicates a time-transition of the average water content index of one true leaf PT10 (that is, tip end leaf). Characteristic GH2 indicates a time-transition of the average water content index of two side leaves (that is, true leaves PT11 and PT12). Characteristic GH1 indicates a time-transition of the average water content index of total three true leaves of one true leaf PT10 (that is, tip end leaf) and two side leaves (that is, true leaves PT11 and PT12).

Accordingly, the measured value (that is, average water content index) of each of the artificial leaves is changed with time, it is preferable to perform correction such that the measured value becomes a constant value. Here, the correction such that the measured value of each of the artificial leaves becomes a constant value (hereinafter, also referred to as "baseline correction") will be described with reference to FIG. 36 and FIG. 37.

In FIG. 36, only the time-transition of the measured values (that is, average water content index) of two kinds of artificial leaves frc1 and frc2 as illustrated in FIG. 34 is extracted and illustrated. As described above, it is considered that changing the measurement values of artificial leaves frc1 and frc2 with time is due to the angle dependence based on the time-transition of the movement of the sun and a temperature change based on the change of the illuminance of the sun with the influence of external light (for example, sunlight). Therefore, as illustrated in FIG. 36, for example, in characteristic ZH2 of artificial leaf frc1, the amount of displacement of the average water content index is large with time.

The experimental result as illustrated in FIG. 36 is obtained from the experiment conducted inside and in the vicinity of the window of laboratory room where external light falls; whereas the experimental result as illustrated in FIG. 37 is obtained from the experiment conducted inside laboratory room (for example, a dark room) where the external light is not so much applied. Compared to FIG. 36, as illustrated in FIG. 37, for example, characteristic ZH2b of artificial leaf frc1 has a small amount of the displacement of the average water content index with time. Similarly, characteristic ZH1b of artificial leaf frc2 also has a small amount of displacement of the average water content index over time. In other words, it is possible to suppress time-transition of the average water content index of each of artificial leaves frc1 and frc2 due to the influence of the external light.

Here, in FIG. 34 or FIG. 36, threshold level setter/water content index detector 27a of plant detection camera 1 subtract the difference between the each measured value and the measured value (average water content index) in time zone, for example, before the sunrise from the dawn (for example, 3600 minutes illustrated in FIG. 36) Value (average water content index) is subtracted from each measured value. The time zone before the sunrise from the dawn is an example of a time zone in which it is hard to be affected by external light (for example, sunlight). As a result, the plant detection camera 1 can perform the baseline correction, and correct the time-transition of each of the measured values of artificial leaves frc1 and frc2 to be substantially constant, as illustrated in FIG. 35. In addition, the reason for selecting and describing the measured value at, for example, 3600 minutes as the time zone before the sunrise from the dawn is that the time when the measured time in the time zone before sunrise from the dawn was flat was 3600 minutes. Therefore, it is not limited to the measured value at 3600 minutes as the time zone before the sunrise from the dawn, and the measured values at other times (for example, each measured value at 720 minutes and 2160 minutes) may be selected.

Similarly, plant detection camera 1 can appropriately correct and derive the measured value of each of true leaves PT10, PT11, and PT12, and the measured value of each of artificial leaves frc1 and frc2 based on the baseline correction as much as possible by suppressing the influence of external light. The measured values of true leaves PT10, PT11, PT12 and the artificial leaves frc1 and frc2 after the base line correction are represented by characteristics GH3a, GH2a, GH1a, ZH1a, and ZH2a as illustrated in FIG. 35. As a result, in the present embodiment, when the plant detection camera 1 estimates the predictive value of the relative water content rate of the true leaf (refer to FIGS. 39 and 40), the average water content index of the artificial leaf as the external standard sample is not changed with time, and thus, reliability as an external standard sample of the artificial leaf is improved.

Here, after the final measurement time illustrated in FIG. 34, for example, true leaf PT10 is picked (so-called defoliation) from the state illustrated in FIG. 30, and the water content is actually measured by the method illustrated in FIG. 9. That is, weight a (g) of true leaf PT10, which is the tip end leaf which has picked at the final measurement time (14:30 on Thursday, Apr. 28, 2016) is measured and true leaf PT10 is dried at 110° C. in an atmosphere for two hours. In a case of weight b (g) of true leaf PT10 after dry, the water content of true leaf PT10 is calculated from (a−b)/a.

In addition, the measured value (average water content index) of the tip end leaf (true leaf PT10) at the final measurement time is set as G, and the measured values (average water content index) of the artificial leaves (artificial leaves frc1 and frc2) are set as V and R. Threshold level setter/water content index detector 27a of plant detection camera 1 can acquire these measured values and obtain the relative water content $Y_V$ of artificial leaf frc1 as (V/G)×(a−b)/a, and similarly, obtain the relative water content $Y_R$ of the artificial leaf frc2 as can be obtained as (R/G)×(a−b)/a.

Accordingly, threshold level setter/water content index detector 27a of plant detection camera 1 can calculate and derive the relative water content rate of the tip end leaf as (X/V)×$Y_V$ or (X/V)×$Y_R$ when measured value (average water content index) of the tip end leaf (true leaf PT10) at a certain time during the measurement is set as X. Here, in the calculation of the relative water content, it is preferable to use the measured value and the relative water content rate of the artificial leaf which are close to the measured value (average water content index) of true leaf PT10. The reason for the temperature change (temperature properties) due to the reflection light of sunlight or sunlight is that the degree of influence on the background fluctuation is changed depending on the magnitude of the relative water content rate of the temperature change (temperature properties) due to sunlight reflection light or sunlight.

Figure 38:
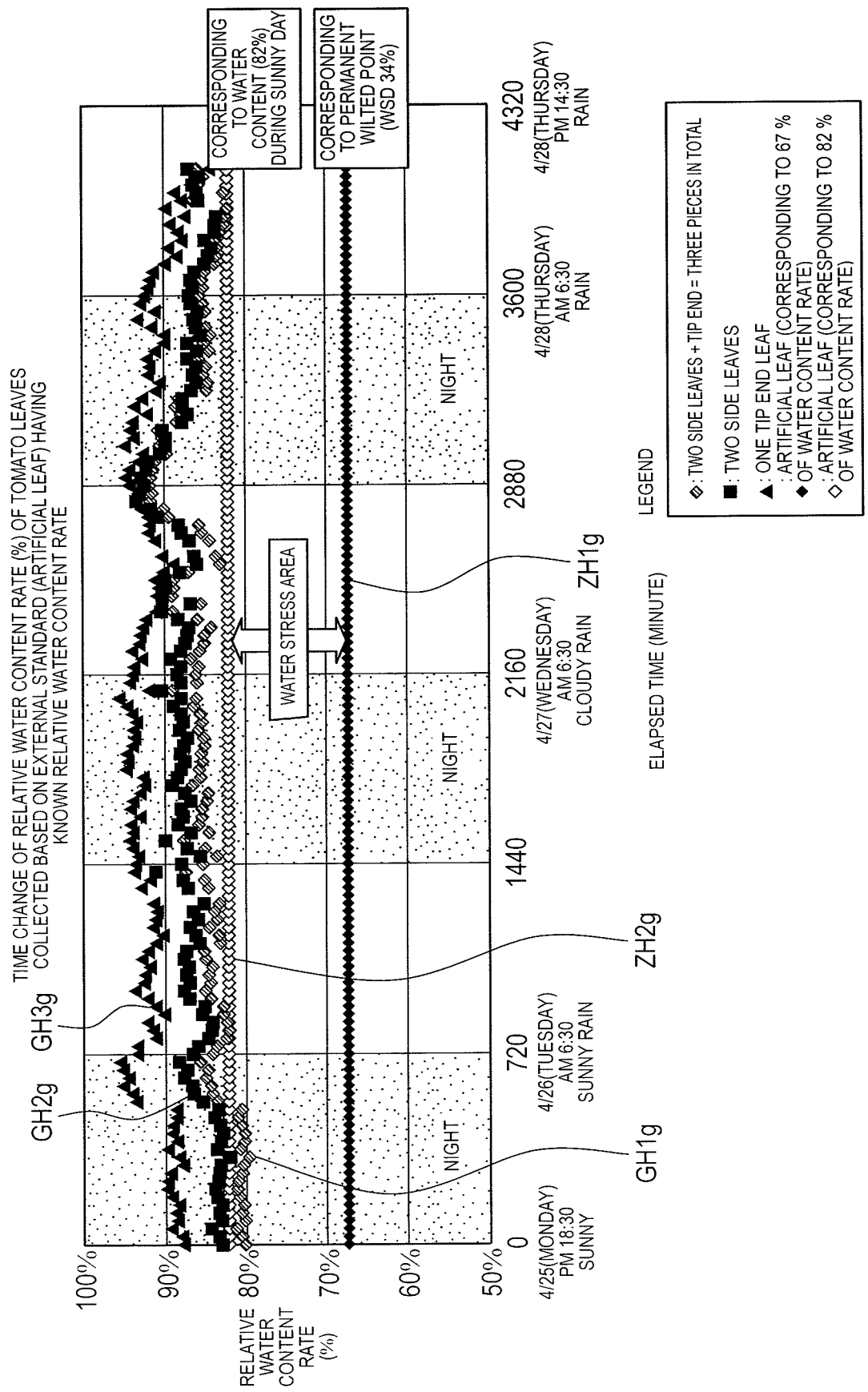
FIG. 38 is a graph illustrating an example of the time-transition in the relative water content rate of the true leaf calculated using the relative water content rate of the artificial leaf calculated based on the water content rate of the true leaf at the time of final measurement.

FIG. 38 is a graph illustrating an example of the time-transition in the relative water content of true leaf PT10 calculated using the relative water content rate of the artificial leaf calculated based on the water content rate of true leaf PT10 at the time of final measurement. In addition to characteristic GH3g of the time-transition of the relative water content of true leaf PT10, FIG. 38 also illustrates characteristics GH2g, GH1g, ZH2g, and ZH1g of the time-transition of the relative water contents of the side leaf (true leaves PT11 and PT12), the tip end leaf and the side leaf, and artificial leaves frc1 and frc2. The relative water content rate of artificial leaf frc1 corresponds to the water content (about 82%) of true leaf PT10 on sunny day. On the other hand, the relative water content rate of artificial leaf frc2 corresponds to the water content of permanent wilted point (in other words, WSD: Water Saturated Deficit is about 34%) of true leaf PT10. Accordingly, it is understood that if the relative water content of true leaf PT10 is between characteristics ZH1g and ZH2g, an appropriate water stress is applied to true leaf PT10.

As a result, for example, the relative water content rate of each of artificial leaves frc1 and frc2 illustrated in FIG. 30 is calculated and determined. The relative water content rate of each of artificial leaves frc1 and frc2 becomes a constant value without the time-transition. Here, the time-transition of the relative water content illustrated in FIG. 38 was obtained by calculating the water content at the time when true leaf PT10 is picked in the final measurement time, but is not obtained by calculating the relative water content of true leaf PT10 during the measurement (in other words, in real time).

Figure 39:
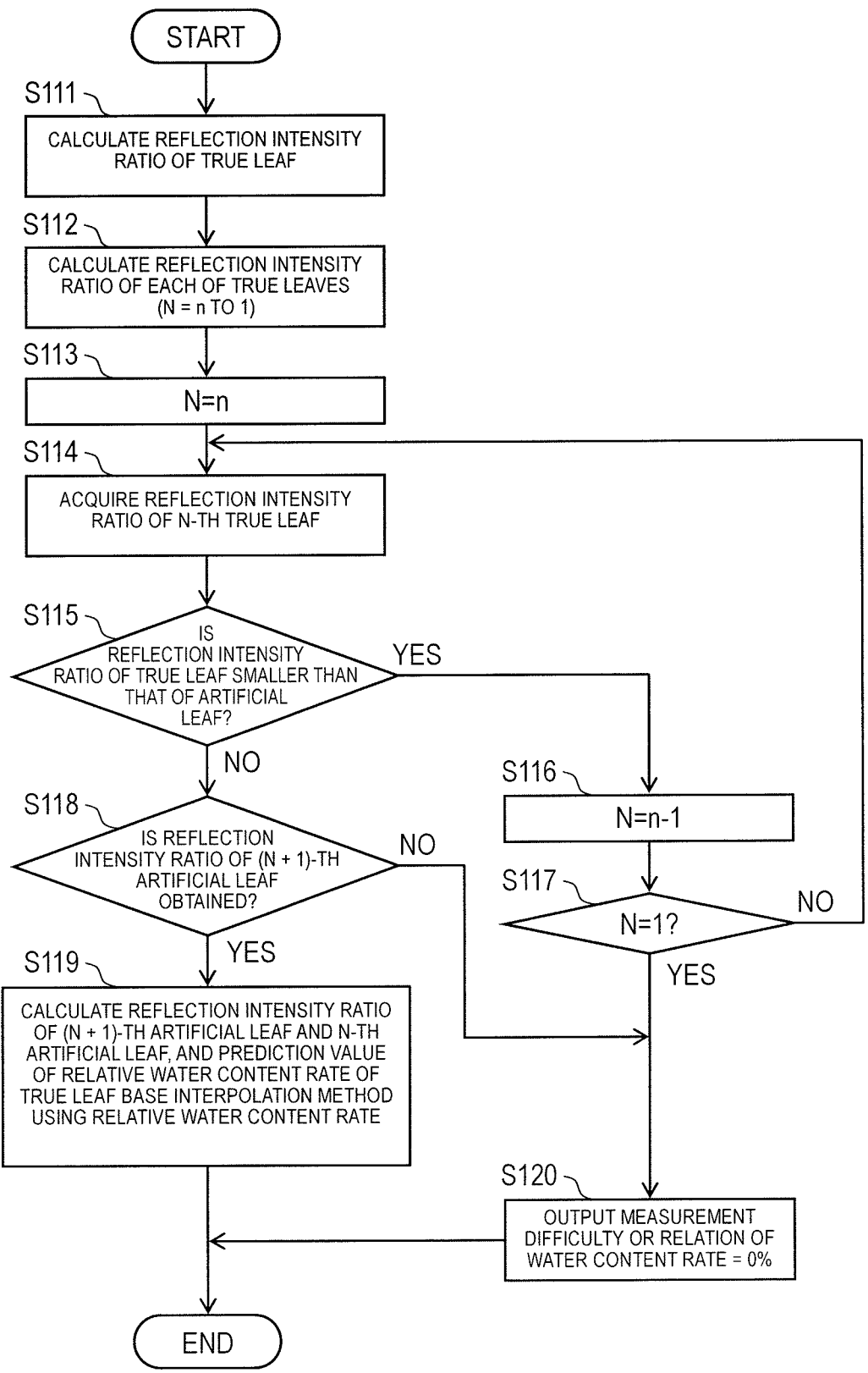
FIG. 39 is a flow chart illustrating an example of a procedure of calculating the relative water content rate of the true leaf during the measurement of the reflection intensity ratio of the true leaf of the third embodiment.
Figure 40:
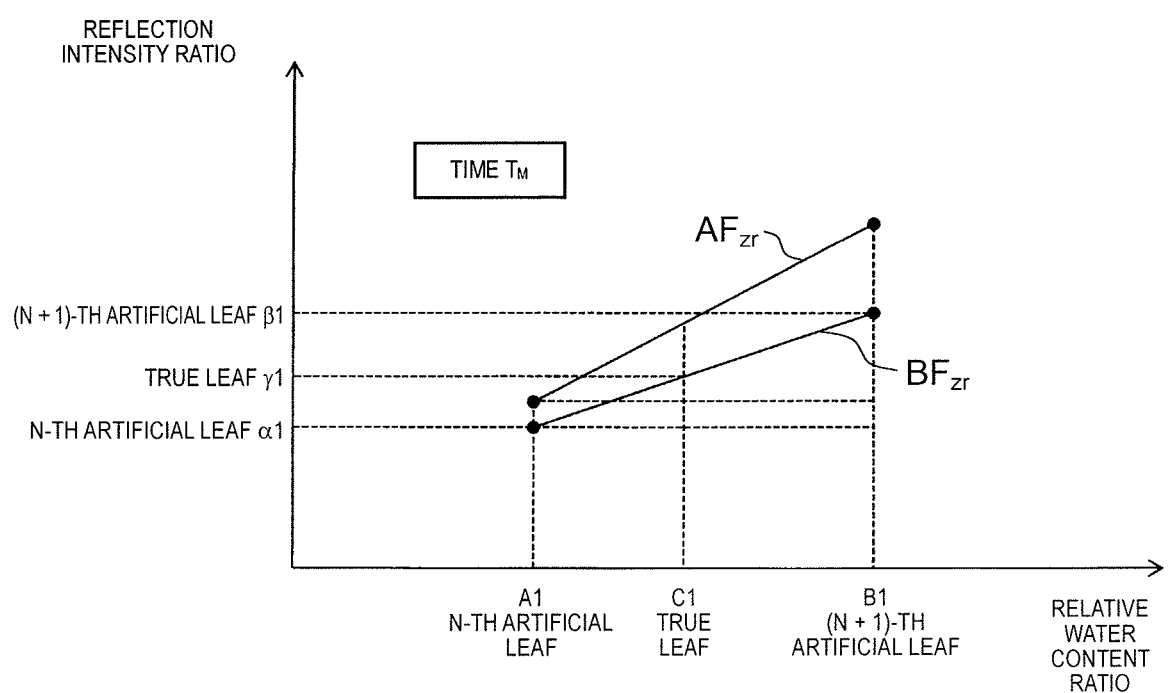
FIG. 40 is a diagram illustrating an interpolation method using the reflection intensity ratios of two kinds of artificial leaves used in step S119.

Next, by using the relative water content of each of artificial leaves frc1 and frc2 as illustrated in FIG. 38 (that is, the relative water content which was unclear at start of the experiment (measurement) illustrated as illustrated in FIG. 34, but was calculated based on the water content of the leaf PT10 at the final measurement time) as a known relative water content, a method of estimating the predictive value of the relative water content of true leaf PT10 during measurement will be described with reference to FIGS. 39 and 40.

FIG. 39 is a flow chart illustrating an example of a procedure of calculating the relative water content rate of the true leaf PT10 during the measurement of the reflection intensity ratio of true leaf PT10 of the third embodiment. FIG. 40 is a diagram illustrating an interpolation method using the reflection intensity ratios of two kinds of artificial leaves frc1 and frc2 used in step S119. FIG. 39 and FIG. 40 illustrate an example of calculating the relative water content of true leaf PT10 at certain time point $T_M$ during the measurement from the relative water content (known) and reflection intensity ratio (measured value) of the plurality of artificial leaves at the same time point TAI.

In FIG. 39, threshold level setter/water content index detector 27a calculates the reflection intensity ratio of true leaf PT10 at certain time point $T_M$ after measurement start (S111). The details of the calculation in step S111 are described with reference to FIG. 8, for example, and a description thereof will not be repeated. Further, threshold level setter/water content index detector 27a calculates the reflection intensity ratio of each of artificial leaves frc1 and frc2 at the same time point $T_M$ as that in step S111 (S112). Note that, the details of the calculation in step S112 are described with reference to FIG. 8, for example, and a description thereof will not be repeated.

In the explanation of FIG. 39, it is assumed that n (n: natural number of 2 or more) artificial leaves are used and N is any one of 1 to n and is an ordinal number indicating one of the artificial leaves. In addition, as N is increased from 1 to n, the value of the reflection intensity ratio of the artificial leaf becomes larger. That is, it is assumed that the reflection intensity ratio of (N=1) artificial leaf at a certain time point is the smallest, and the reflection intensity ratio of (N=n) artificial leaf at the same time point is the largest.

Threshold level setter/water content index detector 27a sets N=n (S113). That is, threshold level setter/water content index detector 27a acquires the reflection intensity ratio (that is, maximum reflection intensity ratio at certain time point $T_M$) of (N=N)-th artificial leaf at certain time point $T_M$ (S114). Threshold level setter/water content index detector 27a determines whether or not the reflection intensity ratio of (N=n)-th artificial leaf at certain time point $T_M$ is larger than the reflection intensity ratio of true leaf PT10 (S115). Threshold level setter/water content index detector 27a sets N=(n−1) by decreasing one N in a case where the reflection intensity ratio of (N=N)-th artificial leaf at certain time point $T_M$ is determined to be larger than the reflection intensity ratio of true leaf PT10 (YES in S115) (S116).

Threshold level setter/water content index detector 27a determines whether or not N=1 is established at certain time $T_M$ (S117). In a case were N=1 is not established (NO in S117), the process of threshold level setter/water content index detector 27a returns to step S114.

On the other hand, threshold level setter/water content index detector 27a determines whether or not the reflection intensity ratio of (N+1)-th artificial leaf is larger than the reflection intensity ratio of current N-th artificial leaf in a case where the reflection intensity ratio of (N=N)-th artificial leaf at certain time point $T_M$ is determined to be smaller than the reflection intensity ratio of true leaf PT10 (NO in S115) (S118).

Threshold level setter/water content index detector 27a calculates the predictive value of the relative water content rate of the true leaf at certain time point $T_M$ through an interpolation method (refer to FIG. 40) using the reflection intensity ratio of (N+1)-th and N-th artificial leaf, and the relative water content in a case where the reflection intensity ratio of (N+1)-th artificial leaf is larger than the reflection intensity ratio of current N-th artificial leaf (YES in S118) (S119). Note that, every time the predictive value of the relative water content rate of the true leaf at certain time point $T_M$, which is obtained in step S119 is calculated, threshold level setter/water content index detector 27a may appropriately display the process on a measurement result display screen (for example, refer to FIG. 16) of the experiment displayed on monitor 50, as the process of step S45 in FIG. 15. Thus, the user can rapidly ascertain the predictive value of the relative water content rate of the true leaf, and can determine whether or not the water stress is appropriately applied. After step S119, the process of threshold level setter/water content index detector 27a as illustrated in FIG. 39 is completed.

On the other hand, in a case where N=1 in step S117 (YES in S117), or the reflection intensity ratio of (N+1)-th artificial leaf which is larger than the reflection intensity ratio of current N-th artificial leaf is not obtained in step S118 (NO in S118), threshold level setter/water content index detector 27a performs the process of step S120. That is, threshold level setter/water content index detector 27a instructs display processor 29 to display a message indicating that it is not easy to measure the relative water content of true leaf PT10 at certain time point $T_M$ or a message indicating that the relative water content is 0% on monitor 50 (refer to FIG. 1) via detection result filter 27c. According to the instruction from detection result filter 27c, display processor 29 displays a message indicating that it is not easy to measure the relative water content of true leaf PT10 at certain time point $T_M$ or a message indicating that the relative water content is 0% on monitor 50 (refer to FIG. 1).

Here, the interpolation method in step S119 will be described with reference to FIG. 40. The horizontal axis in FIG. 40 indicates a relative water content, and the vertical axis in FIG. 40 indicates a reflection intensity ratio.

In FIG. 40, in a process time point (that is, certain time point $T_M$) of step S119, the reflection intensity ratio and the relative water content of each of (N+1)-th and N-th artificial leaves may be obtained. In other words, all of reflection intensity ratio γ1 of true leaf PT10, reflection intensity ratio α1 of N-th artificial leaf, reflection intensity ratio β1 in of the (N+1)-th artificial leaf, relative water content (known) A1 of the N-th artificial leaf, and reflection intensity ratio B1 of the (N+1)-th artificial leaf are known. As presented in line BFzr illustrated in FIG. 40, the relative water content and the reflection intensity ratio have a linear correlation. Accordingly, threshold level setter/water content index detector 27a may calculate a predictive value of relative water content C1 in true leaf PT10 at certain time point $T_M$ after the start of the measurement, as $\{\{(B1-A1)/(\beta1-\alpha1)\}\times(\gamma1-\alpha1)\}+A1\}$. This predictive value is derived by using the obtained relative water content (almost constant) of each artificial leaf described with reference to FIG. 38. Therefore, it is considered that the reliability of the relative water content C as the predictive value is high. Even during the measurement, the plant detection camera 1 according to the present embodiment can calculate a relative water content of the true leaf with high accuracy by using a reflection intensity ratio of the true leaf and reflection intensity ratios and relative water contents of the plurality of artificial leaves.

According to the present embodiment, even in a case where white reference substrate bd is moved during the measurement such that the position is deviated from the position at the time of the starting of the measurement, plant detection camera 1 can appropriately derive the relative water contents of true leaves PT10, PT11, and PT12. Line BFzr illustrated in FIG. 40 indicates the correlation between the relative water content before the position of white reference substrate bd is deviated and the reflection intensity ratio. Line AFzr illustrated in FIG. 40 indicates the correlation between the relative water content after the position of white reference substrate bd is deviated and the reflection intensity ratio.

That is, even in a case where the position of white reference substrate bd is deviated during the measurement, all of true leaves PT10, PT11, and PT12, and the plurality of artificial leaves frc1 and frc2 are attached to white reference substrate bd, and thus it is considered that the positions thereof are deviated in the same direction. Therefore, even in a case where the correlation indicated by line AFzr is changed to the correlation indicated by line BFzr, the correlation between the relative water content and the reflection intensity ratio does not change. Accordingly, even if the slope of the line indicating the relationship between the relative water content and the reflection intensity ratio is changed due to the positional deviation of white reference substrate bd, the interpolation method of step S119 can be used in the same manner, as described above, plant detection camera 1 of the present embodiment can calculate the value of the relative water content of true leaves PT10, PT11, and PT12 as an estimated value with high accuracy. Therefore, in a case where plant detection camera 1 is not limited to a stationary type in which plant detection camera 1 is installed in a fixed position, for example, plant detection camera 1 can be configured as a handy type which the user can hold by hand, handy type plant detection camera 1 can calculate the values of the relative moisture contents of true leaves PT10, PT11, and PT12 as estimated values with high accuracy. Handy type plant detection camera 1 is grabbed by the hand of the user and the positional deviation occurs due to some shaking or movement, but plant detection camera 1 of the present embodiment can calculate the values of the relative water contents of true leaves PT10, PT11, and PT12 as estimated values with high accuracy, even if the position of white reference substrate bd is deviated. According to handy type plant detection camera 1, the user can obtain the relative water contents of the true leaves as the observation targets in a plurality of portions, compared with stationary type plant detection camera 1, and thus (many) data at spatially multiple points can be acquired.

As illustrated in FIG. 30, artificial leaves frc1, frc2, and frc3 of the present embodiment is attached to white reference substrate bd to be disposed near true leaves PT10, PT11, and PT12 as the observation targets. Here, the method of attaching white reference substrate bd of artificial leaves frc1, frc2, and frc3 is not limited to the example of FIG. 30 (for example, see FIGS. 41A and 41B, 42A, and 42B).

FIGS. 41A and 41B are diagrams illustrating first modification examples of attachment with respect to white reference substrate bd of true leaves PT10, PT11, and PT12 and artificial leaf frc1. FIGS. 42A and 42B are diagrams illustrating second modification examples of attachment with respect to white reference substrate bd of true leaves PT10, PT11, and PT12 and artificial leaf frc1.

As illustrated in FIG. 41B, for example, as in the case of FIG. 25, for example, artificial leaf frc1 mixed with fructose having a predetermined content ratio may be attached around the white reference substrate bd like a picture frame. FIG. 41A is a side sectional view of FIG. 41B. In FIG. 41A, it is illustrated that the thicknesses of white reference substrate bd and artificial leaf frc1 are substantially the same, but in practice, the thickness of white reference substrate bd is about 3 mm, and the thickness of artificial leaf frc1 is about 100 to 400 Even in the attachment example in FIG. 30, the thicknesses of white reference substrate bd and artificial leaf frc1 are the same. In addition, in FIG. 41B, four kinds of artificial leaves created to have different contents of fructose included in the artificial leaves are attached for each side of the four sides of white reference substrate bd.

In addition, as illustrated in FIG. 42B, true leaves PT10, PT11, and PT12 are attached on the right side of the paper of FIG. 42B, with respect to white reference substrate bd, further the optical axis direction of plant detection camera 1 and the normal direction of white reference substrate bd coincide with each other, and artificial leaf frc1 having two square-shaped cross sections along the direction and having a constant thickness and artificial leaf frc2 having two regular triangular cross sections along the same direction and having the same thickness may be attached.

That is, in FIG. 42B, artificial leaves frc1 and frc2 are attached to white reference substrate bd so as to have a test pattern shape which is generally known for checking the degree of parallelism. Accordingly, for example, in a case where the position of white reference substrate bd is deviated in the pan direction, the tilt direction, or both directions during measurement, the square and the equilateral triangle deviate in the same way in the shifted direction, and thus plant detection camera 1 can calculate the value of the deviated angle. For example, in a case where the position is deviated in the pan direction (lateral direction), the length in the horizontal direction changes, and the size is not a square or an equilateral triangle. In the same manner, the position is deviated in the tilt direction (vertical direction), the length in the vertical direction changes and the size is not a square or an equilateral triangle. In addition, plant detection camera 1 can detect whether the normal direction of the white reference substrate bd and the optical axis of plant detection camera 1 are parallel or deviated at the time of initial setting before the start of measurement and thus the work at the time of initial installation of white reference substrate bd can be caused to be effective. In addition, since true leaves PT10, PT11, and PT12 the plurality of artificial leaves frc1 and frc2 are attached to white reference substrate bd, while plant detection camera 1 checks the parallelism between the normal direction of white reference substrate bd and the optical axis of plant detection camera 1, for example, plant detection camera 1 can calculate the relative water content of true leaf PT10 (for example, see step S119 of FIG. 39).

As described above, plant detection camera 1 according to the third embodiment is disposed to face white reference substrate bd that covers the rear surfaces of tomato leaves (true leaves PT10, PT11, and PT 12) as observing portions of the plant and artificial leaves frc1 and frc2 as at least one external sample having the same chemical properties as water contained in true leaves PT10, PT11, and PT12. Plant detection camera 1 radiates reference beam LS1 which is a near infrared laser beam having a characteristic in which light tends not to be absorbed in water while sequentially scanning toward white reference substrate bd. Plant detection camera 1 radiates measuring beam LS2 which is a near infrared laser beam having a characteristic in which light tends to be absorbed in water while sequentially scanning toward white reference substrate bd. Plant detection camera 1 derives the water content (for example, relative water content) (see step S119 of FIG. 39) contained in true leaves PT10, PT11, and PT12 based on each reflection light of reference beam LS1 reflected on true leaves PT10, PT11, and PT12 and artificial leaves frc1 and frc2 and each reflection light of measuring beam LS2 reflected on true leaves PT10, PT11, and PT12 and artificial leaves frc1 and frc2 in a certain measurement period. In addition, plant detection camera 1 displays the time-transition of the water content (for example, relative water content) contained in true leaves PT10, PT11, and PT12 in the measurement period on monitor 50.

With this, Plant detection camera 1 has the same chemical properties as water (for example, absorption spectrum), and uses artificial leaves frc1 and frc2 which have a known relative water content, and thereby estimating the water content (for example, relative water content) contained in the leaves (true leaves PT10, PT11, and PT12) of the tomato with high accuracy. In addition, plant detection camera 1 can quantitatively and visually suggest the time-transition of the water content contained in the leaves (true leaves PT10, PT11, and PT12) of the tomato to the user, and can contribute to the early teaching of the timing of irrigation to the plant.

In addition, at least one of artificial leaves frc1 and frc2 is a sample obtained by mixing fructose (fruit sugar) having an absorption spectrum equivalent to the absorption spectrum of water with respect to each wavelength (905 nm and 1,550 nm) of reference beam LS1 and measuring beam LS2 as chemical properties with the epoxy resin. As an example of chemical properties, fructose (that is, fruit sugar) has near infrared spectra (absorption spectrum) similar to that of water ($H_2O$), as illustrated in FIG. 32. This because the chemical structural formula of fructose is well known, for example, as illustrated in FIG. 32, the molar light absorption coefficient is large since a proportion of a hydroxyl group (that is, an OH group which is a hydroxyl group) that configures water contained in the true leaf is high, and the reliability of the measurement value of the fructose content is high since the vapor pressure is lower than that of water and the fructose content does not change due to evaporation or the like at ordinary temperature and normal pressure. Furthermore, the use of epoxy resin as an example of the main components of artificial leaves frc1 and frc2 is due to the following reasons.

Unlike fructose, an epoxy resin has a small absorption of near infrared rays based on an OH group which is a hydroxyl group in a chemical structural formula, has no water solubility, is strong against ultraviolet rays, and hardly peels off, and the composition thereof does not change with time, and thus the stability is high. Therefore, with respect to artificial leaves frc1 and frc2 of the present embodiment, according to the solidification of the fructose having water solubility and the epoxy resin having little water solubility by the amine curing agent, for example, it is possible to obtain artificial leaves of which shapes and chemical properties hardly change with time, even during experimental measurement.

In addition, true leaves PT10, PT11, and PT12 and the plurality of artificial leaves frc1 and frc2 are disposed near white reference substrate bd. Accordingly, true leaves PT10, PT11, and PT12 and the plurality of artificial leaves frc1 and frc2 are easily influenced by the same influence of external light (for example, sunlight). Accordingly, in a case where the relative water contents of artificial leaves frc1 and frc2 are not clear (see FIG. 34), according to the baseline correction of the average water content index based on the reflection intensity ratio of artificial leaves frc1 and frc2, the reflection intensity ratios of true leaves PT10, PT11, and PT12 are also appropriately corrected. Therefore, the calculated accuracy of the relative water content is increased, and thus the calculated accuracy of the unclear relative water contents of artificial leaves frc1 and frc2 are increased.

In addition, according to the instruction from plant detection camera 1, monitor 50 displays a range (for example, target range Bw illustrated in FIG. 12) of the target water content indicating a state in which desired water stress is applied to true leaves PT10, PT11, and PT12. If controller 11 of plant detection camera 1 detects that the water content included in true leaves PT10, PT11, and PT12 becomes the value near the lower limit of target range Bw, controller 11 may instruct monitor 50 so as to display the display an indication for urging the irrigation to true leaves PT10, PT11, and PT12. Accordingly, the user may promptly and simply know that the water stress applied to true leaves PT10, PT11, and PT12 as the observation target of plant detection camera 1 becomes excessive, and the timing for irrigating is close.

In addition, monitor 50 displays the range of water content (for example, target range Bw illustrated in FIG. 12) of the target indicating the state in which the desired water stress is applied to true leaves PT10, PT11, and PT12 according to the instruction from plant detection camera 1. If controller 11 of plant detection camera 1 detects that the water contents of true leaves PT10, PT11, and PT12 becomes the value near the upper limit value of target range Bw, controller 11 may instruct monitor 50 to display an indication for urging the stopping of the irrigation to true leaves PT10, PT11, and PT12. Accordingly, the user may promptly and simply know that it is required to reduce (in other words, apply the water stress) the water content (for example, average water content index) contained in true leaves PT10, PT11, and PT12 by stopping the irrigation to true leaves PT10, PT11, and PT12 of the observation target of plant detection camera 1.

In addition, the cultivation device of the present embodiment has a configuration of including plant detection camera 1 and fertilizer or water supply device WF as a cultivation controller. Fertilizer or water supply device WF can irrigate a predetermined amount of moisture to true leaves PT10, PT11, and PT12 based on the time-transition of water content (for example, average water content index or relative water content) calculated by plant detection camera 1, for example, according to the instruction from plant detection camera 1 based on the operation of the user, in a partial period of the measurement period.

Subsequently, with respect to the increase of the intensity of reflection light as a constant background based on the reception of external light (for example, sunlight) during the measurement and the change of the intensity of reflection light as a constant background due to the change of the temperature of true leaves and artificial leaves based on the reception of sunlight, examples of considering a method of irradiation with a near-infrared laser beam for suppressing the influence of external light as much as possible are described with reference to FIGS. 43A, 43B, 43C, 44A, 44B, 44C, and 45.

FIG. 43A is a graph illustrating an example of the intensity of the reflection light with respect to each wavelength of the near infrared laser beam when irradiated with the near infrared laser beam of 905 nm and 1550 nm toward the true leaf PT10 outdoors. FIG. 43B is a graph illustrating an example of the intensity of the reflection light with respect to each wavelength of the near infrared laser beam when irradiated with the near infrared laser beam of 905 nm and 1550 nm toward the true leaf PT10 outdoors. FIG. 43C is a graph illustrating an example of the intensity of the reflection light for each of near infrared laser beam of 905 nm and 1550 nm which is originally necessary for accurately calculating the water content of the true leaf PT10.

Figure 45:
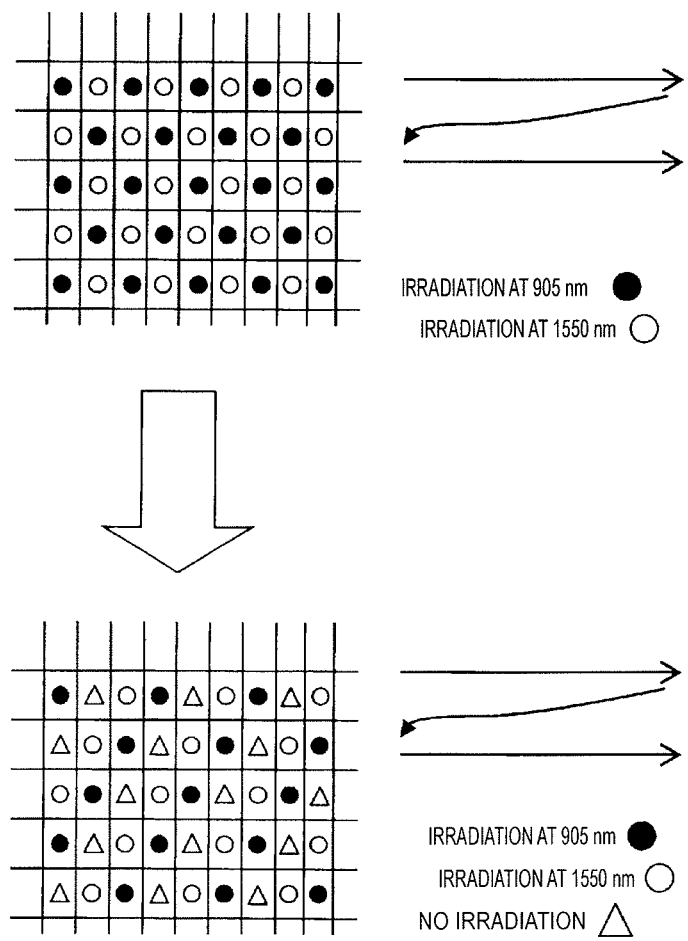
FIG. 45 is a diagram illustrating an example of irradiation timing of the near infrared laser beams at 905 nm and 1550 nm, which is useful for measuring the intensity of the reflection light based on the influence of sunlight.

FIG. 44A is a graph illustrating an example of a change of a rise of the background of the intensity of the reflection light based on the influence of sunlight at time T1 when the white reference substrate is installed outdoor. FIG. 44B is a graph illustrating an example of a change of a rise of background of the intensity of the reflection light based on the influence of sunlight at time T2 when the white reference substrate is installed outdoor. FIG. 44C is a graph illustrating an example of a change of a rise of the background of the intensity of the reflection light based on the influence of sunlight at time T3 when the white reference substrate is installed outdoor. FIG. 45 is a diagram illustrating an example of irradiation timing of the near infrared laser beams at 905 nm and 1550 nm, which is useful for measuring the intensity of the reflection light based on the influence of sunlight.

In FIGS. 43A, 43B, and 43C, the horizontal axis indicates the wavelength, and the vertical axis indicates the intensity (light intensity) of the reflection light. In FIGS. 44A, 44B, and 44C, the horizontal axis indicates the wavelength, and the vertical axis indicates the intensity (light intensity) of the reflection light. In addition, FIG. 43A corresponds to FIG. 10A, and FIG. 43B corresponds to FIG. 10B, and thus the description of the same content is simplified or omitted, and different content is described.

In FIGS. 43A and 43B, range PDs indicate the wavelength range of the photo diode (PD) having sensitivity in the wavelength range of the near infrared laser beam (that is, reference beam LS1 and measuring beam LS2) in a certain range. In FIG. 43A, the leaf (for example, true leaf PT10) as the observation target is installed outside, and also white reference substrate bd is not attached. Therefore, the multiple scattering of sunlight occurs in surrounding leaves (for example, true leaves PT11 and PT12) occurs, and the received portion of the reflection light from the surrounding leaves (for example, true leaves PT11 and PT12) reflected due to the multiple scattering is added as background. Accordingly, since the wavelength (905 nm) of reference beam LS1 has high transmittance, the intensity of the reflection light of reference beam LS1 relatively increases according to the increase of the background. Meanwhile, the wavelength (1550 nm) of measuring beam LS2 has low transmittance, and thus the intensity of the reflection light of measuring beam LS2 relatively decreases according to the increase of background. Meanwhile, the wavelength (1550 nm) of measuring beam LS2 has low transmittance, and thus the intensity of the reflection light of measuring beam LS2 relatively decreases according to the increase of background.

Subsequently, in FIG. 43B, true leaf PT10 is installed outdoor, but white reference substrate bd is attached to the rear surface side of true leaf PT10. Therefore, multiple scattering of the sunlight on the surrounding leaves (for example, true leaves PT11 and PT12) does not occur, and thus the increase of the background as illustrated in FIG. 43A does not occur. Therefore, the intensity of the reflection light of reference beam LS1 increases by the intensity based on the received light portion of the sunlight, but the same is applied to the intensity of the reflection light of measuring beam LS2. Accordingly, compared with a case illustrated in FIG. 43A, the intensity of each reflection light of reference beam LS1 and measuring beam LS2 reflected on true leaf PT10 becomes a value close to the originally necessary intensity, but the light receives an influence of sunlight, and thus an error of about several % is included in the calculated value of the correct reflection intensity ratio (in other words, average water content index) of true leaf PT10.

In FIG. 43C, intensity of each reflection light of reference beam LS1 and measuring beam LS2 from which the change of the light intensity based on the reception of the sunlight illustrated in FIG. 43B and the light intensity change based on the temperature change due to the sunlight are subtracted are illustrated. Originally, in order to obtain water concentration C in accordance with the above-mentioned Expression (3), the reflection intensity ratio $I_{905}/I_{1550}$ based on the reflection light of the appropriate reflection beam LS1 and measuring beam LS2 is to be substituted into Expression (3). However, as described with reference to FIG. 43B, even though white reference substrate bd is attached, the light intensity and the temperature change based on the reception of the sunlight are multiplied. Also, since the intensity of this sunlight changes from time to time, the intensity of the sunlight and the corresponding temperature change are required to be subtracted in accordance with the time.

FIG. 44A illustrates the intensity of the reflection light of each of reference beam LS1 and measuring beam LS2 at time T1 (for example, daytime time of sunny day). The intensity of the sunlight in the entire range PDs at time T1 is larger. In other words, since the amount of the received sunlight is large, plant detection camera 1 is to obtain reflection intensity ratio $I_{905}/I_{1550}$ to be substituted into the above-described Expression (3) by subtracting the temperature change in the reflection light based on the intensity of the reflection light of the received sunlight as illustrated in FIG. 44A and the sunlight from the actual value of the intensity of the reflection light of each of reference beam LS1 and measuring beam LS2.

FIG. 44B illustrates the intensity of the reflection light of each of reference beam LS1 and measuring beam LS2 at time T2 (for example, the evening of sunny day). The intensity of sunlight is decreasing at the higher wavelength side of range PDs at time T2. Therefore, plant detection camera 1 is to obtain reflection intensity ratio $I_{905}/I_{1550}$ to be substituted into the above-described Expression (3) by subtracting the temperature change in the reflection light based on the intensity of the reflection light of the received sunlight as illustrated in FIG. 44B and the sunlight from the actual value of the intensity of the reflection light of each of reference beam LS1 and measuring beam LS2. Note that, in FIG. 44B, the irradiation timing of reference beam LS1 and measuring beam LS2 is an order of microseconds, the wavelength distribution of each reflection light based on the reception of detected sunlight and temperature properties may be considered to be the same.

FIG. 44C illustrates the intensity of the reflection light of each of reference beam LS1 and measuring beam LS2 at time T3 (for example, cloudy day). The intensity of the sunlight in the entire range PDs at time T1 is deteriorated. Plant detection camera 1 is to obtain reflection intensity ratio $I_{905}/I_{1550}$ to be substituted into the above-described Expression (3) by subtracting the intensity change in the reflection light based on the temperature change by the intensity of the reflection light of the reception of sunlight as illustrated in FIG. 44C and the sunlight from the actual value of the intensity of the reflection light of each of reference beam LS1 and measuring beam LS2. Note that, a photodiode (PD) which is a light receiving element digitizes the wavelength distribution of the sunlight (that is, the reflection light) that changes over time by converting and integrating the wavelength distribution into a current value based on the sensitivity of each wavelength. This numerical value corresponds to the intensity of each reflection light based on the reception of sunlight to be subtracted as described above and the change in the intensity of the reflection light based on the temperature change due to the sunlight.

In addition, in order to obtain the intensity of the reflection light based on the reception of sunlight as described above, as illustrated in the lower side of FIG. 45, it is preferable to provide a period, during which reference beam LS1 and measuring beam LS2 are not radiated, between the irradiation timings of reference beam LS1 at 905 nm and measuring beam LS2 at 1550 nm. For example, in the irradiation method as illustrated in the upper side of FIG. 45, when reference beam LS1 is radiated within irradiation cycle F, the reflection light of reference beam LS1, which is affected by the sunlight is received by plant detection camera 1. When measuring beam LS2 is radiated within subsequent irradiation cycle, the reflection light of measuring beam LS2, which is affected by the sunlight is received by plant detection camera 1. Therefore, since the interval at which only the sunlight is received by plant detection camera 1 is not obtained, the intensity of each reflection light based on the reception of sunlight to be subtracted as described above is not obtained.

In this regard, as illustrated in the lower side of FIG. 45, when the period during which reference beam LS1 and measuring beam LS2 are not radiated, the reflection light of reference beam LS1 within the irradiation cycle and the reflection light of measuring beam LS2 are not received, and thus only the sunlight is received by the plant detection camera 1. In other words, plant detection camera 1 can obtain the intensity of each reflection light based on the reception of sunlight to be subtracted as described above by the intensity of the reflected sunlight received within this irradiation period.

As described above, in consideration of the above-description with reference to FIGS. 43A, 43B, and 43C, FIGS. 44A, 44B, and 44C and FIG. 45, controller 11 of plant detection camera 1 controls the irradiation timings of reference beam LS1 and measuring beam LS2 such that a non-irradiation period is provided between the irradiation cycle of reference beam LS1 and the irradiation cycle of measuring beam LS2. Plant detection camera 1 subtracts the same wavelength component as reference beam LS1 of the sunlight received within the non-irradiation period from the reflection light of each reference beam LS1 reflected on true leaf PT10 and at least one artificial leaves frc1 and frc2. Further, plant detection camera 1 subtracts the same wavelength component as measuring beam LS2 of the sunlight received within the non-irradiation period from the reflection light of each measuring beam LS2 reflected on true leaf PT10 and artificial leaves frc1 and frc2. With this, plant detection camera 1 can accurately calculate the reflection intensity ratio to be originally substituted into Expression (3), and thus accurately derive the water content contained in true leaf PT10, which is suppressed as much as possible from the influence of the sunlight.

In addition, plant detection camera 1 may also be disposed facing white reference substrate bd covering the back surface of the leaves (PT10, PT11, and PT12) of the tomato as the observing portions of the plant. In other words, only true leaves PT10, PT11, and PT12 may be attached on white reference substrate bd as illustrated in FIG. 30. Plant detection camera 1 radiates reference beam LS1 which is a near infrared laser beam having a characteristic in which light tends not to be absorbed in water while sequentially scanning toward white reference substrate bd. Plant detection camera 1 radiates measuring beam LS2 which is a near infrared laser beam having a characteristic in which light tends to be absorbed in water while sequentially scanning toward white reference substrate bd. Plant detection camera 1 derives the water content (for example, relative water content) contained in true leaves PT10, PT11, and PT12 based on each reflection light of reference beam LS1 reflected on true leaves PT10, PT11, and PT12, and each reflection light of measuring beam LS2 reflected on true leaves PT10, PT11, and PT12 in a certain measurement period. In addition, plant detection camera 1 displays the time-transition of the water content (for example, relative water content) contained in true leaves PT10, PT11, and PT12 in the measurement period on monitor 50. In deriving of this water content, it is preferable to provide the non-irradiation period during which reference beam LS1 and measuring beam LS2 are not radiated in order to suppress the influence of the sunlight as much as possible. Plant detection camera 1 subtracts the same wavelength component as reference beam LS1 of the sunlight received within the non-irradiation period from the reflection light of each reference beam LS1 reflected on true leaf PT10, PT11, and PT12. Further, plant detection camera 1 subtracts the same wavelength component as measuring beam LS LS2 of the sunlight received within the non-irradiation period from the reflection light of each measuring beam LS2 reflected on true leaf PT10, PT11, and PT12. Plant detection camera 1 derives the water content contained in true leaves PT10, PT11, and PT12 based on each reflection light after subtraction.

As a result, even in a case where artificial leaves frc1 and frc2 are used as at least one external standard sample, plant detection camera 1 can accurately calculate the reflection intensity ratio to be originally substituted into Expression (3), and thus accurately derive the water content contained in true leaves PT10, PT10, PT11, and PT12, which is suppressed as much as possible from the influence of the sunlight.

Although various embodiments are described above while referring to the drawings, needless to say, the present disclosure is not limited to Examples. It is obvious that it is possible for those skilled in the art to conceive of various Modification Examples and Correction Examples within the scope which is set forth in the claims, and therein is naturally understood as belonging to the technical scope of the present disclosure.

Meanwhile, in the description of the cultivation device of the present embodiment described above, the process of non-irrigation such as interrupting irrigation to the plant was performed in order to apply stress (for example, water stress) to the plant (for example, leaf of tomato). However, in the cultivation device of the present embodiment, the method of applying the stress (for example, water stress) to the plant is not limited to the non-irrigation. For example, in order to apply the stress (for example, water stress) to the plant, for example, the cultivation device of the present embodiment may change the electric conductivity of the liquid fertilizer (that is, liquid fertilizer) which is supplied to the plant to be equal to or larger than a predetermined value without using the non-irrigation. In other words, the cultivation device consequently applies water stress equivalent to the non-irrigation to the plant by changing the electric conductivity of the liquid fertilizer so that the electric conductivity of the liquid fertilizer is equal to or larger than a predetermined value. The reason for this is that when the electric conductivity of the liquid fertilizer is changed so as to be equal to or larger than a predetermined value, the root cannot absorb water due to an osmotic pressure relationship (in other words, salt stress is applied), and as a result, the water stress is applied to the plant similar to the case of non-irrigation. Note that, the aforementioned predetermined value is a known value obtained from the experience of the user and is the lower limit value of the electric conductivity of the liquid fertilizer when the salt stress is applied to the plant.

INDUSTRIAL APPLICABILITY

The present disclosure is useful as a device for observing water content, a method for observing water content, and a cultivation device which are capable of estimating water content contained in the plant by using an external standard sample has the same chemical properties as water, quantitatively and visually suggesting a time-transition of the water content to a user, and early teaching the timing of irrigation to the plant with high accuracy.

REFERENCE MARKS IN THE DRAWINGS

1 PLANT DETECTION CAMERA
11 CONTROLLER
11a TIMING CONTROLLER
13 FIRST BEAM SOURCE
15 SECOND BEAM SOURCE
17 BEAM SCANNER
21, 31 IMAGING OPTICS
23, 33 PHOTO DETECTOR
25 SIGNAL PROCESSOR
25a I/V CONVERTER
25b AMPLIFIER
25c COMPARATOR/PEAK HOLD
27a THRESHOLD LEVEL SETTER/WATER CONTENT INDEX DETECTOR
27b MEMORY
27c DETECTION RESULT FILTER
29 DISPLAY PROCESSOR
35 IMAGE SIGNAL PROCESSOR
37 DISPLAY CONTROLLER
50 MONITOR
60 UI (USER INTERFACE) SCREEN
61 SEARCH IRRIGATION AMOUNT INPUT SCREEN
63 SET AREA
64 INITIAL SETTING BUTTON
66 DEVIATION THRESHOLD LEVEL SETTING BUTTON
67, 68 INPUT BOX

71 IRRIGATION AMOUNT SEARCHING MODE BUTTON 71
72, 74 DISPLAY BOX
73 WATER STRESS CONTROL (CULTIVATION CONTROL) MODE BUTTON
101 BASE
102 BAR
151 TRIPOD
ARE AREA
BB BASE
bd, bdd WHITE REFERENCE SUBSTRATE
bd1 APERTURE
bd2 HOLE
bd3, bd4, bd5, bd21 SLIT
bd11 FRAME
Bw TARGET RANGE
gh1, gh2 GRAPH
Gm1 SCREEN FOR MONITORING WATER CONTENT IN LEAF
JG DETERMINER
PT3, PT3$t$, PT3$o$ LEAF
LS1 REFERENCE BEAM
LS2 MEASURING BEAM
mk1, mk2, mk3, mk4 MARK
mp CONNECTING MEMBER
MT COMMUNICATION TERMINAL
NVSS INVISIBLE LIGHT SENSOR
pf1, pf2, pf3, pf4 WATER STRESS PROFILE
PJ BEAM OUTPUT
TR TIMING SIGNAL FOR BEAM SCANNING
RF BEAM OUTPUT SIGNAL
RV0 AMBIENT LIGHT
RV1, RV2 DIFFUSE REFLECTION LIGHT
r1 to r11, r6 to r18, ra, rb, re ARROW
sc1, sc2, sc3 AREA
sm1, sm2, sm3 PLANT SAMPLE
TW1 WATER POTENTIAL DESCENT PERIOD
TW2 OPTIMUM IRRIGATION AMOUNT SEARCHING PERIOD
TW3 WATER STRESS CONTROL PERIOD
TW4 WATER CONTENT RECOVERY PERIOD
VSC VISIBLE LIGHT CAMERA
W1, Wk REFLECTION INTENSITY RATIO
WF FERTILIZER OR WATER SUPPLY DEVICE

The invention claimed is:

1. A device for observing water content, the device being disposed facing a background material which covers back surfaces of an observation portion of a plant and at least one sample used as a reference for deriving water content of the observation portion of the plant, the device comprising:
a first light source which radiates a reference beam having a characteristic in which light tends not to be absorbed in water while sequentially scanning toward the background material;
a second light source which radiates a measuring beam having a characteristic in which light tends to be absorbed in water while sequentially scanning toward the background material;
a processor that derives water content contained in the observation portion based on each reflection light of the reference beams reflected on the observation portion and the sample and each reflection light of measuring beams reflected on the observation portion and the sample, in a certain measurement period; and
a controller that displays a time-serial change of the water content, which is contained in the observation portion during the measurement period, derived by the processor on a display.

2. The device for observing water content of claim 1, wherein the sample includes a mixture of saccharides having absorption spectra equivalent to water absorption spectra for each wavelength of the reference beam and the measuring beam with a resin.

3. The device for observing water content of claim 1, wherein the observation portion of the plant and the sample are disposed close to each other in the background material.

4. The device for observing water content of claim 1, wherein the display displays a range of water content of a target illustrating a state where a desired water stress is applied to the observation portion of the plant, and
wherein the controller instructs the display to display an instruction for encouraging irrigation to the observation portion of the plant in response to the fact that water content contained in the observation portion is close to a lower limit of the range of water content of the target.

5. The device for observing water content of claim 1, wherein the display displays a range of water content of a target illustrating a state where a desired water stress is applied to the observation portion of the plant, and
wherein the controller instructs the display to display an instruction for stopping irrigation to the observation portion of the plant in response to the fact that water content contained in the observation portion is close to an upper limit of the range of water content of the target.

6. The device for observing water content of claim 1, wherein the controller controls irradiation timing of the reference beam and the measuring beam so as to provide a non-irradiation period between an irradiation cycle of the reference beam and an irradiation cycle of the measuring beam, and
wherein the processor
subtracts the same wavelength component as the reference beam of sunlight received in the non-irradiation period from the reflection light of the reference beam reflected on each of the observation portion and the sample,
subtracts the same wavelength component as the measuring beam of sunlight received in the non-irradiation period from the reflection light of the measuring beam reflected on each of the observation portion and the sample, and
derives the water content contained in the observation portion based on each reflection light after subtraction.

7. A device for observing water content, the device being disposed facing a background material which covers a back surface of an observation portion of a plant, the device comprising:
a first light source which radiates a reference beam having a characteristic in which light tends not to be absorbed in water while sequentially scanning toward the background material;
a second light source which radiates a measuring beam having a characteristic in which light tends to be absorbed in water while sequentially scanning toward the background material;
a processor that derives water content contained in observation portion based on the reflection light of the reference beam reflected on the observation portion and the reflection light of measuring beam reflected on the observing portion, in a certain measurement period; and a controller that displays a time-serial change of the water content, which is contained in the observation portion during the measurement period, derived by the processor on a display, wherein the controller that controls irradiation timing of the reference beam and the measuring beam so as to provide a non-irradiation period between an irradiation cycle of the reference beam and an irradiation cycle of the measuring beam, and wherein the processor subtracts the same wavelength component as the reference beam of sunlight received in the non-irradiation period from the reflection light of the reference beam reflected on the observation portion, subtracts the same wavelength component as the measuring beam of sunlight received in the non-irradiation period from the reflection light of the measuring reflected on the observing portion, and derives the water content contained in the observing portion based on each reflection light after subtraction.

8. A cultivation device comprising:

the device for observing water content of claim 1; and a cultivation controller that irrigates the plant with a predetermined amount of water based on a time-serial change of water content calculated by the processor in a certain period of the measurement periods.

9. A method for observing water content in a device for observing water content, the device including a first light source and a second light source, the method comprising:

disposing the device for observing water content to face a background material which covers back surfaces of an observation portion of a plant and at least one sample used as a reference for deriving water content of the observation portion of the plant;

radiating a reference beam having a characteristic in which light tends not to be absorbed in water while sequentially scanning toward the background material, by the first light source;

radiating a measuring beam of having a characteristic in which light tends to be absorbed in water while sequentially scanning toward the background material, by the second light source;

deriving water content contained in observation portion based on each reflection light of the reference beams reflected on the observation portion and the sample and each reflection light of measuring beams reflected on the observation portion and the sample, in a certain measurement period on a display unit; and displaying a time-serial change of the water content contained in the observation portion in the measurement period.

10. A sample used as a reference for deriving water content of an observation portion of a plant by a device for observing water content, the sample comprising:

a mixture of saccharides having absorption spectra equivalent to water absorption spectra for each wavelength of a reference beam having a characteristic in which light tends not to be absorbed in water and irradiated by the device for observing water content and a measuring beam having a characteristic in which light tends to be absorbed in water and irradiated by the device for observing water content, with a resin.

11. The sample of claim 10, of which a back surface is covered by the background material disposed facing the device for observing water content, and which is disposed close to the observation portion of the plant disposed with the back surface covered by the background material.

* * * * *